US006034083A

United States Patent [19]

Szczepanski et al.

[11] Patent Number: 6,034,083

[45] Date of Patent: Mar. 7, 2000

[54] PYRIDINE DERIVATIVES AS PESTICIDES

[75] Inventors: Henry Szczepanski, Wallbach; Haukur Kristinsson, Bottmingen; Peter Maienfisch, Rodersdorf; Josef Ehrenfreund, Allschwil, all of Switzerland

[73] Assignee: Novartis Corp., Summit, N.J.

[21] Appl. No.: 09/119,285

[22] Filed: Jul. 20, 1998

Related U.S. Application Data

[62] Division of application No. 08/669,452, filed as application No. PCT/EP94/04222, Dec. 19, 1994, Pat. No. 5,783,704.

[30] Foreign Application Priority Data

Dec. 30, 1993 [CH] Switzerland .......................... 03904/93
Jul. 19, 1994 [CH] Switzerland .......................... 02291/94

[51] Int. Cl.[7] ......................... C07D 401/12; A61K 31/53

[52] U.S. Cl. ............................................ 514/242; 544/182

[58] Field of Search ............................ 514/242; 544/182; 504/229

[56] References Cited

U.S. PATENT DOCUMENTS 5,179,094 1/1993 Kristiansen et al. .................... 514/242

*Primary Examiner*—Jane Fan
*Attorney, Agent, or Firm*—John D. Peabody, III; William A. Teoli, Jr.

[57] ABSTRACT

Compounds of formula (I)

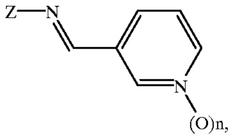

wherein n and Z are as defined in claim 1, and, where appropriate, tautomers thereof, in each case in free form or in salt form, can be used as agrochemical active ingredients and can be prepared in a manner known per se.

7 Claims, No Drawings

PYRIDINE DERIVATIVES AS PESTICIDES

This Appln is a Div of Ser. No. 08/669,452 Jun. 28, 1996 U.S. Pat. 5,783,704 which is a 371 of PCT/EP 94/04222 Dec. 19, 1994.

The invention relates to compounds of formula (I)

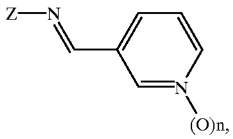

wherein, taking into account the proviso mentioned below, n is 0 or 1, and

Z is a 5- or 6-membered heterocyclyl which is bonded via a nitrogen atom that is part of the basic ring structure of the heterocyclyl radical to the nitrogen atom (shown in formula I) in the 3-substituent of the pyridine ring, in free form or in salt form, where appropriate to tautomers, in free form or in salt form, of those compounds, to a process for the preparation of those compounds and tautomers and to the use of those compounds and tautomers, to pesticidal compositions the active ingredient of which is selected from those compounds and tautomers, in each case in free form or in agrochemically acceptable salt form, to a process for the preparation of those compositions and to the use of those compositions, to plant propagation material treated with those compositions, to a method of controlling pests, to intermediates, in free form or in salt form, for the preparation of those compounds, where appropriate to tautomers, in free form or in salt form, of those intermediates, and to a process for the preparation of those intermediates and their tautomers and to the use of those intermediates and their tautomers.

In the literature, certain pyridine derivatives are proposed as insecticidal active ingredients of pesticides. The biological properties of those known compounds are not entirely satisfactory in the field of pest control, however, and there is therefore a need to provide further compounds having pesticidal properties, especially for controlling insects and representatives of the order Acarina. That problem is solved according to the invention by the provision of the present compounds I.

As is familiar to a person skilled in the art, some compounds I may be in the form of tautomers. Accordingly, hereinbefore and hereinafter compounds I are to be understood as including corresponding tautomers, even though the latter are not specifically mentioned in each case.

Compounds I having at least one basic centre are capable of forming, for example, acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, $C_1$–$C_4$alkanecarboxylic acids, for example acetic acid, or saturated or unsaturated dicarboxylic acids, for example oxalic, malonic, succinic, maleic, fumaric or phthalic acid, or hydroxycarboxylic acids, for example ascorbic, lactic, malic, tartaric or citric acid, or benzoic acid, or with organic sulfonic acids, such as unsubstituted or substituted, for example halo-substituted, $C_1$–$C_4$alkanesulfonic or arylsulfonic acids, for example methanesulfonic or p-toluenesulfonic acid. Furthermore, compounds I having at least one acidic group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethylamine, diethylamine, triethylamine or dimethylpropylamine, or a mono-, di- or tri-hydroxy-lower alkylamine, for example mono-, di- or tri-ethanolamine. Where appropriate, corresponding internal salts may also be formed. Preference is given within the scope of the invention to agrochemically advantageous salts, but salts that have disadvantages for agrochemical purposes, for example salts that are toxic to bees or to fish, are also included; the latter salts are used, for example, in the isolation or purification of free compounds I or the agrochemically acceptable salts thereof. In view of the close relationship between the compounds I in free form and in the form of their salts, hereinbefore and hereinafter any reference to the free compounds I or their salts should be understood as including also the corresponding salts or the free compounds I, respectively, where appropriate and expedient. The same applies to tautomers of compounds I and the salts thereof. The free form is generally preferred.

Preferred forms within the scope of the invention are:

(1) a compound of formula I wherein, taking into account the proviso mentioned below, n is 0;

(2) a compound of formula I wherein, taking into account the proviso mentioned below, Z is a radical of formula (II)

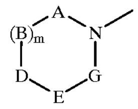

wherein m is 0 or 1, and

A, D, E, G and, when m is 1, B, are each independently of the others O, S, S(=O), $S(=O)_2$, unsubstituted or substituted C or unsubstituted or substituted N, and are each bonded via a single bond or a double bond to the two adjacent ring members to form a stable heterocyclic five-membered ring when m is 0 or a stable heterocyclic six-membered ring when m is 1;

(3) a compound of formula (III)

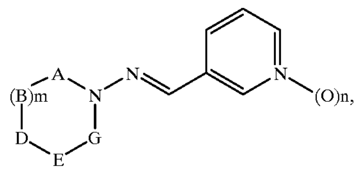

wherein

A is $CR_1R_2$, or, when B is neither O nor S, is $—CR_3═$;

B is $CR_4R_5$, $—CR_6═$, O, S, $NR_7$ or —N═;

D is $CR_{13}R_{14}$, $—CR_{15}═$, O, S, $NR_{16}$ or —N═;

E is $NR_{17}$ or, when D is not a hetero atom, is O or S; and

G is CO, CS, $CNR_{21}$ or $CNOR_{22}$;

$R_7$, $R_{16}$, $R_{17}$ and $R_{21}$ are each independently of the others H, $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio; $C_3$–$C_6$cycloalkyl, $C_3$–$C_6$cycloalkyl substituted by from 1 to 3 substituents from the group consisting of halogen and $C_1$–$C_3$alkyl; $COOR_8$, $CONR_9R_{10}$, $COR_{11}$, $COSR_{12}$, $NR_{18}R_{19}$ or $N{=}CR_{20}$;

$R_1$ and $R_2$ are each independently of the other $R_{23}$ or together are =O, =NH or =S;

$R_4$ and $R_5$ are each independently of the other $R_{23}$ or together are =O, =NH or =S;

$R_{13}$ and $R_{14}$ are each independently of the other $R_{23}$ or together are =O, =NH or =S;

$R_3$, $R_6$, $R_8$, $R_9$, $R_{10}$, $R_{11}$, $R_{12}$, $R_{15}$, $R_{18}$, $R_{19}$, $R_{22}$ and $R_{23}$ are each independently of the others H, halogen, $C_1$–$C_5$alkyl, $C_1$–$C_5$alkenyl, $C_1$–$C_5$alkoxy, $C_1$–$C_3$alkoxy-$C_1$–$C_5$alkyl, hydroxy-$C_1$–$C_5$alkyl, $C_1$–$C_5$alkoxycarbonyl, $C_1$–$C_5$alkylthio; $C_1$–$C_5$alkyl substituted by from 1 to 3 substituents from the group consisting of halogen, hydroxy, $C_1$–$C_3$alkoxy, $C_1$–$C_3$alkoxycarbonyl and $C_1$–$C_3$alkylthio; $C_3$–$C_6$cycloalkyl or $C_3$–$C_6$cycloalkyl substituted by from 1 to 3 substituents from the group consisting of halogen and $C_1$–$C_3$alkyl; and $R_{20}$ is $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio; $C_3$–$C_6$cycloalkyl, $C_3$–$C_6$cycloalkyl substituted by from 1 to 3 substituents from the group consisting of halogen and $C_1$–$C_3$alkyl; unsubstituted or substituted phenyl or unsubstituted or substituted pyridyl;

with the proviso that in compounds of formula I wherein Z is a radical of formula II and n is 0, G is other than CO when m is 1, D is —N=, $R_1$ is H, $C_1$–$C_5$alkyl or $C_3$–$C_6$cycloalkyl, $R_2$ is H or $C_1$–$C_6$alkyl, $R_6$ is H, $C_1$–$C_5$alkyl, $C_3$–$C_6$cycloalkyl, $C_1$–$C_3$alkoxy-$C_1$–$C_5$alkyl or halo-$C_1$–$C_2$alkyl, and $R_{17}$ is H;

and with the further proviso that in compounds of formula I wherein Z is a radical of formula II and n is 1, G is other than CO when m is 1, D is —N=, $R_1$ and $R_2$ are each independently of the other H or $C_1$–$C_5$alkyl, $R_6$ is $C_1$–$C_5$alkyl or $C_3$–$C_6$cycloalkyl, and $R_{17}$ is H;

and with the further proviso that in compounds of formula I wherein Z is a radical of formula II, G is other than CO when m is 0, D is —$CR_{15}$=, $R_3$ and $R_{15}$ are each independently of the other H, $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio; $C_3$–$C_6$cycloalkyl or $C_3$–$C_6$cycloalkyl substituted by from 1 to 3 substituents from the group consisting of halogen and $C_1$–$C_3$alkyl; and $R_{17}$ is H, $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio; $C_3$–$C_6$cycloalkyl, $C_3$–$C_6$cycloalkyl substituted by from 1 to 3 substituents from the group consisting of halogen and $C_1$–$C_3$alkyl; $COOR_8$, $CONR_9R_{10}$, $COR_{11}$, $COSR_{12}$, $NR_{18}R_{19}$ or $N{=}CR_{20}$;

(4) a compound of formula III wherein, taking into account the proviso mentioned above, B, when m is 1, is $CR_4R_5$, —$CR_6$=, O, $NR_7$ or —N=, preferably $CR_4R_5$ or —$CR_6$=, especially $CR_4R_5$;

(5) a compound of formula III wherein, taking into account the proviso mentioned above, D is $CR_{13}R_{14}$, —$CR_{15}$=, $NR_{16}$ or —N=, preferably $CR_{13}R_{14}$, —$CR_{15}$= or —N=, especially $CR_{13}R_{14}$ or —N=;

(6) a compound of formula III wherein, taking into account the proviso mentioned above, E is $NR_{17}$;

(7) a compound of formula III wherein, taking into account the proviso mentioned above, G is CO, CS or $CNR_{21}$, preferably CO or CS, especially CO;

(8) a compound of formula III wherein, taking into account the proviso mentioned above, $R_1$ and $R_2$ are each independently of the other H, $C_1$–$C_5$alkyl, $C_1$–$C_5$alkyl substituted by from 1 to 3 substituents from the group consisting of halogen and $C_1$–$C_3$alkoxy, or $C_3$–$C_6$cycloalkyl, preferably H, $C_1$–$C_4$alkyl or $C_3$–$C_6$cycloalkyl, especially H or $C_1$–$C_4$alkyl;

(9) a compound of formula III wherein, taking into account the proviso mentioned above, $R_1$ and $R_2$ together are =O or =S, preferably =O;

(10) a compound of formula III wherein, taking into account the proviso mentioned above, $R_3$ is H, halogen, $C_1$–$C_3$alkyl, $C_1$–$C_3$alkylthio, $C_1$–$C_3$alkyl substituted by from 1 to 3 substituents from the group consisting of halogen, hydroxy, $C_1$–$C_2$alkoxy and $C_1$–$C_2$alkylthio, or $C_3$–$C_6$cycloalkyl, preferably H, $C_1$–$C_3$alkyl, $C_1$–$C_2$alkyl substituted by from 1 to 3 substituents from the group consisting of halogen, hydroxy and $C_1$–$C_2$alkoxy, or $C_3$–$C_6$cycloalkyl, especially H, $C_1$–$C_3$alkyl, $C_1$–$C_2$alkyl or $C_3$–$C_6$cycloalkyl;

(11) a compound of formula III wherein, taking into account the proviso mentioned above, $R_4$ and $R_5$ are each independently of the other H, $C_1$–$C_3$alkyl, $C_1$–$C_3$alkoxy, $C_1$–$C_3$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, preferably H, $C_1$–$C_3$alkyl, $C_1$–$C_3$alkoxy or $C_3$–$C_6$cycloalkyl, especially H, $C_1$–$C_3$alkyl or $C_1$–$C_3$alkoxy;

(12) a compound of formula III wherein, taking into account the proviso mentioned above, $R_4$ and $R_5$ together are =O or =S, preferably =O;

(13) a compound of formula III wherein, taking into account the proviso mentioned above, $R_6$ is H, $C_1$–$C_5$alkyl, $C_1$–$C_5$alkoxy or $C_3$–$C_6$cycloalkyl, preferably H, $C_1$–$C_4$alkyl or $C_3$–$C_6$cycloalkyl, especially H or $C_1$–$C_3$alkyl;

(14) a compound of formula III wherein, taking into account the proviso mentioned above, $R_7$ is H, $C_1$–$C_3$alkyl, $C_1$–$C_3$alkyl substituted by from 1 to 3 substituents from the group consisting of halogen and $C_1$–$C_3$alkoxy; $C_3$–$C_6$cycloalkyl, $COOR_8$, $CONR_9R_{10}$ or $COR_{11}$, preferably H, $C_1$–$C_3$alkyl, $C_1$–$C_3$alkyl substituted by from 1 to 3 substituents from the group halogen; $CONR_9R_{10}$ or $COR_{11}$, especially H, $C_1$–$C_3$alkyl or $COR_{11}$;

(15) a compound of formula III wherein, taking into account the proviso mentioned above, $R_8$ is $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, preferably $C_1$–$C_4$alkyl or $C_3$–$C_6$cycloalkyl, especially $C_1$–$C_3$alkyl;

(16) a compound of formula III wherein, taking into account the proviso mentioned above, $R_9$ and $R_{10}$ are each independently of the other H, $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, preferably H, $C_1$–$C_4$alkyl or $C_3$–$C_6$cycloalkyl, especially H or $C_1$–$C_3$alkyl;

(17) a compound of formula III wherein, taking into account the proviso mentioned above, $R_{11}$ is $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, preferably $C_1$–$C_4$alkyl, $C_1$–$C_4$alkyl substituted by from 1 to 3 substituents from the group consisting of halogen and $C_1$–$C_3$alkoxy, or $C_3$–$C_6$cycloalkyl, especially $C_1$–$C_4$alkyl;

(18) a compound of formula m wherein, taking into account the proviso mentioned above, $R_{12}$ is $C_1$–$C_5$alkyl;

(19) a compound of formula III wherein, taking into account the proviso mentioned above, $R_{13}$ and $R_{14}$ are each independently of the other H, $C_1$–$C_5$alkyl, $C_1$–$C_5$alkenyl, $C_1$–$C_5$alkyl substituted by from 1 to 3 substituents from the group consisting of halogen, hydroxy, $C_1$–$C_3$alkoxy, $C_1$–$C_3$alkoxycarbonyl and $C_1$–$C_3$alkylthio, or $C_3$–$C_6$cycloalkyl, preferably H, $C_1$–$C_5$alkyl or $C_3$–$C_6$cycloalkyl, especially H or $C_1$–$C_3$alkyl;

(20) a compound of formula III wherein, taking into account the proviso mentioned above, $R_{13}$ and $R_{14}$ together are =O;

(21) a compound of formula III wherein, taking into account the proviso mentioned above, $R_{15}$ is H, $C_1$–$C_5$alkyl, $C_1$–$C_5$alkoxycarbonyl or $C_3$–$C_6$cycloalkyl, preferably H, $C_1$–$C_3$alkyl or $C_3$–$C_6$cycloalkyl, especially H or $C_1$–$C_3$alkyl;

(22) a compound of formula III wherein, taking into account the proviso mentioned above, $R_{16}$ is H, $C_1$–$C_5$alkyl, $C_3$–$C_6$cycloalkyl, $COOR_8$, $CONR_9R_{10}$ or $COR_{11}$, preferably H, $C_1$–$C_5$alkyl or $COR_{11}$, especially H or $COR_{11}$;

(23) a compound of formula III wherein, taking into account the proviso mentioned above, $R_{17}$ is H, $C_1$–$C_5$alkyl, $C_1$–$C_5$alkyl substituted by from 1 to 3 substituents from the group halogen, or $C_3$–$C_6$cycloalkyl, $COOR_8$, $CONR_9R_{10}$, $COR_{11}$ or $N{=}CR_{20}$, preferably H, $C_1$–$C_5$alkyl, $CONR_9R_{10}$, $COR_{11}$ or $N{=}CR_{20}$, especially H, $C_1$–$C_3$alkyl or $COR_{11}$;

(24) a compound of formula III wherein, taking into account the proviso mentioned above, $R_{18}$ and $R_{19}$ are each independently of the other H, $C_1$–$C_5$alkyl or $C_3$–$C_6$cycloalkyl, preferably H or $C_1$–$C_5$alkyl, especially $C_1$–$C_3$alkyl;

(25) a compound of formula III wherein, taking into account the proviso mentioned above, $R_{20}$ is $C_1$–$C_5$alkyl, $C_3$–$C_6$cycloalkyl, unsubstituted or substituted phenyl or unsubstituted or substituted pyridyl, preferably unsubstituted or substituted phenyl or unsubstituted or substituted pyridyl, especially unsubstituted or substituted pyridyl;

(26) a compound of formula m wherein, taking into account the proviso mentioned above, $R_{21}$ is H or $C_1$–$C_5$alkyl, preferably H;

(27) a compound of formula III wherein, taking into account the proviso mentioned above, $R_{22}$ is $C_1$–$C_5$alkyl, preferably $C_1$–$C_2$alkyl;

(28) a compound of formula III wherein, taking into account the proviso mentioned above, n is 0, B, when m is 1, is $CR_4R_5$, —$CR_6$=, O, $NR_7$ or —N=, D is $CR_{13}R_{14}$, —$CR_{15}$=, $NR_{16}$ or —N=, E is $NR_{17}$, G is CO, CS or $CNR_{21}$, $R_1$ and $R_2$ are each independently of the other H, $C_1$–$C_5$alkyl, $C_1$–$C_5$alkyl substituted by from 1 to 3 substituents from the group consisting of halogen and $C_1$–$C_3$alkoxy, or $C_3$–$C_6$cycloalkyl, or together are =O or =S, $R_3$ is H, halogen, $C_1$–$C_3$alkyl, $C_1$–$C_3$alkylthio, $C_1$–$C_3$alkyl substituted by from 1 to 3 substituents from the group consisting of halogen, hydroxy, $C_1$–$C_2$alkoxy and $C_1$–$C_2$alkylthio, or $C_3$–$C_6$cycloalkyl, $R_4$ and $R_5$ are each independently of the other H, $C_1$–$C_3$alkyl, $C_1$–$C_3$alkoxy, $C_1$–$C_3$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, or together are =O or =S, $R_6$ is H, $C_1$–$C_5$alkyl, $C_1$–$C_5$alkoxy or $C_3$–$C_6$cycloalkyl, $R_7$ is H, $C_1$–$C_3$alkyl, $C_1$–$C_3$alkyl substituted by from 1 to 3 substituents from the group consisting of halogen and $C_1$–$C_3$alkoxy, $C_3$–$C_6$cycloalkyl, $COOR_8$, $CONR_9R_{10}$ or $COR_{11}$, $R_8$ is $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, $R_9$ and $R_{10}$ are each independently of the other H, $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, $R_{11}$ is $C_1$–$C_5$alkyl, $C_1$–$C_5$alkyl substituted by from 1 to 3 substituents from the group consisting of halogen, hydroxy, $C_1$–$C_3$alkoxy and $C_1$–$C_3$alkylthio, or $C_3$–$C_6$cycloalkyl, $R_{13}$ and $R_{14}$ are each independently of the other H, $C_1$–$C_5$alkyl, $C_1$–$C_5$alkenyl, $C_1$–$C_5$alkyl substituted by from 1 to 3 substituents from the group consisting of halogen, hydroxy, $C_1$–$C_3$alkoxy, $C_1$–$C_3$alkoxycarbonyl and $C_1$–$C_3$alkylthio, or $C_3$–$C_6$cycloalkyl, or together are =O, $R_{15}$ is H, $C_1$–$C_5$alkyl, $C_1$–$C_5$alkoxycarbonyl or $C_3$–$C_6$cycloalkyl, $R_{16}$ is H, $C_1$–$C_5$alkyl, $C_3$–$C_6$cycloalkyl, $COOR_8$, $CONR_9R_{10}$ or $COR_{11}$, $R_{17}$H, $C_1$–$C_5$alkyl, $C_1$–$C_5$alkyl substituted by from 1 to 3 substituents from the group halogen, or $C_3$–$C_6$cycloalkyl, $COOR_8$, $CONR_9R_{10}$, $COR_{11}$ or $N{=}CR_{20}$, $R_{20}$ is $C_1$–$C_5$alkyl, $C_3$–$C_6$cycloalkyl, unsubstituted or substituted phenyl or unsubstituted or substituted pyridyl, and $R_{21}$ is H or $C_1$–$C_5$alkyl;

(29) a compound of formula III wherein, taking into account the proviso mentioned above, n is0, B, when m is 1, is $CR_4R_5$ or —$CR_6$=, D is $CR_{13}R_{14}$, —$CR_{15}$= or —N=, E is $NR_{17}$, G is CO or CS, $R_1$ and $R_2$ are each independently of the other H, $C_1$–$C_4$alkyl, or $C_3$–$C_6$cycloalkyl, or together are =O or =S, $R_3$ is H, $C_1$–$C_3$alkyl, $C_1$–$C_2$alkyl substituted by from 1 to 3 substituents from the group consisting of halogen, hydroxy and $C_1$–$C_2$alkoxy, or $C_3$–$C_6$cycloalkyl, $R_4$ and $R_5$ are each independently of the other H, $C_1$–$C_3$alkyl, $C_1$–$C_3$alkoxy or $C_3$–$C_6$cycloalkyl, or together are =O or =S, $R_6$ is H, $C_1$–$C_4$alkyl or $C_3$–$C_6$cycloalkyl, $R_{13}$ and $R_{14}$ are each independently of the other H, $C_1$–$C_5$alkyl or $C_3$–$C_6$cycloalkyl, or together are =O, $R_{15}$ is H, $C_1$–$C_3$alkyl or $C_3$–$C_6$cycloalkyl, $R_{17}$ is H, $C_1$–$C_5$alkyl, $CONR_9R_{10}$, $COR_{11}$ or $N{=}CR_{20}$, and $R_{20}$ is unsubstituted or substituted phenyl or unsubstituted or substituted pyridyl;

(30) a compound of formula III wherein, taking into account the proviso mentioned above, n is 0, B, when m is 1, is $CR_4R_5$, D is $CR_{13}R_{14}$ or —N=, E is $NR_{17}$, G is CO, $R_1$ and $R_2$ are each independently of the other H or $C_1$–$C_4$alkyl, or together are =O, $R_3$ is H, $C_1$–$C_3$alkyl, $C_1$–$C_2$alkyl or $C_3$–$C_6$cycloalkyl, $R_4$ and $R_5$ are each independently of the other H, $C_1$–$C_3$alkyl or $C_1$–$C_3$alkoxy, or together are =O, $R_{13}$ and $R_{14}$ are each independently of the other H or $C_1$–$C_3$alkyl, or together are =O, and $R_{17}$ is H, $C_1$–$C_3$alkyl, or $COR_{11}$;

in each case in free form or in salt form, and where appropriate a tautomer, in free form or in salt form, of that compound.

Special preference is given within the scope of the invention to the compounds of formula I given in Examples P1 to P9.

Within the scope of the invention preference is given specifically to the compounds of formula I wherein n is 0 and Z is 4-methyl-2-oxo-perhydroimidazol-1-yl, and n is 1 and Z is 6-ethoxymethyl-4,5-dihydro-2H[1,2,4]triazin-3-on-4-yl.

Unless otherwise defined, the general terms used hereinbefore and hereinafter have the meanings given below.

Halogen—as a group per se and as a structural unit of other groups and compounds, such as haloalkyl and halocycloalkyl—is fluorine, chlorine, bromine or iodine, especially fluorine, chlorine or bromine, more especially fluorine or chlorine.

Unless otherwise defined, carbon-containing groups and compounds each contain from 1 up to and including 6, preferably from 1 up to and including 4, especially 1 or 2, carbon atoms.

$C_3$–$C_6$cycloalkyl—as a group per se and as a structural unit of other groups and compounds, such as halocycloalkyl—is cyclopropyl, cyclobutyl, cyclopentyl or cyclohexyl.

Alkyl—as a group per se and as a structural unit of other groups and compounds, such as haloalkyl, alkoxy and alkylthio—is, in each case duly taking into account the number of carbon atoms present in the group or compound in question, either straight-chained, for example methyl, ethyl, propyl or butyl, or branched, for example isopropyl, isobutyl, sec-butyl, tert-butyl, isopentyl or neopentyl.

Halo-substituted carbon-containing groups and compounds, such as haloalkyl or halocycloalkyl, may be partially halogenated or perhalogenated, it being possible in the case of multiple halogenation for the halogen substituents to be identical or different. Examples of haloalkyl—as a group per se and as a structural unit of other groups and compounds, such as haloalkylthio—are methyl mono- to tri-substituted by fluorine, chlorine and/or by bromine, such as $CHF_2$ or $CF_3$; ethyl mono- to penta-substituted by fluorine, chlorine and/or by bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl mono- to hepta-substituted by fluorine, chlorine and/or by bromine, such as $CH_2CHBrCH_2Br$, $CF_2CHFCF_3$, $CH_2CF_2CF_3$ or $CH(CF_3)_2$; butyl mono- to nona-substituted by fluorine, chlorine and/or by bromine, or one of the isomers thereof, such as $CF(CF_3)CHFCF_3$ or $CH_2(CF_2)_2CF_3$; and pentyl mono- to undeca-substituted by fluorine, chlorine and/or by bromine, or one of the isomers thereof, such as $CF(CF_3)CHCH_2FCF_3$ or $CH_2CH_2CH_2CH_2CH_2Cl$.

The invention relates also to a process for the preparation of the compounds of formula I or, where appropriate, the tautomers thereof, in each case in free form or in salt form, taking into account the proviso mentioned above, which process comprises, for example a) for the preparation of a compound of formula I wherein n is 0, reacting a compound of formula $$Z{-}NH_2 \quad (IV),$$

which is known or which can be prepared analogously to corresponding known compounds and wherein Z is as defined for formula I, preferably in the presence of an acid, with pyridine-3-carbaldehyde, or b) for the preparation of a compound of formula I wherein n is 1, reacting a compound of formula IV, preferably in the presence of an acid, with N-oxidopyridinio-3-carbaldehyde or N-oxidopyridinio-3-carbaldehyde dimethylacetal, which are known, or c) for the preparation of a compound of formula I wherein Z is a radical of formula II and wherein n is 0, G is CO and E is NH, heating a compound of formula (V)

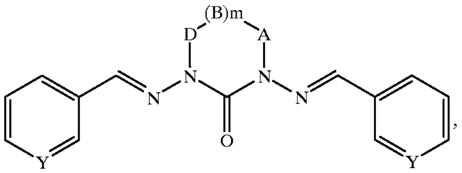

which is known or can be prepared analogously to corresponding known compounds and wherein A, B, D and m are as defined for formula I and Y is N, preferably in the presence of a base, or d) for the preparation of a compound of formula I wherein Z is a radical of formula II and wherein n is 0, G is CO and E is $NR_{17}$, $R_{17}$ being other than H, reacting a compound of formula I wherein n is 0, G is CO and E is NH, preferably in the presence of a base, with a compound of formula $R_{17}COX_1$ wherein $X_1$ is a leaving group, preferably halogen, especially chlorine, and in each case, if desired, converting a compound of formula I obtainable according to the process or by a different method, or a tautomer thereof, in each case in free form or in salt form, into a different compound of formula I or a tautomer thereof, for example converting a compound of formula I wherein n is 0 into a compound of formula I wherein n is 1, separating a mixture of isomers obtainable according to the process and isolating the desired isomer and/or converting a free compound of formula I obtainable according to the process or a tautomer thereof into a salt or converting a salt of a compound of formula I obtainable according to the process or a tautomer thereof into the free compound of formula I or a tautomer thereof or into a different salt.

The invention relates also to a process for the preparation of the compounds of formula IV, in each case in free form or in salt form, which process comprises, for example, e) for the preparation of a compound of formula IV wherein Z is a radical of formula II and wherein G is CO, D is $CR_{15}$ and E is $NR_{17}$, reacting a compound of formula (VI)

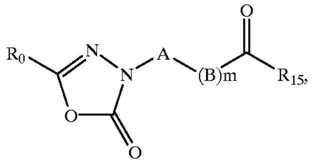

which is known or can be prepared analogously to corresponding known compounds and wherein A, B, $R_{15}$ and m are as defined for formula III and $R_0$ is a $C_1$–$C_6$alkyl group, with a compound of formula $R_{17}NH_2$ wherein $R_{17}$ is as defined for formula III and then hydrolysing the resulting product, preferably in the presence of an acid, or f) for the preparation of a compound of formula IV wherein Z is a radical of formula II and wherein A is —$CR_3$=, D is —N=, E is NH, G is CO and m is 0, reacting a compound of the formula $CO(NHNH_2)_2$, which is known or which can be prepared analogously to corresponding known compounds, with a compound of the formula $R_3C(OR)_3$, which is known or can be prepared analogously to corresponding known compounds, and wherein R is a $C_1$–$C_6$alkyl group, or g) for the preparation of a compound of formula IV wherein Z is a radical of formula II and wherein E is NH and G is CO, reacting a compound of formula (VII)

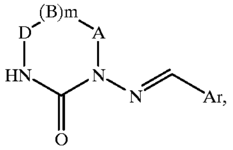

which is known or which can be prepared analogously to corresponding known compounds and wherein A, B, D and m are as defined for formula III and Ar is unsubstituted or substituted phenyl or pyridyl, with hydrazine, or h) for the preparation of a compound of formula IV wherein Z is a radical of formula II and wherein A is —$CR_3$=, D is —$CR_{15}$=, E is NH, G is CO and m is 0, hydrolysing a compound of formula (VIII)

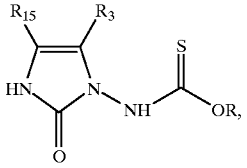

which is known or can be prepared analogously to corresponding known compounds and wherein $R_3$ and $R_{15}$ are as defined for formula III and R is a $C_1$–$C_6$alkyl group, preferably in the presence of an acid, or i) for the preparation of a compound of formula IV wherein Z is a radical of formula II and wherein A is $CR_1R_2$, B is —$CR_6$=, m is 1, D is —N=, E is NH and G is CO, hydrolysing a compound of formula (IX)

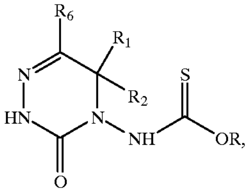

which is novel and wherein $R_1$, $R_2$ and $R_6$ are as defined for formula III and R is a $C_1$–$C_6$alkyl group, preferably in the presence of an acid, or j) for the preparation of a compound of formula IV wherein Z is a radical of formula II and wherein A is $CR_1R_2$, B is $CHR_4$, m is 1, D and E are NH, and G is CO, hydrogenating a compound of formula (X)

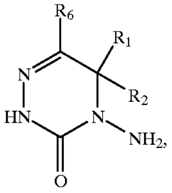

which is known or can be prepared analogously to corresponding known compounds and wherein $R_1$, $R_2$ and $R_6$ are as defined for formula III, preferably in the presence of a reduction catalyst or a hydrogenating agent, and in each case, if desired, converting a compound of formula VI obtainable according to the process or by a different method, or a tautomer thereof, in each case in free form or in salt form, into a different compound of formula VI or a tautomer thereof, and/or separating a mixture of isomers obtainable according to the process and isolating the desired isomer.

The invention relates also to a process for the preparation of the compounds of formula V, in each case in free form or in salt form, which process comprises, for example k) for the preparation of a compound of formula V wherein A is as defined for formula III and B, when m is 1, is $CR_4R_5$ or —$CR_6$=, and D is $CHR_{13}$ or —$CR_{15}$=, and Y is CH or N, reacting a compound of formula (XI)

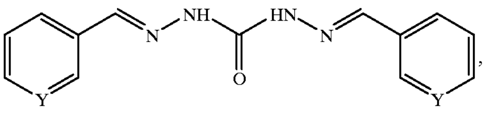

which is known or can be prepared analogously to corresponding known compounds and wherein Y is CH or N, preferably in the presence of an acid with a compound of formula (XII)

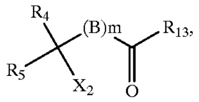

which is known or can be prepared analogously to corresponding known compounds and wherein $R_4$, $R_5$ and $R_{13}$ are as defined for formula III, B, when m is 1, is $CR_4R_5$ or —$CR_6$=, and $X_2$ is a leaving group, preferably halogen, especially chlorine, or with a compound of formula (XIII)

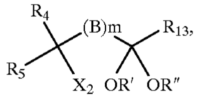

which is known or can be prepared analogously to corresponding known compounds and wherein $R_4$, $R_5$, $R_{13}$ and $X_2$ are as defined for formula XII and B, when m is 1, is $CR_4R_5$ or —$CR_6$=, and R' and R" are each independently of the other $C_1$–$C_6$alkyl or together are —$(CH_2)_p$—, wherein p is 2 or 3, or with a compound of formula (XIV)

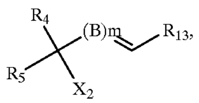

which is known or can be prepared analogously to corresponding known compounds and wherein $R_4$, $R_5$, $R_{13}$ and $X_2$ are as defined for formula XII, m is 1 and B is —$CR_6$=, and in each case, if desired, converting a compound of formula V obtainable according to the process or by a different method, or a tautomer thereof, in each case in free form or in salt form, into a different compound of formula V or a tautomer thereof, and/or separating a mixture of isomers obtainable according to the process and isolating the desired isomer.

The invention relates also to a process for the preparation of the compounds ot formula VII, in each case in free form or in salt form, which process comprises, for example 1) heating a compound of formula V, preferably in the presence of a base, and in each case, if desired, converting a compound of formula VII obtainable according to the process or by a different method, or a tautomer thereof, in each case in free form or in salt form, into a different compound of formula VII or a tautomer thereof, and/or separating a mixture of isomers obtainable according to the process and isolating the desired isomer.

The invention relates also to a process for the preparation of the compounds of formula VIII, in each case in free form or in salt form, which process comprises, for example m) reacting a compound of formula (XV)

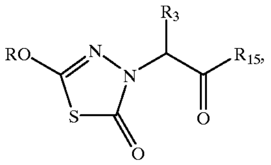

which is novel and wherein R, $R_3$ and $R_{15}$ are as defined for formula VIII, with ammonia and, if desired, converting a compound of formula VIII obtainable according to the process or by a different method, or a tautomer thereof, in each case in free form or in salt form, into a different compound of formula VIII or a tautomer thereof, and/or separating a mixture of isomers obtainable according to the process and isolating the desired isomer.

The compounds of formula IX wherein $R_1$, $R_2$ and $R_6$ are as defined for formula III and R is a $C_1$–$C_6$alkyl group are novel and the invention relates also thereto.

The invention relates also to a process for the preparation of the compounds of formula IX, in each case in free form or in salt form, which process comprises, for example n) rearranging a compound of formula (XVI)

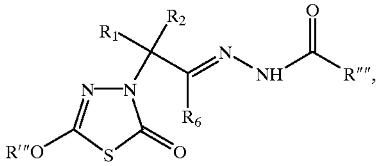

which is novel and wherein $R_1$, $R_2$ and $R_6$ are as defined for formula III and R''' and R'''' are each independently of the other $C_1$–$C_6$alkyl, preferably methyl, or R''' is $C_1$–$C_6$alkyl and R'''' is $C_1$–$C_5$alkoxy, preferably in the presence of an acid or a base, and in each case, if desired, converting a compound of formula IX obtainable according to the process or by a different method, or a tautomer thereof, in each case in free form or in salt form, into a different compound of formula IX or a tautomer thereof, and/or separating a mixture of isomers obtainable according to the process and isolating the desired isomer.

The compounds of formula XV wherein R, $R_3$ and $R_{15}$ are as defined for formula VIII are novel and the invention relates also thereto.

The invention relates also to a process for the preparation of the compounds of formula XI, in each case in free form or in salt form, which process comprises, for example o) reacting a compound of formula (XVII)

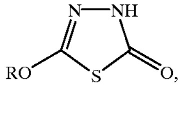

which is known or can be prepared analogously to corresponding known compounds, with a compound of the formula $X_3CH(R_3)COR_{15}$, which is known or can be prepared analogously to corresponding known compounds and wherein R, $R_3$ and $R_{15}$ are as defined for formula VIII and $X_3$ is a leaving group, for example halogen, preferably chlorine, preferably in the presence of a base, and in each case, if desired, converting a compound of formula XV obtainable according to the process or by a different method, or a tautomer thereof, in each case in free form or in salt form, into a different compound of formula XV or a tautomer thereof, and/or separating a mixture of isomers obtainable according to the process and isolating the desired isomer.

The compounds of formula XVI wherein $R_1$, $R_2$ and $R_6$ are as defined for formula III and R''' and R'''' are each independently of the other a $C_1$–$C_6$alkyl group, or R''' is a $C_1$–$C_6$alkyl group and R'''' is a $C_1$–$C_5$alkoxy group, are novel and the invention relates also thereto.

The invention relates also to a process for the preparation of the compounds of formula XVI, in each case in free form or in salt form, which process comprises, for example p) reacting a compound of formula (XVIII)

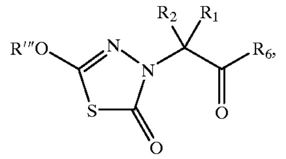

wherein R''', $R_1$, $R_2$ and $R_6$ are as defined for formula XVI, with a compound of the formula $NH_2NHCOR'$, which is known or can be prepared analogously to corresponding known compounds and wherein R' is as defined for formula XVI, preferably in the presence of an acid, and in each case, if desired, converting a compound of formula XVI obtainable according to the process or by a different method, or a tautomer thereof, in each case in free form or in salt form, into a different compound of formula XVI or a tautomer thereof, and/or separating a mixture of isomers obtainable according to the process and isolating the desired isomer.

The compounds of formula XVIII wherein $R_1$, $R_2$ and $R_6$ are as defined for formula III and R''' is a $C_1$–$C_6$alkyl group are novel and the invention relates also thereto.

The invention relates also to a process for the preparation of the compounds of formula XVIII, in each case in free from or in salt form, which process comprises, for example q) reacting a compound of formula XVII with a compound of the formula $R_6COCR_1R_2X$, which is known or can be prepared analogously to corresponding known compounds and wherein $R_1$, $R_2$ and $R_6$ are as defined for formula III and X is a leaving group, for example halogen, preferably chlorine, preferably in the presence of a base, and in each case, if desired, converting a compound of formula XVIII obtainable according to the process or by a different method, or a tautomer thereof, in each case in free form or in salt form, into a different compound of formula XVIII or a tautomer thereof, and/or separating a mixture of isomers obtainable according to the process and isolating the desired isomer.

The remarks made above in relation to tautomers and/or salts of compounds I apply analogously to the starting materials listed hereinbefore and hereinafter as regards the tautomers and/or salts thereof.

The reactions described hereinbefore and hereinafter are carried out in a manner known per se, for example in the absence or, customarily, in the presence of a suitable solvent or diluent or of a mixture thereof, the reactions being carried out as required with cooling, at room temperature or with heating, for example in a temperature range from approximately −80° C. to the boiling temperature of the reaction medium, preferably from approximately −20° C. to approximately +150° C., and, if necessary, in a closed vessel, under pressure, in an inert gas atmosphere and/or under anhydrous conditions. Especially advantageous reaction conditions can be found in the Examples.

The starting materials given hereinbefore and hereinafter that are used for the preparation of compounds I, and where appropriate the tautomers thereof, in each case in free form or in salt form, are known or can be prepared in accordance with methods known per se, for example in accordance with the instructions given below.

Variant a):

Suitable acid catalysts for facilitating the reaction are, for example, those acids, used in catalytic amounts, that are listed above as suitable for the formation of acid addition salts with compounds I.

The reactants can be reacted with one another as such, i.e. without the addition of a solvent or diluent, for example in the melt In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents. If the reaction is carried out in the presence of an acid catalyst, acids used in excess, for example strong organic carboxylic acids, such as unsubstituted or substituted, for example halo-substituted, $C_1$–$C_4$alkanecarboxylic acids, for example formic, acetic or propionic acid, may also serve as solvents or diluents.

The reaction is advantageously carried out in a temperature range from approximately 0° C. to approximately +100° C., preferably from approximately 20° C. to approximately +80° C.

In a preferred form of Variant a), the compound IV is reacted in an alcohol, preferably ethanol, in the presence of a mineral acid, preferably hydrochloric acid, at from 60 to 80°, preferably 80°, with pyridine-3-carbaldehyde.

Variant b):

Suitable acid catalysts for facilitating the reaction are, for example, acids of the type indicated in Variant a).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range of from approximately 0° C. to approximately +100° C., preferably from approximately 20° C. to approximately +80° C.

Variant c):

Suitable bases for facilitating the reaction are, for example, alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. The following may be mentioned by way of example: sodium hydroxide, hydride, amide, methanolate, acetate or carbonate, potassium tert-butanolate, hydroxide, carbonate or hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +100° C., preferably from approximately 20° C. to approximately +80° C.

Variant d):

Suitable bases for facilitating the reaction are, for example, those of the type mentioned under Variant c).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant c).

The reaction is advantageously carried out in a temperature range from approximately 0° C. to approximately +100° C., preferably from approximately 20° C. to approximately +80° C.

Variant e):

Suitable acid catalysts for facilitating the reaction are, for example, acids of the type mentioned under Variant a).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range from approximately 0° C. to approximately +100° C., preferably from approximately 20° C. to approximately +80° C.

Variant f):

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range from approximately 0° C. to approximately +100° C., preferably from approximately 20° C. to approximately +80° C.

Variant g):

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range from approximately 0° C. to approximately +100° C., preferably from approximately 20° C. to approximately +80° C.

Variant h):

Suitable acid catalysts for facilitating the reaction are, for example, acids of the type mentioned under Variant a).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range from approximately 0° C. to approximately +100° C., preferably from approximately 20° C. to approximately +80° C.

Variant i):

Suitable acid catalysts for facilitating the reaction are, for example, acids of the type mentioned under Variant a).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range from approximately 0° C. to approximately +100° C., preferably from approximately 20° C. to approximately +80° C.

Variant j):

Suitable reduction catalysts are the transitions metals customarily used, preferably Ni, Pt, Pd, Fe, but also customary hydrogenating agents, such as lithium aluminium hydride, sodium borohydride or diborane.

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range from approximately 0° C. to approximately +100° C., preferably from approximately 20° C. to approximately +80° C.

Variant k):

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature range from approximately 0° C. to approximately +100° C., preferably from approximately 20° C. to approximately +80° C.

Variant l):

Suitable bases for facilitating the reaction are, for example, those of the type mentioned under Variant c).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant c).

The reaction is advantageously carried out in a temperature range from approximately 0° C. to approximately +100° C., preferably from approximately 20° C. to approximately +80° C.

Variant m):

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant c).

The reaction is advantageously carried out in a temperature range from approximately 0° C. to approximately +100° C., preferably from approximately 20° C. to approximately +80° C.

Variant n):

Suitable bases for facilitating the reaction are, for example, those of the type mentioned under Variant c).

Suitable acid catalysts for facilitating the reaction are, for example, acids of the type mentioned under Variant a).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant a).

The reaction is advantageously carried out in a temperature -range from approximately 0° C. to approximately +100° C., preferably from approximately 20° C. to approximately +80° C.

Variant o):

Suitable bases for facilitating the reaction are, for example, those of the type mentioned under Variant c).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents are, for example, those of the type mentioned under Variant c).

The reaction is advantageously carried out in a temperature range from approximately 0° C. to approximately +100° C., preferably from approximately 20° C. to approximately +80° C.

Variant p):

Suitable acid catalysts for facilitating the reaction are, for example, acids of the type mentioned under Variant a).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitrites, such as acetonitrile or propionitrile; and sulfoxides, such as dimethyl sulfoxide. If the reaction is carried out in the presence of an acid catalyst, acids used in excess, for example strong organic carboxylic acids, such as unsubstituted or substituted, for example halo-substituted, $C_1$–$C_4$alkanecarboxylic acids, for example formic, acetic or propionic acid, may also serve as solvents or diluents.

The reaction is advantageously carried out in a temperature range from approximately 0° C. to approximately +100° C., preferably from approximately 20° C. to approximately +80° C.

Salts of compounds I can be prepared in a manner known per se. For example, acid addition salts of compounds I are obtained by treatment with a suitable acid or a suitable ion exchange reagent, and salts with bases are obtained by treatment with a suitable base or a suitable ion exchange reagent.

Salts of compounds I can be converted into the free compounds I in customary manner: acid addition salts, for example, by treatment with a suitable basic agent or a suitable ion exchange reagent, and salts with bases, for example, by treatment with a suitable acid or a suitable ion exchange reagent.

Salts of compounds I can be converted into different salts of compounds I in a manner known per se: acid addition salts, for example, can be converted into different acid addition salts, for example by treatment of a salt of an inorganic acid, such as a hydrochloride, with a suitable metal salt, such as a sodium, barium or silver salt, of an acid, for example with silver acetate, in a suitable solvent in which an inorganic salt being formed, for example silver chloride, is insoluble and therefore separates from the reaction mixture.

Depending upon the procedure and the reaction conditions, compounds I having salt-forming properties can be obtained in free form or in the form of salts.

The compounds I, IV, V, VII, VIII, IX, XV and XVI may be in the form of one of the possible isomers or as a mixture thereof, for example according to the number of asymmetric carbon atoms and the absolute and relative configuration thereof, they may be in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and this is to be understood hereinbefore and hereinafter, even if stereochemical details are not specifically mentioned in each case.

Mixtures of diastereoisomers and mixtures of racemates of compounds I, IV, V, VII, VIII, IX, XV and XVI that are obtainable in accordance with the process depending upon the starting materials and procedures chosen, or by other means, can be separated into the pure diastereoisomers or racemates in known manner on the basis of the physicochemical differences between the constituents, for example by fractional crystallisation, distillation and/or chromatography.

Correspondingly obtainable mixtures of enantiomers, such as racemates, can be separated into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific immobilised enzymes, via the formation of inclusion compounds, for example using chiral crown ethers, in which case only one enantiomer is complexed.

Apart from by the separation of corresponding mixtures of isomers, it is possible according to the invention to obtain pure diastereoisomers or enantiomers also by generally known methods of diastereoselective or enantioselective synthesis, for example by carrying out the process according to the invention with starting materials having correspondingly suitable stereochemistry.

Advantageously, the biologically more active isomer, for example enantiomer or diastereoisomer, or mixture of isomers, for example mixture of enantiomers, will be isolated or synthesised, insofar as the individual components have different biological activity.

The compounds I, IV, V, VII, VIII, IX, XV and XVI can also be obtained in the form of their hydrates and/or may include other solvents, for example solvents used, where appropriate, for the crystallisation of compounds in solid form.

The invention relates to all those forms of the process according to which a compound obtainable as starting material or intermediate at any stage of the process is used as starting material and all or some of the remaining steps are carried out, or a starting material is used in the form of a derivative or a salt and/or its racemates or antipodes or, especially, is formed under the reaction conditions.

In the process of the present invention there are preferably used those starting materials and intermediates which result in the compounds I described at the beginning as being especially valuable.

The invention relates especially to the preparation processes described in Examples P1 to P39.

The invention relates also to those starting materials and intermediates used according to the invention for the preparation of the compounds I or the salts thereof, in each case in free form or in salt form, that are novel, to the use thereof and to processes for the preparation thereof.

In the area of pest control, the compounds I according to the invention are valuable preventive and/or curative active ingredients having a very advantageous biocidal spectrum even at low rates of concentration, while being well tolerated by warm-blooded animals, fish and plants. The compounds of the invention are effective against all or individual development stages of normally sensitive animal pests, but also of resistant animal pests, such as insects and representatives of the order Acarina. The insecticidal or acaricidal action of the compounds of the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

The mentioned animal pests include, for example:

of the order Lepidoptera, for example,

Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

of the order Coleoptera, for example,

Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogorma spp.;

of the order Orthoptera, for example,

Blatta spp., Blattella spp., Gryllotalpa spp., Leucophaea maderae, Locusta spp., Periplaneta spp. and Schistocerca spp.;

of the order Isoptera, for example,

Reticulitermes spp.;

of the order Psocoptera, for example,

Liposcelis spp.;

of the order Anoplura, for example,

Haematopinus spp., Linognathus spp., Pediculus spp., Pemphigus spp. and Phylloxera spp.;

of the order Mallophaga, for example,

Damalinea spp. and Trichodectes spp.;

of the order Thysanoptera, for example,

Frankliniella spp., Hercinothrips spp., Taeniothrips spp., *Thrips palmi, Thrips tabaci* and *Scirtothrips aurantii;* of the order Heteroptera, for example,

Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

of the order Homoptera, for example,

*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* of the order Hymenoptera, for example,

Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

of the order Diptera, for example,

Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;

of the order Siphonaptera, for example,

Ceratophyllus spp. and *Xenopsylla cheopis;* of the order Thysanura, for example,

*Lepisma saccharina*; and of the order Acarina, for example,

*Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp.

With the compounds according to the invention it is possible to control, i.e. to inhibit or destroy, pests of the mentioned type occurring especially on plants, especially on useful plants and ornamentals in agriculture, in horticulture and in forestry, or on parts of such plants, such as the fruit, blossom, leaves, stems, tubers or roots, while some of the parts of the plants which grow later are also protected against those pests.

Target crops are especially cereals, such as wheat, barley, rye, oats, rice, maize and sorghum; beet, such as sugar beet and fodder beet; fruit, such as pomes, stone fruit and soft fruit, such as apples, pears, plums, peaches, almonds, cherries, or berries, for example strawberries, raspberries or blackberries; leguminous plants, such as beans, lentils, peas and soybeans; oil plants, such as rape, mustard, poppy, olives, sunflowers, coconut, castor oil plants, cocoa beans and groundnuts; cucumber plants, such as marrows, cucumber and melons; fibre plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and tobacco, nuts, coffee, aubergines, sugar cane, tea, pepper, vines, hops, bananas and natural rubber plants, as well as ornamentals.

Further areas of use of the compounds according to the invention are the protection of stored goods and stocks and materials, and also in the hygiene sector, especially the protection of domestic animals and productive livestock against pests of the mentioned type.

The invention therefore relates also to pesticides, such as emulsifiable concentrates, suspension concentrates, directly sprayable or dilutable solutions, coatable pastes, dilute emulsions, wettable powders, soluble powders, dispersible powders, wettable powders, dusts, granules or encapsulations in polymer substances, comprising—at least—one of the compounds of the invention, the type of formulation being chosen in accordance with the intended objectives and prevailing circumstances.

The active ingredient is used in those compositions in pure form, a solid active ingredient, for example, in a specific particle size, or preferably together with—at least—one of the adjuvants customary in formulation technology, such as extenders, for example solvents or solid carriers, or surface-active compounds (surfactants).

Suitable solvents are, for example: optionally partially hydrogenated aromatic hydrocarbons, preferably the fractions of alkylbenzenes containing 8 to 12 carbon atoms, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and their ethers and esters, such as propylene glycol, dipropylene glycol ether, ethylene glycol or ethylene glycol monomethyl or monoethyl ether, ketones, such as cyclohexanone, isophorone or diacetone alcohol, strongly polar solvents, such as N-methylpyrrolid-2-one, dimethyl sulfoxide or N,N-dimethylformamide, water, vegetable oils or epoxidised vegetable oils, such as rape oil, castor oil, coconut oil or soybean oil or epoxidised rape oil, castor oil, coconut oil or soybean oil, and silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, such as pumice, broken brick, sepiolite or bentonite; and suitable nonsorbent carriers are calcite or sand. In addition, a great number of granulated materials of inorganic or organic nature can be used, especially dolomite or pulverised plant residues.

Depending on the nature of the compound to be formulated, suitable surface-active compounds are non-ionic, cationic and/or anionic surfactants or mixtures of surfactants having good emulsifying, dispersing and wetting properties. The surfactants listed below are to be regarded merely as examples; many more surfactants customarily employed in formulation technology and suitable for use according to the invention are described in the relevant literature.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates. Examples are stearyltrimethylammonium chloride and benzyldi(2-chloroethyl)ethylammonium bromide.

Both water-soluble soaps and water-soluble synthetic surface-active compounds are suitable anionic surfactants. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil; mention may also be made of fatty acid methyltaurin salts. More frequently, however, synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals; there may be mentioned by way of example the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

The compositions usually comprise 0.1 to 99%, preferably 0.1 to 95%, of active ingredient, and 1 to 99.9%, preferably 5 to 99.9%, of—at least—one solid or liquid adjuvant, it generally being possible for 0 to 25%, preferably 0.1 to 20%, of the composition to be surfactants (in each case percentages are by weight). Whereas commercial products will preferably be formulated as concentrates, the end user will normally employ dilute formulations which have considerably lower active ingredient concentrations. Preferred formulations have especially the following composition (throughout, percentages are by weight):

Emulsifiable Concentrates:

active ingredient: 1 to 90%, preferably 5 to 20%
surfactant: 1 to 30%, preferably 10 to 20%
solvent: 5 to 98%, preferably 70 to 85%

Dusts:

active ingredient: 0.1 to 10%, preferably 0.1 to 1%
solid carrier: 99.9 to 90%, preferably 99.9 to 99%

Suspension Concentrates:

active ingredient: 5 to 75%, preferably 10 to 50%
water: 94 to 24%, preferably 88 to 30%
surfactant: 1 to 40%, preferably 2 to 30%

Wettable Powders:

active ingredient: 0.5 to 90%, preferably 1 to 80%
surfactant: 0.5 to 20%, preferably 1 to 15%
solid carrier. 5 to 99%, preferably 15 to 98%

Granules:

active ingredient: 0.5 to 30%, preferably 3 to 15%
solid carrier: 99.5 to 70%, preferably 97 to 85%

The activity of the compositions according to the invention can be substantially broadened and adapted to prevailing circumstances by the addition of other insecticidal or acaricidal active ingredients. Examples of suitable additional insecticidal and acaricidal active ingredients include representatives of the following classes of compounds: organophosphorus compounds, nitrophenols and derivatives, formamidines, acylureas, carbamates, pyrethroids, nitroenamines and derivatives, pyrroles, thioureas and derivatives, chlorinated hydrocarbons, and Bacillus thuringiensis preparations. The compositions according to the invention may also comprise further solid or liquid adjuvants, such as stabilisers, for example vegetable oils or epoxidised vegetable oils (e.g. epoxidised coconut oil, rape oil or soybean oil), antifoams, for example silicone oil, preservatives, viscosity regulators, binders and/or tackifiers, as well as fertilisers or other active ingredients for obtaining special effects, for example bactericides, fungicides, nematicides, molluscicides or selective herbicides.

The compositions according to the invention are prepared in known manner, in the absence of adjuvants, for example by grinding, sieving and/or compressing a solid active ingredient or mixture of active ingredients, for example to a specific particle size, and in the presence of at least one adjuvant, for example by intimately mixing and/or grinding the active ingredient or mixture of active ingredients with the adjuvant(s). The invention relates also to that process for the preparation of the compositions according to the invention and to the use of the compounds I for the preparation of those compositions.

The invention relates also to the methods of application of the compositions, i.e. the methods of controlling pests of the mentioned type, such as spraying, atomising, dusting, coating, dressing, scattering or pouring, which are selected in accordance with the intended objectives and prevailing circumstances, and to the use of the compositions for controlling pests of the mentioned type. Typical rates of concentration are from 0.1 to 1000 ppm, preferably from 0.1 to 500 ppm, of active ingredient The rates of application per hectare are generally from 1 to 2000 g of active ingredient per hectare, especially from 10 to 1000 g/ha, preferably from 20 to 600 g/ha.

A preferred method of application in the area of plant protection is application to the foliage of the plants (foliar application), the number of applications and the rate of application depending on the risk of infestation by the pest in question. However, the active ingredient can also penetrate the plants through the roots (systemic action) if the locus of the plants is impregnated with a liquid formulation or if the active ingredient is incorporated in solid form into the locus of the plants, for example into the soil, e.g. in granular form (soil application). In paddy rice crops, such granules may be applied in metered amounts to the flooded rice field.

The compositions according to the invention are also suitable for protecting plant propagation material, e.g. seed, such as fruit, tubers or grains, or plant cuttings, from animal pests. The propagation material can be treated with the formulation before planting: seed, for example, can be dressed before being sown. The compounds of the invention can also be applied to grains (coating), either by impregnating the grains with a liquid formulation or by coating them with a solid formulation. The formulation can also be applied to the planting site when the propagation material is being planted, for example to the seed furrow during sowing. The invention relates also to those methods of treating plant propagation material and to the plant propagation material thus treated.

The following Examples serve to illustrate the invention. They do not limit the invention. Temperatures are given in degrees Celsius. In the Tables "Comp." stands for "Compound Number", "Me" for methyl, "Et" for ethyl, "nPr" for n-propyl, "iPr" for iso-propyl, "cPr" for cyclo-propyl, "tBu" for tert-butyl, "cHex" for cyclo-hexyl and "$C_2H_4$" for $CH_2CH_2$.

PREPARATION EXAMPLES

Example P1

4-Methyl-1-(pyridin-3-ylmethyleneamino)-imidazolidin-2-one (Compound 1.072 in Table 1)

At 50°, 2.1 g of hydrochloric acid are introduced into a solution of 3.1 g of (4methyl-2-oxo-imidazolidin-1-yl) acetamide in 40 ml of methanol. After one hour, 2.4 g of pyridine-3-carbaldehyde are added thereto. After 20 minutes, the reaction mixture is concentrated by evaporation and the residue is treated with tetrahydrofuran in a mixer. The crystals are filtered with suction and dried. 4.6 g of 4-methyl-1-(pyridin-3-ylmethyleneamino)-imidazolidin-2-one hydrochloride having a melting point of >240° are obtained. 2.3 ml of triethylamine are added to a suspension of 3.6 g of 4-methyl-1-(pyridin-3-ylmethyleneamino)-imidazolidin-2-one hydrochloride in 100 ml of tetrahydrofuran and the reaction mixture is heated under reflux for 5 minutes and then stirred for one hour. The triethylamine hydrochloride that has formed is filtered off with suction and 300 ml of hexane are added to the filtrate. The crystals that have precipitated are filtered with suction and dried. They are crystals of the title compound having a melting point of 189–195°.

Example P2

4-(Pyridin-3-ylmethyleneamino)-1,2,4-triazol-3-one (Compound 1.117 in Table 1)

A mixture of 4 g of 4-amino-1,2,4-triazol-3-one and 100 ml of alcohol is heated to the reflux temperature and 4.3 g of pyridine-3-carbaldehyde and 2 drops of 6N hydrochloric acid are added thereto. After 30 minutes under reflux the reaction mixture is cooled to 20°. The product that has precipitated is then filtered off with suction and dried under a high vacuum. 4.6 g of the title compound having a melting point of 264–265° are obtained.

Example P3

4-(Pyridin-3-ylmethyleneamino)-5-methyl-1,2,4-triazol-3-one (Compound 1.273 in Table 1)

A mixture of 5.7 g of 4-amino-5-methyl-1,2,4-triazol-3-one and 100 ml of alcohol is heated to the reflux temperature and 5.4 g of pyridine-3-carbaldehyde and 2 drops of 6N hydrochloric acid are added thereto. After 14 hours under reflux the reaction mixture is cooled to 20°. The product that has precipitated is then filtered off with suction and dried under a high vacuum. 3.4 g of the title compound having a melting point of 208–210° are obtained.

Example P4

2-Acetyl-4-(pyridin-3-ylmethyleneamino)-1,2,4-triazol-3-one (Compound 1.115 in Table 1)

2.4 g of acetyl chloride are added to a suspension of 3.8 g of 4-(pyridin-3-ylmethyleneamino)-1,2,4-triazol-3-one in 50 ml of pyridine. The resulting solution is stirred for 14 hours at 20° and then concentrated by evaporation. Water is added to the residue and extraction is carried out with chloroform. The organic phase is concentrated by evaporation and the residue is stirred with ether. The crystals are filtered off with suction and then dried under a high vacuum. 4 g of the title compound having a melting point of 164–166° are thus obtained.

Example P5

4-(Pyridin-3-ylmethyleneamino)-1,2,4triazol-3-one-2-carboxylic acid dimethylamide (Compound 1.116 in Table 1)

3.2 g of dimethylcarbamoyl chloride are added to a suspension of 3.8 g of 4-(pyridin-3-yl-methyleneamino)-1,2,4-triazol-3-one in 50 ml of pyridine. The resulting solution is stirred for 14 hours at 20° and then concentrated by evaporation. Water is added to the residue. The crystals that have precipitated are filtered off with suction and dried under a high vacuum. 3.6 g of crystals of the title compound having a melting point of 181–182° are obtained.

Example P6

5-Methyl-2-oxo-2,3-dihydro-1-(pyridin-3-ylmethyleneamino)-imidazole (Compound 1.121 in Table 1) and 4-methyl-2-oxo-2,3-dihydro-1-(pyridin-3-ylmethyleneamino)-imidazole (Compound 1.138 in Table 1)

A suspension of 18.4 g of 4-methyl-3-[(pyridin-3-ylmethylene)amino]-1-[(pyridin-3-yl-methylene)amino]-1,3-dihydroimidazol-2-one in 400 ml of tetrahydrofuran is heated to 60° and then 8.3 g of potassium tertiary butoxide are added thereto. When the foaming has subsided, the reaction mixture is cooled to 20° and poured onto 500 ml of saturated aqueous sodium chloride solution. The phases are separated and the aqueous phase is extracted with four times 150 ml of tetrahydrofuran. The organic phase is collected and washed twice with 150 ml of saturated aqueous sodium chloride solution each time, dried with magnesium sulfate and concentrated by evaporation. The residue is stirred with a small amount of methylene chloride. The crystals are filtered off with suction and dried. 3.4 g of crystals having a melting point of 168–177° are obtained. They are crystals of 4-methyl-2-oxo-2,3-dihydro-1-(pyridin-3-ylmethyleneamino)-imidazole. The mother liquor is concentrated by evaporation and chromatographed on silica gel using ethyl acetate. There are obtained on the one hand 3.8 g of yellowish crystals of 4-methyl-2-oxo-2,3-dihydro-1-(pyridin-3-ylmethyleneamino)-imidazole having a melting point of 177–179°, and on the other hand 0.7 g of 5-methyl-2-oxo-2,3-dihydro-1-(pyridin-3-yl-methyleneamino)-imidazole having a melting point of 200–202°.

Example P7

3,4-Dimethyl-1-(pyridin-3-ylmethyleneamino)-imidazolidin-2-one (Compound 1.074 in Table 1)

2.3 g of pyridine-3-carbaldehyde are added at room temperature to a solution of 3.6 g of 1-amino-3,4-dimethylimidazolidin-2-one hydrochloride in 25 ml of methanol. The solution is concentrated by evaporation and the residue is stirred with tetrahydrofuran. 4.6 g of 3,4-dimethyl-1-(pyridin-3-ylmethyleneamino)-imidazolidin-2-one hydrochloride having a melting point of 232–236° are obtained. 2.3 g of triethylamine are added to a suspension of 4.4 g of 3,4-dimethyl-1-(pyridin-3-ylmethyleneamino)-imidazolidin-2-one hydrochloride in 100 ml of tetrahydrofuran and after 20 minutes under reflux the reaction mixture is filtered while hot. 300 ml of hexane are added to the filtrate. The crystals that have precipitated are filtered off with suction and dried. 2.5 g of the title compound having a melting point of 126–129° are obtained.

Example P8

6-Methyl-4-(pyridin-3-ylmethyleneamino)-1,4,5,6-tetrahydro-1,2,4-triazin-3(2H)-one (Compound 1.291 in Table 1)

2.2 g of pyridine-3-carbaldehyde and 2 drops of sulfuric acid are added to a solution of 3 g of 4-amino-6-methyl-3-oxo-1,4,5,6-tetrahydro-1,2,4-triazine in 30 ml of ethanol. The reaction mixture is then maintained under reflux for 90 minutes and then the resulting suspension is cooled to 20°, filtered and dried. 4.1 g of the title compound having a melting point of 235–237° are obtained.

Example P9

6-Ethoxymethyl-4-(pyridin-3-ylmethyleneamino)-4,5-dihydro-2H-[1,2,4]-triazin-3-one (Compound 1.335 in Table 1)

2 g of (6-ethoxymethyl-3-oxo-2,5-dihydro-3H-[1,3,4]triazin-4-yl)-thiocarbamic acid O-methyl ester (Comp. 9.073) are placed in a round-bottomed flask, 6 ml of sulfuric acid are added thereto and the reaction mixture is then heated to 60°. After one hour the reaction mixture is poured onto 50 g of ice and adjusted to pH 10 with concentrated sodium hydroxide solution and then to pH 4 with hydrochloric acid. 1.1 g of 3-pyridine aldehyde is then added thereto. After 30 minutes the reaction mixture is extracted three times with 50 ml of methylene chloride and concentrated by evaporation. The residue is stirred with ether/isopropanol. 0.8 g of the title compound in the form of yellowish crystals having a melting point of 156–158° is thus obtained.

Example P10

The other compounds listed in Tables 1, 1a and 1b can also be prepared in a manner analogous to that described in Examples P1 to P9.

TABLE 1

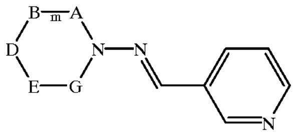

| Comp. | A | m | B | D | E | G |
|---|---|---|---|---|---|---|
| 1.001 | CS | 0 | | NH | NH | CS |
| 1.002 | CS | 0 | | NH | NH | CO |
| 1.003 | CO | 1 | —CMe= | N= | NH | CS |
| 1.004 | CO | 1 | $C(C_2H_4iPr)$= | N= | NH | CS |
| 1.005 | CO | 1 | $C(CH_2iPr)$= | N= | NH | CS |
| 1.006 | CO | 1 | CtBu= | N= | NH | CS |
| 1.007 | CO | 1 | CtBu= | N= | NH | CO |
| 1.008 | CO | 1 | CcPr= | N= | NH | CS |
| 1.009 | CO | 1 | CcHex= | N= | NH | CS |
| 1.010 | CO | 1 | $NCH_2$-cHex | CO | NH | CO |
| 1.011 | CO | 1 | $CH_2$ | CO | NH | CO |
| 1.012 | CO | 1 | $CH_2$ | $CH_2$ | NH | CO |
| 1.013 | CO | 1 | $CH_2$ | $CMe_2$ | NH | CO |
| 1.014 | CO | 1 | CH= | CMe= | NH | CO |
| 1.015 | CO | 1 | CH= | N= | NH | CS |
| 1.016 | CO | 1 | CH= | $CCF_3$= | NH | CNH |
| 1.017 | CO | 1 | $CMe_2$ | CO | NH | CO |
| 1.018 | CO | 1 | $CMe_2$ | $CH_2$ | NH | CO |
| 1.019 | CO | 1 | CMe= | N= | NH | CO |
| 1.020 | CO | 1 | CtBu= | N= | $NC_2H_4F$ | CS |
| 1.021 | CO | 1 | CEt= | N= | NH | CS |
| 1.022 | CO | 0 | | CO | NH | CO |
| 1.023 | CO | 0 | | NH | NH | CO |
| 1.024 | CO | 0 | | $CH_2$ | S | CS |
| 1.025 | CO | 0 | | $CHCH_2COOMe$ | NH | CS |
| 1.026 | CO | 0 | | $CHC_2H_4COOMe$ | NH | CS |
| 1.027 | CO | 0 | | NH | NH | CO |
| 1.028 | CO | 0 | | $CMeCH{=}CMe_2$ | NH | CO |
| 1.029 | CO | 0 | | $CMeCH_2CMe_2$ | NH | CO |
| 1.030 | CO | 0 | | $CH_2$ | NH | CS |
| 1.031 | CO | 0 | | $CMe_2$ | NH | CO |
| 1.032 | $CH_2$ | 0 | | CO | NMe | CS |
| 1.033 | $CH_2$ | 0 | | CO | NiPr | CS |

TABLE 1-continued

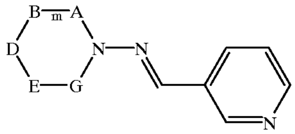

| Comp. | A | m | B | D | E | G |
|---|---|---|---|---|---|---|
| 1.034 | $CH_2$ | 0 | | CO | NEt | CS |
| 1.035 | $CH_2$ | 0 | | CO | NH | CO |
| 1.036 | $CH_2$ | 0 | | CO | NH | CS |
| 1.037 | $CH_2$ | 1 | $CMe_2$ | CO | NH | CO |
| 1.038 | $CH_2$ | 0 | | CO | NH | CO |
| 1.039 | $CH_2$ | 1 | $CH_2$ | CO | NH | CO |
| 1.040 | $CH_2$ | 0 | | $CH_2$ | O | CO |
| 1.041 | $CH_2$ | 0 | | $CH_2$ | NH | CO |
| 1.042 | $CH_2$ | 0 | | $CH_2$ | NH | CS |
| 1.043 | $CH_2$ | 0 | | $CH_2$ | $CH_2$ | CO |
| 1.044 | $CH_2$ | 0 | | $CH_2$ | NH | CO |
| 1.045 | $CH_2$ | 0 | | $CH_2$ | NH | CO |
| 1.046 | $CH_2$ | 1 | $CH_2$ | $CH_2$ | NH | CO |
| 1.047 | $CH_2$ | 1 | $CMe_2$ | $CH_2$ | NH | CO |
| 1.048 | $CH_2$ | 1 | $CMe_2$ | $CH_2$ | NH | CO |
| 1.049 | $CH_2$ | 1 | $C(OMe)_2$ | $CH_2$ | NH | CO |
| 1.050 | $CH_2$ | 1 | $C(OEt)_2$ | $CH_2$ | NH | CO |
| 1.051 | $CH_2$ | 1 | $C(CH_2OH)_2$ | $CH_2$ | NH | CO |
| 1.052 | $CH_2$ | 1 | CO | $CH_2$ | NH | CO |
| 1.053 | $CH_2$ | 1 | CHOH | $CH_2$ | NH | CO |
| 1.054 | $CH_2$ | 1 | O | $CH_2$ | NH | CO |
| 1.055 | $CH_2$ | 1 | NMe | $CH_2$ | NH | CO |
| 1.056 | $CH_2$ | 0 | | $CH_2$ | NH | CO |
| 1.057 | $CH_2$ | 0 | | $CH_2$ | NMe | CO |
| 1.058 | $CH_2$ | 0 | | $CH_2$ | NCOMe | CO |
| 1.059 | $CH_2$ | 0 | | $CH_2$ | NCOEt | CO |
| 1.060 | $CH_2$ | 0 | | $CH_2$ | NCO-nPr | CO |
| 1.061 | $CH_2$ | 0 | | $CH_2$ | $NCOCH_2OMe$ | CO |
| 1.062 | $CH_2$ | 0 | | $CH_2$ | $NCOCHMe_2$ | CO |
| 1.063 | $CH_2$ | 1 | $CH_2$ | $CH_2$ | NH | CO |
| 1.064 | $CH_2$ | 1 | $CH_2$ | $CH_2$ | NH | CO |
| 1.065 | $CH_2$ | 1 | $CH_2$ | $CH_2$ | NMe | CO |
| 1.066 | $CH_2$ | 1 | $CH_2$ | $CH_2$ | NCOMe | CO |
| 1.067 | $CH_2$ | 1 | $CH_2$ | $CH_2$ | NCOEt | CO |
| 1.068 | $CH_2$ | 1 | $CH_2$ | $CH_2$ | NCO-nPr | CO |
| 1.069 | $CH_2$ | 1 | $CH_2$ | $CH_2$ | $NCOCH_2OMe$ | CO |
| 1.070 | $CH_2$ | 1 | $CH_2$ | $CH_2$ | $NCOCHMe_2$ | CO |
| 1.071 | $CH_2$ | 1 | CH= | CH= | NH | CO |
| 1.072 | $CH_2$ | 0 | | CHMe | NH | CO |
| 1.013 | $CH_2$ | 0 | | CHMe | NH | CO |
| 1.074 | $CH_2$ | 0 | | CHMe | NMe | CO |
| 1.075 | $CH_2$ | 0 | | CHMe | NCOMe | CO |
| 1.076 | $CH_2$ | 0 | | CHMe | NCOEt | CO |
| 1.077 | $CH_2$ | 0 | | CHMe | NCO-nPr | CO |
| 1.078 | $CH_2$ | 0 | | CHMe | $NCOCH_2OMe$ | CO |
| 1.079 | $CH_2$ | 0 | | CHMe | $NCOCHMe_2$ | CO |
| 1.080 | $CH_2$ | 1 | $CH_2$ | CHMe | NH | CO |
| 1.081 | $CH_2$ | 1 | $CH_2$ | CHMe | NH | CO |
| 1.082 | $CH_2$ | 1 | $CH_2$ | CHMe | NMe | CO |
| 1.083 | $CH_2$ | 1 | $CH_2$ | CHMe | NCOMe | CO |
| 1.084 | $CH_2$ | 1 | $CH_2$ | CHMe | NCOEt | CO |
| 1.085 | $CH_2$ | 1 | $CH_2$ | CHMe | NCO-nPr | CO |
| 1.086 | $CH_2$ | 1 | $CH_2$ | CHMe | $NCOCH_2OMe$ | CO |
| 1.087 | $CH_2$ | 1 | $CH_2$ | CHMe | $NCOCHMe_2$ | CO |
| 1.088 | $CH_2$ | 0 | | $CHCH_2OMe$ | NH | CO |
| 1.089 | $CH_2$ | 1 | $CH_2$ | $CHCH_2OMe$ | NH | CO |
| 1.090 | $CH_2$ | 0 | | CH-tBu | NH | CO |
| 1.091 | $CH_2$ | 1 | $CH_2$ | CH-tBu | NH | CO |
| 1.092 | $CH_2$ | 0 | | CH-iPr | NH | CO |
| 1.093 | $CH_2$ | 1 | $CH_2$ | CH-iPr | NH | CO |
| 1.094 | $CH_2$ | 0 | | CH-cPr | NH | CO |
| 1.095 | $CH_2$ | 1 | $CH_2$ | CH-cPr | NH | CO |
| 1.096 | $CH_2$ | 0 | | CHEt | NH | CO |
| 1.098 | $CH_2$ | 0 | | CHEt | NMe | CO |
| 1.099 | $CH_2$ | 0 | | CHEt | NCOMe | CO |
| 1.100 | $CH_2$ | 0 | | CHEt | NCOEt | CO |
| 1.101 | $CH_2$ | 0 | | CHEt | NCO-nPr | CO |
| 1.102 | $CH_2$ | 0 | | CHEt | $NCOCH_2OMe$ | CO |
| 1.103 | $CH_2$ | 0 | | CHEt | $NCOCHMe_2$ | CO |
| 1.104 | $CH_2$ | 1 | $CH_2$ | CHEt | NH | CO |

TABLE 1-continued

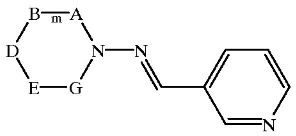

| Comp. | A | m | B | D | E | G |
|---|---|---|---|---|---|---|
| 1.106 | $CH_2$ | 1 | $CH_2$ | CHEt | NMe | CO |
| 1.107 | $CH_2$ | 1 | $CH_2$ | CHEt | NCOMe | CO |
| 1.108 | $CH_2$ | 1 | $CH_2$ | CHEt | NCOEt | CO |
| 1.109 | $CH_2$ | 1 | $CH_2$ | CHEt | NCO-nPr | CO |
| 1.110 | $CH_2$ | 1 | $CH_2$ | CHEt | $NCOCH_2OMe$ | CO |
| 1.111 | $CH_2$ | 1 | $CH_2$ | CHEt | $NCOCHMe_2$ | CO |
| 1.112 | $CH_2$ | 1 | CMe= | CH= | NH | CO |
| 1.113 | $CH_2$ | 1 | CEt= | CH= | NH | CO |
| 1.114 | $CH_2$ | 1 | CH= | C(t-Bu)= | NMe | CO |
| 1.115 | CH= | 0 | | N= | $NCOCH_3$ | CO |
| 1.116 | CH= | 0 | | N= | $NCONMe_2$ | CNH |
| 1.117 | CH= | 0 | | N= | NH | CO |
| 1.118 | CH= | 1 | CH= | NH | NH | CO |
| 1.119 | CH= | 1 | CMe= | $CH_2$ | NH | CO |
| 1.120 | CH= | 1 | CEt= | $CH_2$ | NH | CO |
| 1.121 | CH= | 0 | | CMe= | NH | CO |
| 1.122 | CH= | 1 | CH= | CHMe | NH | CO |
| 1.123 | CH= | 0 | | CtBu= | NH | CO |
| 1.124 | CHMe | 0 | | $CH_2$ | NH | CO |
| 1.125 | CHMe | 0 | | $CH_2$ | NMe | CO |
| 1.126 | CHMe | 0 | | $CH_2$ | NCOMe | CO |
| 1.127 | CHMe | 0 | | $CH_2$ | NCOEt | CO |
| 1.128 | CHMe | 0 | | $CH_2$ | NCOnPr | CO |
| 1.129 | CHMe | 0 | | $CH_2$ | $NCOCH_2OMe$ | CO |
| 1.130 | CHMe | 0 | | $CH_2$ | $NCOCHMe_2$ | CO |
| 1.131 | CHMe | 1 | $CH_2$ | $CH_2$ | NH | CO |
| 1.132 | CHMe | 1 | $CH_2$ | $CH_2$ | NMe | CO |
| 1.133 | CHMe | 1 | $CH_2$ | $CH_2$ | NCOMe | CO |
| 1.134 | CHMe | 1 | $CH_2$ | $CH_2$ | NCOEt | CO |
| 1.135 | CHMe | 1 | $CH_2$ | $CH_2$ | NCOnPr | CO |
| 1.136 | CHMe | 1 | $CH_2$ | $CH_2$ | $NCOCH_2OMe$ | CO |
| 1.137 | CHMe | 1 | $CH_2$ | $CH_2$ | $NCOCHMe_2$ | CO |
| 1.138 | CMe= | 0 | | C= | $NCH_3$ | CO |
| 1.139 | CHMe | 1 | CH= | CH= | NH | CO |
| 1.140 | CHMe | 0 | | CHMe | NH | CO |
| 1.141 | CHMe | 0 | | CHMe | NMe | CO |
| 1.142 | CHMe | 0 | | CHMe | NCOMe | CO |
| 1.143 | CHMe | 0 | | CHMe | NCOEt | CO |
| 1.144 | CHMe | 0 | | CHMe | NCOnPr | CO |
| 1.145 | CHMe | 0 | | CHMe | $NCOCH_2OMe$ | CO |
| 1.146 | CHMe | 0 | | CHMe | $NCOCHMe_2$ | CO |
| 1.147 | CHMe | 1 | $CH_2$ | CHMe | NH | CO |
| 1.148 | CHMe | 1 | $CH_2$ | CHMe | NMe | CO |
| 1.149 | CHMe | 1 | $CH_2$ | CHMe | NCOMe | CO |
| 1.150 | CHMe | 1 | $CH_2$ | CHMe | NCOEt | CO |
| 1.151 | CHMe | 1 | $CH_2$ | CHMe | NCOnPr | CO |
| 1.152 | CHMe | 1 | $CH_2$ | CHMe | $NCOCH_2OMe$ | CO |
| 1.153 | CHMe | 1 | $CH_2$ | CHMe | $NCOCHMe_2$ | CO |
| 1.154 | CHMe | 0 | | CHEt | NH | CO |
| 1.155 | CHMe | 0 | | CHEt | NMe | CO |
| 1.156 | CHMe | 0 | | CHEt | NCOMe | CO |
| 1.157 | CHMe | 0 | | CHEt | NCOEt | CO |
| 1.158 | CHMe | 0 | | CHEt | NCOnPr | CO |
| 1.159 | CHMe | 0 | | CHEt | $NCOCH_2OMe$ | CO |
| 1.160 | CHMe | 0 | | CHEt | $NCOCHMe_2$ | CO |
| 1.161 | CHMe | 1 | $CH_2$ | CHEt | NH | CO |
| 1.162 | CHMe | 1 | $CH_2$ | CHEt | NMe | CO |
| 1.163 | CHMe | 1 | $CH_2$ | CHEt | NCOMe | CO |
| 1.164 | CHMe | 1 | $CH_2$ | CHEt | NCOEt | CO |
| 1.165 | CHMe | 1 | $CH_2$ | CHEt | NCOnPr | CO |
| 1.166 | CHMe | 1 | $CH_2$ | CHEt | $NCOCH_2OMe$ | CO |
| 1.167 | CHMe | 1 | $CH_2$ | CHEt | $NCOCHMe_2$ | CO |
| 1.168 | $CHCH_2OMe$ | 0 | | $CH_2$ | NH | CO |
| 1.169 | $CHCH_2OMe$ | 1 | $CH_2$ | $CH_2$ | NH | CO |
| 1.170 | CHtBu | 0 | | $CH_2$ | NH | CO |
| 1.171 | CHtBu | 1 | $CH_2$ | $CH_2$ | NH | CO |
| 1.172 | CHiPr | 0 | | $CH_2$ | NH | CO |
| 1.173 | CHiPr | 1 | $CH_2$ | $CH_2$ | NH | CO |
| 1.174 | CHiPr | 0 | | $CH_2$ | NH | CO |
| 1.175 | CHiPr | 0 | | $CH_2$ | NMe | CO |

TABLE 1-continued

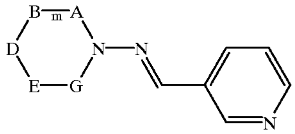

| Comp. | A | m | B | D | E | G |
|---|---|---|---|---|---|---|
| 1.176 | CHiPr | 0 | | $CH_2$ | NCOMe | CO |
| 1.177 | CHiPr | 0 | | $CH_2$ | NCOEt | CO |
| 1.178 | CHiPr | 0 | | $CH_2$ | NCOnPr | CO |
| 1.179 | CHiPr | 0 | | $CH_2$ | $NCOCH_2OMe$ | CO |
| 1.180 | CHiPr | 0 | | $CH_2$ | $NCOCHMe_2$ | CO |
| 1.181 | CHiPr | 1 | $CH_2$ | $CH_2$ | NH | CO |
| 1.182 | CHiPr | 1 | $CH_2$ | $CH_2$ | NMe | CO |
| 1.183 | CHiPr | 1 | $CH_2$ | $CH_2$ | NCOMe | CO |
| 1.184 | CHiPr | 1 | $CH_2$ | $CH_2$ | NCOEt | CO |
| 1.185 | CHiPr | 1 | $CH_2$ | $CH_2$ | NCO-nPr | CO |
| 1.186 | CHiPr | 1 | $CH_2$ | $CH_2$ | $NCOCH_2OMe$ | CO |
| 1.187 | CHiPr | 1 | $CH_2$ | $CH_2$ | $NCOCHMe_2$ | CO |
| 1.188 | CHiPr | 0 | | CHMe | NH | CO |
| 1.189 | CHiPr | 0 | | CHMe | NMe | CO |
| 1.190 | CHiPr | 0 | | CHMe | NCOMe | CO |
| 1.191 | CHiPr | 0 | | CHMe | NCOEt | CO |
| 1.192 | CHiPr | 0 | | CHMe | NCOnPr | CO |
| 1.193 | CHiPr | 0 | | CHMe | $NCOCH_2OMe$ | CO |
| 1.194 | CHiPr | 0 | | CHMe | $NCOCHMe_2$ | CO |
| 1.195 | CHiPr | 1 | $CH_2$ | CHMe | NH | CO |
| 1.196 | CHiPr | 1 | $CH_2$ | CHMe | NMe | CO |
| 1.197 | CHiPr | 1 | $CH_2$ | CHMe | NCOMe | CO |
| 1.198 | CHiPr | 1 | $CH_2$ | CHMe | NCOEt | CO |
| 1.199 | CHiPr | 1 | $CH_2$ | CHMe | NCOnPr | CO |
| 1.200 | CHiPr | 1 | $CH_2$ | CHMe | $NCOCH_2OMe$ | CO |
| 1.201 | CHiPr | 1 | $CH_2$ | CHMe | $NCOCHMe_2$ | CO |
| 1.202 | CHiPr | 0 | | CHEt | NH | CO |
| 1.203 | CHiPr | 0 | | CHEt | NMe | CO |
| 1.204 | CHiPr | 0 | | CHEt | NCOMe | CO |
| 1.205 | CHiPr | 0 | | CHEt | NCOEt | CO |
| 1.206 | CHiPr | 0 | | CHEt | NCOnPr | CO |
| 1.207 | CHiPr | 0 | | CHEt | $NCOCH_2OMe$ | CO |
| 1.208 | CHiPr | 0 | | CHEt | $NCOCHMe_2$ | CO |
| 1.209 | CHiPr | 1 | $CH_2$ | CHEt | NH | CO |
| 1.210 | CHiPr | 1 | $CH_2$ | CHEt | NMe | CO |
| 1.211 | CHiPr | 1 | $CH_2$ | CHEt | NCOMe | CO |
| 1.212 | CHiPr | 1 | $CH_2$ | CHEt | NCOEt | CO |
| 1.213 | CHiPr | 1 | $CH_2$ | CHEt | NCOnPr | CO |
| 1.214 | CHiPr | 1 | $CH_2$ | CHEt | $NCOCH_2OMe$ | CO |
| 1.215 | CHiPr | 1 | $CH_2$ | CHEt | $NCOCHMe_2$ | CO |
| 1.216 | CHcPr | 0 | | $CH_2$ | NH | CO |
| 1.217 | CHcPr | 1 | $CH_2$ | $CH_2$ | NH | CO |
| 1.218 | CHEt | 0 | | $CH_2$ | NH | CO |
| 1.219 | CHEt | 1 | $CH_2$ | $CH_2$ | NH | CO |
| 1.220 | CHEt | 0 | | $CH_2$ | NH | CO |
| 1.221 | CHEt | 0 | | $CH_2$ | NMe | CO |
| 1.222 | CHEt | 0 | | $CH_2$ | NCOMe | CO |
| 1.223 | CHEt | 0 | | $CH_2$ | NCOEt | CO |
| 1.224 | CHEt | 0 | | $CH_2$ | NCOnPr | CO |
| 1.225 | CHEt | 0 | | $CH_2$ | $NCOCH_2OMe$ | CO |
| 1.226 | CHEt | 0 | | $CH_2$ | $NCOCHMe_2$ | CO |
| 1.227 | CHEt | 1 | $CH_2$ | $CH_2$ | NH | CO |
| 1.228 | CHEt | 1 | $CH_2$ | $CH_2$ | NMe | CO |
| 1.229 | CHEt | 1 | $CH_2$ | $CH_2$ | NCOMe | CO |
| 1.230 | CHEt | 1 | $CH_2$ | $CH_2$ | NCOEt | CO |
| 1.231 | CHEt | 1 | $CH_2$ | $CH_2$ | NCOnPr | CO |
| 1.232 | CHEt | 1 | $CH_2$ | $CH_2$ | $NCOCH_2OMe$ | CO |
| 1.233 | CHEt | 1 | $CH_2$ | $CH_2$ | $NCOCHMe_2$ | CO |
| 1.234 | CHEt | 0 | | CHMe | NH | CO |
| 1.235 | CHEt | 0 | | CHMe | NMe | CO |
| 1.236 | CHEt | 0 | | CHMe | NCOMe | CO |
| 1.237 | CHEt | 0 | | CHMe | NCOEt | CO |
| 1.238 | CHEt | 0 | | CHMe | NCO-nPr | CO |
| 1.239 | CHEt | 0 | | CHMe | $NCOCH_2OMe$ | CO |
| 1.240 | CHEt | 0 | | CHMe | $NCOCHMe_2$ | CO |
| 1.241 | CHEt | 1 | $CH_2$ | CHMe | NH | CO |
| 1.242 | CHEt | 1 | $CH_2$ | CHMe | NMe | CO |
| 1.243 | CHEt | 1 | $CH_2$ | CHMe | NCOMe | CO |
| 1.244 | CHEt | 1 | $CH_2$ | CHMe | NCOEt | CO |
| 1.245 | CHEt | 1 | $CH_2$ | CHMe | NCOnPr | CO |

TABLE 1-continued

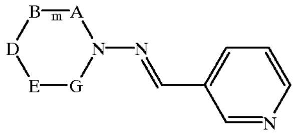

| Comp. | A | m B | D | E | G |
|---|---|---|---|---|---|
| 1.246 | CHEt | 1 $CH_2$ | CHMe | $NCOCH_2OMe$ | CO |
| 1.247 | CHEt | 1 $CH_2$ | CHMe | $NCOCHMe_2$ | CO |
| 1.248 | CHEt | 0 | CHEt | NH | CO |
| 1.249 | CHEt | 0 | CHEt | NMe | CO |
| 1.250 | CHEt | 0 | CHEt | NCOMe | CO |
| 1.251 | CHEt | 0 | CHEt | NCOEt | CO |
| 1.252 | CHEt | 0 | CHEt | NCOnPr | CO |
| 1.253 | CHEt | 0 | CHEt | $NCOCH_2OMe$ | CO |
| 1.254 | CHEt | 0 | CHEt | $NCOCHMe_2$ | CO |
| 1.255 | CHEt | 1 $CH_2$ | CHEt | NH | CO |
| 1.256 | CHEt | 1 $CH_2$ | CHEt | NMe | CO |
| 1.257 | CHEt | 1 $CH_2$ | CHEt | NCOMe | CO |
| 1.258 | CHEt | 1 $CH_2$ | CHEt | NCOEt | CO |
| 1.259 | CHEt | 1 $CH_2$ | CHEt | NCOnPr | CO |
| 1.260 | CHEt | 1 $CH_2$ | CHEt | $NCOCH_2OMe$ | CO |
| 1.261 | CHEt | 1 $CH_2$ | CHEt | $NCOCHMe_2$ | CO |
| 1.262 | CSMe= | 1 N= | CO | NMe | CO |
| 1.263 | CNHCOOEt= | 0 | N= | NH | CS |
| 1.264 | CNHCOOMe= | 0 | N= | NH | CS |
| 1.265 | CNHMe= | 1 N= | CO | NMe | CO |
| 1.266 | $CMe_2$ | 0 | CO | NH | CO |
| 1.267 | $CMe_2$ | 1 $CH_2$ | CO | NH | CO |
| 1.268 | $CMe_2$ | 0 | $CH_2$ | NH | CO |
| 1.269 | $CMe_2$ | 1 $CH_2$ | $CH_2$ | NH | CO |
| 1.270 | CMe= | 0 | CCOOEt= | S | CNH |
| 1.271 | CMe= | 0 | N= | NH | CS |
| 1.273 | CMe= | 0 | N= | NH | CO |
| 1.274 | CMe= | 1 CH= | NH | NH | CO |
| 1.275 | CMe= | 0 | CH= | S | CNH |
| 1.276 | CHMe | 0 | $CH_2$ | NH | CO |
| 1.277 | CMe= | 1 CH= | $CH_2$ | NH | CO |
| 1.278 | $CCH_2OMe$= | 0 | N= | NH | CS |
| 1.279 | $CCH_2OEt$= | 0 | N= | NH | CS |
| 1.280 | $CCH_2iPr$= | 0 | N= | NH | CS |
| 1.281 | $CCF_3$= | 0 | N= | NH | CS |
| 1.282 | CcHex= | 0 | N= | NH | CS |
| 1.283 | CiPr= | 0 | N= | NH | CS |
| 1.284 | CcPr= | 0 | N= | NH | CS |
| 1.285 | CEt= | 0 | N= | NH | CS |
| 1.286 | CEt= | 0 | N= | NH | CO |
| 1.287 | $CC_2F_5$= | 0 | N= | NH | CS |
| 1.288 | CBr= | 0 | N= | NH | CS |
| 1.289 | C(=NH) | 0 | $CMe_2$ | NH | CO |
| 1.290 | C(=NH) | 1 CH= | CMe= | NH | CO |
| 1.291 | $CH_2$ | 1 CHMe | NH | NH | CO |
| 1.292 | $CH_2$ | 1 CHEt | NH | NH | CO |
| 1.293 | $CH_2$ | 1 CHcPr | NH | NH | CO |
| 1.294 | $CH_2$ | 1 CHtBu | NH | NH | CO |
| 1.295 | $CH_2$ | 1 $CHCH_2OMe$ | NH | NH | CO |
| 1.296 | CHMe | 1 CHMe | NH | NH | CO |
| 1.297 | CHMe | 1 CHEt | NH | NH | CO |
| 1.298 | CHMe | 1 CHcPr | NH | NH | CO |
| 1.299 | CHMe | 1 CHtBu | NH | NH | CO |
| 1.300 | CHMe | 1 $CHCH_2OMe$ | NH | NH | CO |
| 1.301 | $CMe_2$ | 1 CHMe | NH | NH | CO |
| 1.302 | $CMe_2$ | 1 CHEt | NH | NH | CO |
| 1.303 | $CMe_2$ | 1 CHcPr | NH | NH | CO |
| 1.304 | $CMe_2$ | 1 CHtBu | NH | NH | CO |
| 1.305 | $CMe_2$ | 1 $CHCH_2OMe$ | NH | NH | CO |
| 1.306 | $CH_2$ | 1 CHMe | NCOMe | NCOMe | CO |
| 1.307 | $CH_2$ | 1 CHMe | $NCOCH_2OMe$ | $NCOCH_2OMe$ | CO |
| 1.308 | $CH_2$ | 1 CHMe | NCO-cPr | NCO-cPr | CO |
| 1.309 | $CH_2$ | 1 CHMe | $NCOCH_2Cl$ | $NCOCH_2C1$ | CO |
| 1.310 | $CH_2$ | 1 CHMe | NCOEt | NCOEt | CO |
| 1.311 | $CH_2$ | 1 CHMe | $NCOCHMe_2$ | $NCOCHMe_2$ | CO |
| 1.312 | $CH_2$ | 1 CHMe | NCOOEt | NCOOEt | CO |
| 1.313 | $CH_2$ | 1 CHMe | NCOMe | NH | CO |
| 1.314 | $CH_2$ | 1 CHMe | $NCOCH_2OMe$ | NH | CO |
| 1.315 | $CH_2$ | 1 CHMe | NCO-cPr | NH | CO |
| 1.316 | $CH_2$ | 1 CHMe | $NCOCH_2C1$ | NH | CO |

TABLE 1-continued

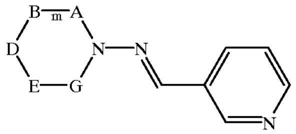

| Comp. | A | m | B | D | E | G |
|---|---|---|---|---|---|---|
| 1.317 | $CH_2$ | 1 | CHMe | NCOEt | NH | CO |
| 1.318 | $CH_2$ | 1 | CHMe | $NCOCHMe_2$ | NH | CO |
| 1.319 | $CH_2$ | 1 | CHMe | NCOOEt | NH | CO |
| 1.320 | CH═ | 0 | | CMe═ | N(—N═CH-3-pyridinyl) | CO |
| 1.321 | $CH_2$ | 0 | | C(Me)(OH) | N(—N═CH-3-pyridinyl) | CO |
| 1.322 | CH═ | 0 | | N═ | NCONHMe | CO |
| 1.323 | CH═ | 0 | | N═ | NCOiPr | CO |
| 1.324 | CH═ | 0 | | N═ | NCOOEt | CO |
| 1.325 | CH═ | 0 | | N═ | NCOtBu | CO |
| 1.326 | $CH_2$ | 1 | CO | NH | NMe | CO |
| 1.327 | CO | 0 | | $CH_2$ | NNHCOMe | CO |
| 1.328 | $CH_2$ | 0 | | C(OH)Me | NNHEt | CO |
| 1.329 | CMe═ | 0 | | CH═ | $NNH_2$ | CO |
| 1.330 | CO | 0 | | CHMe | NiPr | CO |
| 1.331 | $CH_2$ | 1 | $C(CH_2OCOMe)$ | N═ | NH | CO |
| 1.332 | CO | 1 | CHMe | NH | NH | CO |
| 1.333 | $CH_2$ | 1 | C(Z1[a])═ | N═ | NH | CO |
| 1.334 | $CH_2$ | 1 | C(Z2[a])═ | N═ | NH | CO |
| 1.335 | $CH_2$ | 1 | $C(CH_2OEt)$═ | N═ | NH | CO |

[a]Z1: $CH_2SC_2H_4COOMe$; Z2: $CH_2SC_2H_4COOH$

TABLE 1a melting points of compounds from Table 1

| Comp. | m.p.(°) |
|---|---|
| 1.019 | 205–207 |
| 1.041 | 193–194 |
| 1.046 | 172 |
| 1.058 | 210–212 |
| 1.063 | 170–172 |
| 1.066 | 151–153 |
| 1.072 | 189–195 |
| 1.074 | 126–129 |
| 1.075 | 124–126 |
| 1.080 | solid |
| 1.115 | 164–166 |
| 1.116 | 181–182 |
| 1.117 | 264–265 |
| 1.121 | 177–179 |
| 1.123 | 255–256 |
| 1.125 | 128–130 |
| 1.138 | 200–202 |
| 1.273 | 208–210 |
| 1.276 | 128–130 |
| 1.291 | 235–237 |
| 1.306 | 176–178 |
| 1.307 | 127–129 |
| 1.308 | 146–148 |
| 1.313 | 185–186 |

TABLE 1a-continued melting points of compounds from Table 1

| Comp. | m.p.(°) |
|---|---|
| 1.315 | 189–192 |
| 1.320 | 172–174 |
| 1.321 | 175–182 |
| 1.322 | 207–208 |
| 1.323 | 145–146 |
| 1.324 | 165–166 |
| 1.325 | 170–172 |
| 1.326 | 217–220 |
| 1.327 | 180–182 |
| 1.328 | 102–117 |
| 1.329 | 164–165 |
| 1.330 | resin |
| 1.331 | 190–200 |
| 1.332 | 161–162 |
| 1.333 | 118 |
| 1.334 | 237 |
| 1.335 | 156–158 |

TABLE 1b

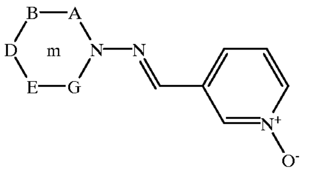

| Comp. | A | m | B | D | E | G |
|---|---|---|---|---|---|---|
| b.001 | CS | 0 | | NH | NH | CS |
| b.002 | CS | 0 | | NH | NH | CO |
| b.003 | CO | 1 | —CMe= | N= | NH | CS |
| b.004 | CO | 1 | $C(C_2H_4iPr)$= | N= | NH | CS |
| b.005 | CO | 1 | $C(CH_2iPr)$= | N= | NH | CS |
| b.006 | CO | 1 | CtBu= | N= | NH | CS |
| b.007 | CO | 1 | CtBu= | N= | NH | CO |
| b.008 | CO | 1 | CcPr= | N= | NH | CS |
| b.009 | CO | 1 | CcHex= | N= | NH | CS |
| b.010 | CO | 1 | $NCH_2$-cHex | CO | NH | CO |
| b.011 | CO | 1 | $CH_2$ | CO | NH | CO |
| b.012 | CO | 1 | $CH_2$ | $CH_2$ | NH | CO |
| b.013 | CO | 1 | $CH_2$ | $CMe_2$ | NH | CO |
| b.014 | CO | 1 | CH= | CMe= | NH | CO |
| b.015 | CO | 1 | CH= | N= | NH | CS |
| b.016 | CO | 1 | CH= | $CCF_3$= | NH | CNH |
| b.017 | CO | 1 | $CMe_2$ | CO | NH | CO |
| b.018 | CO | 1 | $CMe_2$ | $CH_2$ | NH | CO |
| b.019 | CO | 1 | CMe= | N= | NH | CO |
| b.020 | CO | 1 | CtBu= | N= | $NC_2H_4F$ | CS |
| b.021 | CO | 1 | CEt= | N= | NH | CS |
| b.022 | CO | 0 | | CO | NH | CO |
| b.023 | CO | 0 | | NH | NH | CO |
| b.024 | CO | 0 | | $CH_2$ | S | CS |
| b.025 | CO | 0 | | $CHCH_2COOMe$ | NH | CS |
| b.026 | CO | 0 | | $CHC_2H_4COOMe$ | NH | CS |
| b.027 | CO | 0 | | NH | NH | CO |
| b.028 | CO | 0 | | $CMeCH{=}CMe_2$ | NH | CO |
| b.029 | CO | 0 | | $CMeCH_2CMe_2$ | NH | CO |
| b.030 | CO | 0 | | $CH_2$ | NH | CS |
| b.031 | CO | 0 | | $CMe_2$ | NH | CO |
| b.032 | $CH_2$ | 0 | | CO | NMe | CS |
| b.033 | $CH_2$ | 0 | | CO | NiPr | CS |
| b.034 | $CH_2$ | 0 | | CO | NEt | CS |
| b.035 | $CH_2$ | 0 | | CO | NH | CO |
| b.036 | $CH_2$ | 0 | | CO | NH | CS |
| b.037 | $CH_2$ | 1 | $CMe_2$ | CO | NH | CO |
| b.038 | $CH_2$ | 0 | | CO | NH | CO |
| b.039 | $CH_2$ | 1 | $CH_2$ | CO | NH | CO |
| b.040 | $CH_2$ | 0 | | $CH_2$ | O | CO |
| b.041 | $CH_2$ | 0 | | $CH_2$ | NH | CO |
| b.042 | $CH_2$ | 0 | | $CH_2$ | NH | CS |
| b.043 | $CH_2$ | 0 | | $CH_2$ | $CH_2$ | CO |
| b.044 | $CH_2$ | 0 | | $CH_2$ | NH | CO |
| b.045 | $CH_2$ | 0 | | $CH_2$ | NH | CO |
| b.046 | $CH_2$ | 1 | $CH_2$ | $CH_2$ | NH | CO |
| b.047 | $CH_2$ | 1 | $CMe_2$ | $CH_2$ | NH | CO |
| b.048 | $CH_2$ | 1 | $CMe_2$ | $CH_2$ | NH | CO |
| b.049 | $CH_2$ | 1 | $C(OMe)_2$ | $CH_2$ | NH | CO |
| b.050 | $CH_2$ | 1 | $C(OEt)_2$ | $CH_2$ | NH | CO |
| b.051 | $CH_2$ | 1 | $C(CH_2OH)_2$ | $CH_2$ | NH | CO |
| b.052 | $CH_2$ | 1 | CO | $CH_2$ | NH | CO |
| b.053 | $CH_2$ | 1 | CHOH | $CH_2$ | NH | CO |
| b.054 | $CH_2$ | 1 | O | $CH_2$ | NH | CO |
| b.055 | $CH_2$ | 1 | NMe | $CH_2$ | NH | CO |
| b.056 | $CH_2$ | 0 | | $CH_2$ | NH | CO |
| b.057 | $CH_2$ | 0 | | $CH_2$ | NMe | CO |
| b.058 | $CH_2$ | 0 | | $CH_2$ | NCOMe | CO |
| b.059 | $CH_2$ | 0 | | $CH_2$ | NCOEt | CO |
| b.060 | $CH_2$ | 0 | | $CH_2$ | NCO-nPr | CO |
| b.061 | $CH_2$ | 0 | | $CH_2$ | $NCOCH_2OMe$ | CO |
| b.062 | $CH_2$ | 0 | | $CH_2$ | $NCOCHMe_2$ | CO |
| b.063 | $CH_2$ | 1 | $CH_2$ | $CH_2$ | NH | CO |
| b.064 | $CH_2$ | 1 | $CH_2$ | $CH_2$ | NH | CO |
| b.065 | $CH_2$ | 1 | $CH_2$ | $CH_2$ | NMe | CO |
| b.066 | $CH_2$ | 1 | $CH_2$ | $CH_2$ | NCOMe | CO |
| b.067 | $CH_2$ | 1 | $CH_2$ | $CH_2$ | NCOEt | CO |
| b.068 | $CH_2$ | 1 | $CH_2$ | $CH_2$ | NCO-nPr | CO |

TABLE 1b-continued

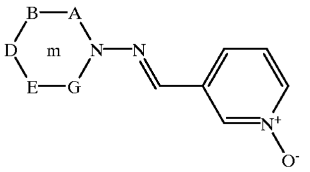

| Comp. | A | m | B | D | E | G |
|---|---|---|---|---|---|---|
| b.069 | $CH_2$ | 1 | $CH_2$ | $CH_2$ | $NCOCH_2OMe$ | CO |
| b.070 | $CH_2$ | 1 | $CH_2$ | $CH_2$ | $NCOCHMe_2$ | CO |
| b.071 | $CH_2$ | 1 | CH= | CH= | NH | CO |
| b.072 | $CH_2$ | 0 | | CHMe | NH | CO |
| b.073 | $CH_2$ | 0 | | CHMe | NH | CO |
| b.074 | $CH_2$ | 0 | | CHMe | NMe | CO |
| b.075 | $CH_2$ | 0 | | CHMe | NCOMe | CO |
| b.076 | $CH_2$ | 0 | | CHMe | NCOEt | CO |
| b.077 | $CH_2$ | 0 | | CHMe | NCO-nPr | CO |
| b.078 | $CH_2$ | 0 | | CHMe | $NCOCH_2OMe$ | CO |
| b.079 | $CH_2$ | 0 | | CHMe | $NCOCHMe_2$ | CO |
| b.080 | $CH_2$ | 1 | $CH_2$ | CHMe | NH | CO |
| b.081 | $CH_2$ | 1 | $CH_2$ | CHMe | NH | CO |
| b.082 | $CH_2$ | 1 | $CH_2$ | CHMe | NMe | CO |
| b.083 | $CH_2$ | 1 | $CH_2$ | CHMe | NCOMe | CO |
| b.084 | $CH_2$ | 1 | $CH_2$ | CHMe | NCOEt | CO |
| b.085 | $CH_2$ | 1 | $CH_2$ | CHMe | NCO-nPr | CO |
| b.086 | $CH_2$ | 1 | $CH_2$ | CHMe | $NCOCH_2OMe$ | CO |
| b.087 | $CH_2$ | 1 | $CH_2$ | CHMe | $NCOCHMe_2$ | CO |
| b.088 | $CH_2$ | 0 | | $CHCH_2OMe$ | NH | CO |
| b.089 | $CH_2$ | 1 | $CH_2$ | $CHCH_2OMe$ | NH | CO |
| b.090 | $CH_2$ | 0 | | CH-tBu | NH | CO |
| b.091 | $CH_2$ | 1 | $CH_2$ | CH-tBu | NH | CO |
| b.092 | $CH_2$ | 0 | | CH-iPr | NH | CO |
| b.093 | $CH_2$ | 1 | $CH_2$ | CH-iPr | NH | CO |
| b.094 | $CH_2$ | 0 | | CH-cPr | NH | CO |
| b.095 | $CH_2$ | 1 | $CH_2$ | CH-cPr | NH | CO |
| b.096 | $CH_2$ | 0 | | CHEt | NH | CO |
| b.098 | $CH_2$ | 0 | | CHEt | NMe | CO |
| b.099 | $CH_2$ | 0 | | CHEt | NCOMe | CO |
| b.100 | $CH_2$ | 0 | | CHEt | NCOEt | CO |
| b.101 | $CH_2$ | 0 | | CHEt | NCO-nPr | CO |
| b.102 | $CH_2$ | 0 | | CHEt | $NCOCH_2OMe$ | CO |
| b.103 | $CH_2$ | 0 | | CHEt | $NCOCHMe_2$ | CO |
| b.104 | $CH_2$ | 1 | $CH_2$ | CHEt | NH | CO |
| b.106 | $CH_2$ | 1 | $CH_2$ | CHEt | NMe | CO |
| b.107 | $CH_2$ | 1 | $CH_2$ | CHEt | NCOMe | CO |
| b.108 | $CH_2$ | 1 | $CH_2$ | CHEt | NCOEt | CO |
| b.109 | $CH_2$ | 1 | $CH_2$ | CHEt | NCO-nPr | CO |
| b.110 | $CH_2$ | 1 | $CH_2$ | CHEt | $NCOCH_2OMe$ | CO |
| b.111 | $CH_2$ | 1 | $CH_2$ | CHEt | $NCOCHMe_2$ | CO |
| b.112 | $CH_2$ | 1 | CMe= | CH= | NH | CO |
| b.113 | $CH_2$ | 1 | CEt= | CH= | NH | CO |
| b.114 | $CH_2$ | 1 | CH= | C(t-Bu)= | NMe | CO |
| b.115 | CH= | 0 | | N= | $NCOCH_3$ | CO |
| b.116 | CH= | 0 | | N= | $NCONMe_2$ | CNH |
| b.117 | CH= | 0 | | N= | NH | CO |
| b.118 | CH= | 1 | CH= | NH | NH | CO |
| b.119 | CH= | 1 | CMe= | $CH_2$ | NH | CO |
| b.120 | CH= | 1 | CEt= | $CH_2$ | NH | CO |
| b.121 | CH= | 0 | | CMe= | NH | CO |
| b.122 | CH= | 1 | CH= | CHMe | NH | CO |
| b.123 | CH= | 0 | | CtBu= | NH | CO |
| b.124 | CHMe | 0 | | $CH_2$ | NH | CO |
| b.125 | CHMe | 0 | | $CH_2$ | NMe | CO |
| b.126 | CHMe | 0 | | $CH_2$ | NCOMe | CO |
| b.127 | CHMe | 0 | | $CH_2$ | NCOEt | CO |
| b.128 | CHMe | 0 | | $CH_2$ | NCOnPr | CO |
| b.129 | CHMe | 0 | | $CH_2$ | $NCOCH_2OMe$ | CO |
| b.130 | CHMe | 0 | | $CH_2$ | $NCOCHMe_2$ | CO |
| b.131 | CHMe | 1 | $CH_2$ | $CH_2$ | NH | CO |
| b.132 | CHMe | 1 | $CH_2$ | $CH_2$ | NMe | CO |
| b.133 | CHMe | 1 | $CH_2$ | $CH_2$ | NCOMe | CO |
| b.134 | CHMe | 1 | $CH_2$ | $CH_2$ | NCOEt | CO |
| b.135 | CHMe | 1 | $CH_2$ | $CH_2$ | NCOnPr | CO |
| b.136 | CHMe | 1 | $CH_2$ | $CH_2$ | $NCOCH_2OMe$ | CO |
| b.137 | CHMe | 1 | $CH_2$ | $CH_2$ | $NCOCHMe_2$ | CO |
| b.138 | CMe= | 0 | | C= | $NCH_3$ | CO |

TABLE 1b-continued

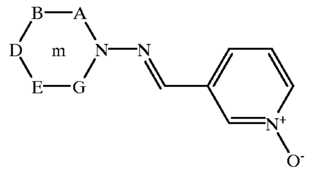

| Comp. | A | m | B | D | E | G |
|---|---|---|---|---|---|---|
| b.139 | CHMe | 1 | CH= | CH= | NH | CO |
| b.140 | CHMe | 0 | | CHMe | NH | CO |
| b.141 | CHMe | 0 | | CHMe | NMe | CO |
| b.142 | CHMe | 0 | | CHMe | NCOMe | CO |
| b.143 | CHMe | 0 | | CHMe | NCOEt | CO |
| b.144 | CHMe | 0 | | CHMe | NCOnPr | CO |
| b.145 | CHMe | 0 | | CHMe | $NCOCH_2OMe$ | CO |
| b.146 | CHMe | 0 | | CHMe | $NCOCHMe_2$ | CO |
| b.147 | CHMe | 1 | $CH_2$ | CHMe | NH | CO |
| b.148 | CHMe | 1 | $CH_2$ | CHMe | NMe | CO |
| b.149 | CHMe | 1 | $CH_2$ | CHMe | NCOMe | CO |
| b.150 | CHMe | 1 | $CH_2$ | CHMe | NCOEt | CO |
| b.151 | CHMe | 1 | $CH_2$ | CHMe | NCOnPr | CO |
| b.152 | CHMe | 1 | $CH_2$ | CHMe | $NCOCH_2OMe$ | CO |
| b.153 | CHMe | 1 | $CH_2$ | CHMe | $NCOCHMe_2$ | CO |
| b.154 | CHMe | 0 | | CHEt | NH | CO |
| b.155 | CHMe | 0 | | CHEt | NMe | CO |
| b.156 | CHMe | 0 | | CHEt | NCOMe | CO |
| b.157 | CHMe | 0 | | CHEt | NCOEt | CO |
| b.158 | CHMe | 0 | | CHEt | NCOnPr | CO |
| b.159 | CHMe | 0 | | CHEt | $NCOCH_2OMe$ | CO |
| b.160 | CHMe | 0 | | CHEt | $NCOCHMe_2$ | CO |
| b.161 | CHMe | 1 | $CH_2$ | CHEt | NH | CO |
| b.162 | CHMe | 1 | $CH_2$ | CHEt | NMe | CO |
| b.163 | CHMe | 1 | $CH_2$ | CHEt | NCOMe | CO |
| b.164 | CHMe | 1 | $CH_2$ | CHEt | NCOEt | CO |
| b.165 | CHMe | 1 | $CH_2$ | CHEt | NCOnPr | CO |
| b.166 | CHMe | 1 | $CH_2$ | CHEt | $NCOCH_2OMe$ | CO |
| b.167 | CHMe | 1 | $CH_2$ | CHEt | $NCOCHMe_2$ | CO |
| b.168 | $CHCH_2OMe$ | 0 | | $CH_2$ | NH | CO |
| b.169 | $CHCH_2OMe$ | 1 | $CH_2$ | $CH_2$ | NH | CO |
| b.170 | CHtBu | 0 | | $CH_2$ | NH | CO |
| b.171 | CHtBu | 1 | $CH_2$ | $CH_2$ | NH | CO |
| b.172 | CHiPr | 0 | | $CH_2$ | NH | CO |
| b.173 | CHiPr | 1 | $CH_2$ | $CH_2$ | NH | CO |
| b.174 | CHiPr | 0 | | $CH_2$ | NH | CO |
| b.175 | CHiPr | 0 | | $CH_2$ | NMe | CO |
| b.176 | CHiPr | 0 | | $CH_2$ | NCOMe | CO |
| b.177 | CHiPr | 0 | | $CH_2$ | NCOEt | CO |
| b.178 | CHiPr | 0 | | $CH_2$ | NCOnPr | CO |
| b.179 | CHiPr | 0 | | $CH_2$ | $NCOCH_2OMe$ | CO |
| b.180 | CHiPr | 0 | | $CH_2$ | $NCOCHMe_2$ | CO |
| b.181 | CHiPr | 1 | $CH_2$ | $CH_2$ | NH | CO |
| b.182 | CHiPr | 1 | $CH_2$ | $CH_2$ | NMe | CO |
| b.183 | CHiPr | 1 | $CH_2$ | $CH_2$ | NCOMe | CO |
| b.184 | CHiPr | 1 | $CH_2$ | $CH_2$ | NCOEt | CO |
| b.185 | CHiPr | 1 | $CH_2$ | $CH_2$ | NCO-nPr | CO |
| b.186 | CHiPr | 1 | $CH_2$ | $CH_2$ | $NCOCH_2OMe$ | CO |
| b.187 | CHiPr | 1 | $CH_2$ | $CH_2$ | $NCOCHMe_2$ | CO |
| b.188 | CHiPr | 0 | | CHMe | NH | CO |
| b.189 | CHiPr | 0 | | CHMe | NMe | CO |
| b.190 | CHiPr | 0 | | CHMe | NCOMe | CO |
| b.191 | CHiPr | 0 | | CHMe | NCOEt | CO |
| b.192 | CHiPr | 0 | | CHMe | NCOnPr | CO |
| b.193 | CHiPr | 0 | | CHMe | $NCOCH_2OMe$ | CO |
| b.194 | CHiPr | 0 | | CHMe | $NCOCHMe_2$ | CO |
| b.195 | CHiPr | 1 | $CH_2$ | CHMe | NH | CO |
| b.196 | CHiPr | 1 | $CH_2$ | CHMe | NMe | CO |
| b.197 | CHiPr | 1 | $CH_2$ | CHMe | NCOMe | CO |
| b.198 | CHiPr | 1 | $CH_2$ | CHMe | NCOEt | CO |
| b.199 | CHiPr | 1 | $CH_2$ | CHMe | NCOnPr | CO |
| b.200 | CHiPr | 1 | $CH_2$ | CHMe | $NCOCH_2OMe$ | CO |
| b.201 | CHiPr | 1 | $CH_2$ | CHMe | $NCOCHMe_2$ | CO |
| b.202 | CHiPr | 0 | | CHEt | NH | CO |
| b.203 | CHiPr | 0 | | CHEt | NMe | CO |
| b.204 | CHiPr | 0 | | CHEt | NCOMe | CO |
| b.205 | CHiPr | 0 | | CHEt | NCOEt | CO |
| b.206 | CHiPr | 0 | | CHEt | NCOnPr | CO |

TABLE 1b-continued

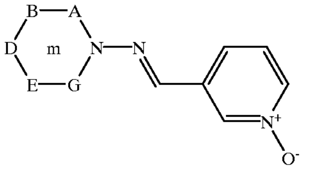

| Comp. | A | m | B | D | E | G |
|---|---|---|---|---|---|---|
| b.207 | CHiPr | 0 | | CHEt | $NCOCH_2OMe$ | CO |
| b.208 | CHiPr | 0 | | CHEt | $NCOCHMe_2$ | CO |
| b.209 | CHiPr | 1 | $CH_2$ | CHEt | NH | CO |
| b.210 | CHiPr | 1 | $CH_2$ | CHEt | NMe | CO |
| b.211 | CHiPr | 1 | $CH_2$ | CHEt | NCOMe | CO |
| b.212 | CHiPr | 1 | $CH_2$ | CHEt | NCOEt | CO |
| b.213 | CHiPr | 1 | $CH_2$ | CHEt | NCOnPr | CO |
| b.214 | CHiPr | 1 | $CH_2$ | CHEt | $NCOCH_2OMe$ | CO |
| b.215 | CHiPr | 1 | $CH_2$ | CHEt | $NCOCHMe_2$ | CO |
| b.216 | CHcPr | 0 | | $CH_2$ | NH | CO |
| b.217 | CHcPr | 1 | $CH_2$ | $CH_2$ | NH | CO |
| b.218 | CHEt | 0 | | $CH_2$ | NH | CO |
| b.219 | CHEt | 1 | $CH_2$ | $CH_2$ | NH | CO |
| b.220 | CHEt | 0 | | $CH_2$ | NH | CO |
| b.221 | CHEt | 0 | | $CH_2$ | NMe | CO |
| b.222 | CHEt | 0 | | $CH_2$ | NCOMe | CO |
| b.223 | CHEt | 0 | | $CH_2$ | NCOEt | CO |
| b.224 | CHEt | 0 | | $CH_2$ | NCOnPr | CO |
| b.225 | CHEt | 0 | | $CH_2$ | $NCOCH_2OMe$ | CO |
| b.226 | CHEt | 0 | | $CH_2$ | $NCOCHMe_2$ | CO |
| b.227 | CHEt | 1 | $CH_2$ | $CH_2$ | NH | CO |
| b.228 | CHEt | 1 | $CH_2$ | $CH_2$ | NMe | CO |
| b.229 | CHEt | 1 | $CH_2$ | $CH_2$ | NCOMe | CO |
| b.230 | CHEt | 1 | $CH_2$ | $CH_2$ | NCOEt | CO |
| b.231 | CHEt | 1 | $CH_2$ | $CH_2$ | NCOnPr | CO |
| b.232 | CHEt | 1 | $CH_2$ | $CH_2$ | $NCOCH_2OMe$ | CO |
| b.233 | CHEt | 1 | $CH_2$ | $CH_2$ | $NCOCHMe_2$ | CO |
| b.234 | CHEt | 0 | | CHMe | NH | CO |
| b.235 | CHEt | 0 | | CHMe | NMe | CO |
| b.236 | CHEt | 0 | | CHMe | NCOMe | CO |
| b.237 | CHEt | 0 | | CHMe | NCOEt | CO |
| b.238 | CHEt | 0 | | CHMe | NCO-nPr | CO |
| b.239 | CHEt | 0 | | CHMe | $NCOCH_2OMe$ | CO |
| b.240 | CHEt | 0 | | CHMe | $NCOCHMe_2$ | CO |
| b.241 | CHEt | 1 | $CH_2$ | CHMe | NH | CO |
| b.242 | CHEt | 1 | $CH_2$ | CHMe | NMe | CO |
| b.243 | CHEt | 1 | $CH_2$ | CHMe | NCOMe | CO |
| b.244 | CHEt | 1 | $CH_2$ | CHMe | NCOEt | CO |
| b.245 | CHEt | 1 | $CH_2$ | CHMe | NCOnPr | CO |
| b.246 | CHEt | 1 | $CH_2$ | CHMe | $NCOCH_2OMe$ | CO |
| b.247 | CHEt | 1 | $CH_2$ | CHMe | $NCOCHMe_2$ | CO |
| b.248 | CHEt | 0 | | CHEt | NH | CO |
| b.249 | CHEt | 0 | | CHEt | NMe | CO |
| b.250 | CHEt | 0 | | CHEt | NCOMe | CO |
| b.251 | CHEt | 0 | | CHEt | NCOEt | CO |
| b.252 | CHEt | 0 | | CHEt | NCOnPr | CO |
| b.253 | CHEt | 0 | | CHEt | $NCOCH_2OMe$ | CO |
| b.254 | CHEt | 0 | | CHEt | $NCOCHMe_2$ | CO |
| b.255 | CHEt | 1 | $CH_2$ | CHEt | NH | CO |
| b.256 | CHEt | 1 | $CH_2$ | CHEt | NMe | CO |
| b.257 | CHEt | 1 | $CH_2$ | CHEt | NCOMe | CO |
| b.258 | CHEt | 1 | $CH_2$ | CHEt | NCOEt | CO |
| b.259 | CHEt | 1 | $CH_2$ | CHEt | NCOnPr | CO |
| b.260 | CHEt | 1 | $CH_2$ | CHEt | $NCOCH_2OMe$ | CO |
| b.261 | CHEt | 1 | $CH_2$ | CHEt | $NCOCHMe_2$ | CO |
| b.262 | CSMe= | 1 | N= | CO | NMe | CO |
| b.263 | CNHCOOEt= | 0 | | N= | NH | CS |
| b.264 | CNHCOOMe= | 0 | | N= | NH | CS |
| b.265 | CNHMe= | 1 | N= | CO | NMe | CO |
| b.266 | $CMe_2$ | 0 | | CO | NH | CO |
| b.267 | $CMe_2$ | 1 | $CH_2$ | CO | NH | CO |
| b.268 | $CMe_2$ | 0 | | $CH_2$ | NH | CO |
| b.269 | $CMe_2$ | 1 | $CH_2$ | $CH_2$ | NH | CO |
| b.270 | CMe= | 0 | | CCOOEt= | S | CNH |
| b.271 | CMe= | 0 | | N= | NH | CS |
| b.273 | CMe= | 0 | | N= | NH | CO |
| b.274 | CMe= | 1 | CH= | NH | NH | CO |
| b.275 | CMe= | 0 | | CH= | S | CNH |

TABLE 1b-continued

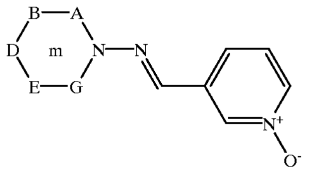

| Comp. | A | m | B | D | E | G |
|---|---|---|---|---|---|---|
| b.276 | CHMe | 0 | | $CH_2$ | NH | CO |
| b.277 | CMe= | 1 | CH= | $CH_2$ | NH | CO |
| b.278 | $CCH_2OMe$= | 0 | | N= | NH | CS |
| b.279 | $CCH_2OEt$= | 0 | | N= | NH | CS |
| b.280 | $CCH_2iPr$= | 0 | | N= | NH | CS |
| b.281 | $CCF_3$= | 0 | | N= | NH | CS |
| b.282 | CcHex= | 0 | | N= | NH | CS |
| b.283 | CiPr= | 0 | | N= | NH | CS |
| b.284 | CcPr= | 0 | | N= | NH | CS |
| b.285 | CEt= | 0 | | N= | NH | CS |
| b.286 | CEt= | 0 | | N= | NH | CO |
| b.287 | $CC_2F_5$= | 0 | | N= | NH | CS |
| b.288 | CBr= | 0 | | N= | NH | CS |
| b.289 | C(=NH) | 0 | | $CMe_2$ | NH | CO |
| b.290 | C(=NH) | 1 | CH= | CMe= | NH | CO |
| b.291 | $CH_2$ | 1 | CHMe | NH | NH | CO |
| b.292 | $CH_2$ | 1 | CHEt | NH | NH | CO |
| b.293 | $CH_2$ | 1 | CHcPr | NH | NH | CO |
| b.294 | $CH_2$ | 1 | CHtBu | NH | NH | CO |
| b.295 | $CH_2$ | 1 | $CHCH_2OMe$ | NH | NH | CO |
| b.296 | CHMe | 1 | CHMe | NH | NH | CO |
| b.297 | CHMe | 1 | CHEt | NH | NH | CO |
| b.298 | CHMe | 1 | CHcPr | NH | NH | CO |
| b.299 | CHMe | 1 | CHtBu | NH | NH | CO |
| b.300 | CHMe | 1 | $CHCH_2OMe$ | NH | NH | CO |
| b.301 | $CMe_2$ | 1 | CHMe | NH | NH | CO |
| b.302 | $CMe_2$ | 1 | CHEt | NH | NH | CO |
| b.303 | $CMe_2$ | 1 | CHcPr | NH | NH | CO |
| b.304 | $CMe_2$ | 1 | CHtBu | NH | NH | CO |
| b.305 | $CMe_2$ | 1 | $CHCH_2OMe$ | NH | NH | CO |
| b.306 | $CH_2$ | 1 | CHMe | NCOMe | NCOMe | CO |
| b.307 | $CH_2$ | 1 | CHMe | $NCOCH_2OMe$ | $NCOCH_2OMe$ | CO |
| b.308 | $CH_2$ | 1 | CHMe | NCO-cPr | NCO-cPr | CO |
| b.309 | $CH_2$ | 1 | CHMe | $NCOCH_2Cl$ | $NCOCH_2Cl$ | CO |
| b.310 | $CH_2$ | 1 | CHMe | NCOEt | NCOEt | CO |
| b.311 | $CH_2$ | 1 | CHMe | $NCOCHMe_2$ | $NCOCHMe_2$ | CO |
| b.312 | $CH_2$ | 1 | CHMe | NCOOEt | NCOOEt | CO |
| b.313 | $CH_2$ | 1 | CHMe | NCOMe | NH | CO |
| b.314 | $CH_2$ | 1 | CHMe | $NCOCH_2OMe$ | NH | CO |
| b.315 | $CH_2$ | 1 | CHMe | NCO-cPr | NH | CO |
| b.316 | $CH_2$ | 1 | CHMe | $NCOCH_2Cl$ | NH | CO |
| b.317 | $CH_2$ | 1 | CHMe | NCOEt | NH | CO |
| b.318 | $CH_2$ | 1 | CHMe | $NCOCHMe_2$ | NH | CO |
| b.319 | $CH_2$ | 1 | CHMe | NCOOEt | NH | CO |
| b.320 | CH= | 0 | | CMe= | N(—N=CH-3-pyridinyl) | CO |
| b.321 | $CH_2$ | 0 | | C(Me)(OH) | N(—N=CH-3-pyridinyl) | CO |

TABLE 1c

| melting points of compounds from Table 1b | |
|---|---|
| Comp. | m.p.(°) |
| b.072 | 218–221 |
| b.074 | 223–225 |
| b.080 | 207–213 |
| b.083 | 270–275 |
| b.124 | 190–195 |
| b.273 | >260 |

Example P11

4-Amino-1,2,4-triazol-3-one (Compound 2.117 in Table 2)

A mixture of 54 g of carbohydrazide and 88.8 g of orthoformic acid triethyl ester is maintained at 130° for 4 hours, the alcohol that forms being distilled off continuously. The resulting solid residue is recrystallised twice from 200 ml of ethanol/water (3:1). 32.5 g of the title compound having a melting point of 186–188° are obtained.

Example P12

4-Amino-5-methyl-1,2,4-triazol-3-one (Compound 2.272 in Table 2)

A mixture of 52.2 g of carbethoxyhydrazone and 22.5 g of hydrazine hydrate in 200 ml of n-propanol is stirred under reflux for 30 hours. The mixture is cooled and then the crystals are filtered off with suction, washed with a small amount of n-propanol and dried under a high vacuum. 17.4 g of the title compound having a melting point of 225–230° are obtained.

Example P13

1-Amino-3,4-dimethyl-1,3-dihydroimidazol-2-one (Compound 2.121 in Table 2)

2 g of hydrazine hydrate are added to a solution of 2 g of 3,4-dimethyl-1-(pyridin-3-ylmethyleneamino)-2,3-dihydroimidazol-2-one in 12 ml of methanol and the suspension is boiled under reflux for 6 hours, then concentrated by evaporation and chromatographed on silica gel. 1 g of pyridine-3-carbaldehyde hydrazone and 0.7 g of the title compound having a melting point of 115–119° are thus obtained.

Example P14

1-Amino-3,4-dimethylimidazolidin-2-one (Compound 2.074 in Table 2)

1.6 g of Rh/C are added to a solution of 1-amino-3,4-dimethyl-2-oxo-1,3-dihydroimidazole hydrochloride in 150 ml of methanol and the reaction mixture is hydrogenated with hydrogen under normal pressure. After 4 hours, 1.13 litres of hydrogen have been taken up and the reaction ceases. The reaction mixture is then filtered over Celite and concentrated by evaporation. The residue is stirred with tetrahydrofuran. The crystals are filtered off with suction and dried in vacuo at 60°. 7 g of the title compound in the form of the hydrochloride having a melting point of 162–164° are obtained.

Example P15

1-Amino-3,4-dimethyl-2-oxo-1,3-dihydroimidazole hydrochloride (Compound 2.121 in Table 2 in the form of the hydrochloride)

80.8 g of (3,4-dimethyl-2-oxo-1,3-dihydroimidazol-1-yl) acetamide are suspended in 800 ml of methanol and then heated to 42°. At that temperature, 28 g of hydrogen chloride gas are introduced in the course of 40 minutes; with heating to more than 50° a clear solution forms. The clear solution is concentrated and the residue is stirred with a small amount of tetrahydrofuran. The crystals that have precipitated are filtered off with suction and dried. The hydrochloride of the title compound having a melting point of 162–165° is thus obtained.

Example P16

4-Amino-6-methyl-3-oxo-1,4,5,6-tetrahydro-1,2,4-triazine hydrochloride (Compound 2.291 in Table 2 in the form of the hydrochloride)

0.4 g of platinum oxide is added to a solution of 4-amino-6-methyl-3-oxo-4,5-dihydro-1,2,4-triazine hydrochloride in 80 ml of methanol and 8 ml of water, and then in the course of 200 minutes 614 ml of hydrogen are introduced. The catalyst is filtered off and the filtrate is concentrated by evaporation. The residue is concentrated by evaporation several times with 20 ml of isopropanol and 20 ml of toluene each time and then stirred with ether. 3.8 g of the title compound are thus obtained.

Example P17

The other compounds listed in Tables 2 and 2a can also be prepared in a manner analogous to that described in Examples P11 to P16. Some of the examples listed in Table 2 are obtained via the compounds listed in Table 3 (in accordance with Preparation Variant e), 3a (in accordance with Preparation Variant g), 7 (in accordance with Preparation Variant p), 8a/b (in accordance with Preparation Variant n) and 9 (in accordance with Preparation Variant i).

TABLE 2

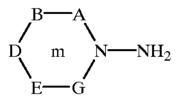

| Comp. | A | m | B | D | E | G |
|---|---|---|---|---|---|---|
| 2.001 | CS | 0 | | NH | NH | CS |
| 2.002 | CS | 0 | | NH | NH | CO |
| 2.003 | CO | 1 | —CMe= | N= | NH | CS |
| 2.004 | CO | 1 | $C(C_2H_4iPr)=$ | N= | NH | CS |
| 2.005 | CO | 1 | $C(CH_2iPr)=$ | N= | NH | CS |
| 2.006 | CO | 1 | CtBu= | N= | NH | CS |
| 2.007 | CO | 1 | CtBu= | N= | NH | CO |
| 2.008 | CO | 1 | CcPr= | N= | NH | CS |
| 2.009 | CO | 1 | CcHex= | N= | NH | CS |
| 2.010 | CO | 1 | $NCH_2$-cHex | CO | NH | CO |
| 2.011 | CO | 1 | $CH_2$ | CO | NH | CO |
| 2.012 | CO | 1 | $CH_2$ | $CH_2$ | NH | CO |
| 2.013 | CO | 1 | $CH_2$ | $CMe_2$ | NH | CO |
| 2.014 | CO | 1 | CH= | CMe= | NH | CO |
| 2.015 | CO | 1 | CH= | N= | NH | CS |
| 2.016 | CO | 1 | CH= | $C(CF_3)=$ | NH | CNH |
| 2.017 | CO | 1 | $CMe_2$ | CO | NH | CO |
| 2.018 | CO | 1 | $CMe_2$ | $CH_2$ | NH | CO |
| 2.019 | CO | 1 | CMe= | N= | NH | CO |
| 2.020 | CO | 1 | CtBu= | N= | $NC_2H_4F$ | CS |
| 2.021 | CO | 1 | CEt= | N= | NH | CS |
| 2.022 | CO | 0 | | CO | NH | CO |
| 2.023 | CO | 0 | | NH | NH | CO |
| 2.024 | CO | 0 | | $CH_2$ | S | CS |
| 2.025 | CO | 0 | | $CHCH_2COOMe$ | NH | CS |
| 2.026 | CO | 0 | | $CHC_2H_4COOMe$ | NH | CS |
| 2.027 | CO | 0 | | NH | NH | CO |

TABLE 2-continued

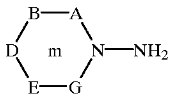

| Comp. | A | m | B | D | E | G |
|---|---|---|---|---|---|---|
| 2.028 | CO | 0 | | $CMeCH{=}CMe_2$ | NH | CO |
| 2.029 | CO | 0 | | $CMeCH_2CMe_2$ | NH | CO |
| 2.030 | CO | 0 | | $CH_2$ | NH | CS |
| 2.030 | CO | 0 | | $CH_2$ | NH | CS |
| 2.031 | CO | 0 | | $CMe_2$ | NH | CO |
| 2.032 | $CH_2$ | 0 | | CO | NMe | CS |
| 2.033 | $CH_2$ | 0 | | CO | NiPr | CS |
| 2.034 | $CH_2$ | 0 | | CO | NEt | CS |
| 2.035 | $CH_2$ | 0 | | CO | NH | CO |
| 2.036 | $CH_2$ | 0 | | CO | NH | CS |
| 2.037 | $CH_2$ | 1 | $CMe_2$ | CO | NH | CO |
| 2.038 | $CH_2$ | 0 | | CO | NH | CO |
| 2.039 | $CH_2$ | 1 | $CH_2$ | CO | NH | CO |
| 2.040 | $CH_2$ | 0 | | $CH_2$ | O | CO |
| 2.041 | $CH_2$ | 0 | | $CH_2$ | NH | CO |
| 2.042 | $CH_2$ | 0 | | $CH_2$ | NH | CS |
| 2.043 | $CH_2$ | 0 | | $CH_2$ | $CH_2$ | CO |
| 2.044 | $CH_2$ | 0 | | $CH_2$ | NH | CO |
| 2.045 | $CH_2$ | 0 | | $CH_2$ | NH | CO |
| 2.046 | $CH_2$ | 1 | $CH_2$ | $CH_2$ | NH | CO |
| 2.047 | $CH_2$ | 1 | $CMe_2$ | $CH_2$ | NH | CO |
| 2.048 | $CH_2$ | 1 | $CMe_2$ | $CH_2$ | NH | CO |
| 2.049 | $CH_2$ | 1 | $C(OMe)_2$ | $CH_2$ | NH | CO |
| 2.050 | $CH_2$ | 1 | $C(OEt)_2$ | $CH_2$ | NH | CO |
| 2.051 | $CH_2$ | 1 | $C(CH_2OH)_2$ | $CH_2$ | NH | CO |
| 2.052 | $CH_2$ | 1 | CO | $CH_2$ | NH | CC |
| 2.053 | $CH_2$ | 1 | CHOH | $CH_2$ | NH | CO |
| 2.054 | $CH_2$ | 1 | O | $CH_2$ | NH | CO |
| 2.055 | $CH_2$ | 1 | NMe | $CH_2$ | NH | CO |
| 2.056 | $CH_2$ | 0 | | $CH_2$ | NH | CO |
| 2.057 | $CH_2$ | 0 | | $CH_2$ | NMe | CO |
| 2.058 | $CH_2$ | 0 | | $CH_2$ | NCOMe | CO |
| 2.059 | $CH_2$ | 0 | | $CH_2$ | NCOEt | CO |
| 2.060 | $CH_2$ | 0 | | $CH_2$ | NCOnPr | CO |
| 2.061 | $CH_2$ | 0 | | $CH_2$ | $NCOCH_2OMe$ | CO |
| 2.062 | $CH_2$ | 0 | | $CH_2$ | $NCOCHMe_2$ | CO |
| 2.063 | $CH_2$ | 1 | $CH_2$ | $CH_2$ | NH | CO |
| 2.064 | $CH_2$ | 1 | $CH_2$ | $CH_2$ | NH | CO |
| 2.065 | $CH_2$ | 1 | $CH_2$ | $CH_2$ | NMe | CO |
| 2.066 | $CH_2$ | 1 | $CH_2$ | $CH_2$ | NCOMe | CO |
| 2.067 | $CH_2$ | 1 | $CH_2$ | $CH_2$ | NCOEt | CO |
| 2.068 | $CH_2$ | 1 | $CH_2$ | $CH_2$ | NCOnPr | CO |
| 2.069 | $CH_2$ | 1 | $CH_2$ | $CH_2$ | $NCOCH_2OMe$ | CO |
| 2.070 | $CH_2$ | 1 | $CH_2$ | $CH_2$ | $NCOCHMe_2$ | CO |
| 2.071 | $CH_2$ | 1 | $CH{=}$ | $CH{=}$ | NH | CO |
| 2.072 | $CH_2$ | 0 | | CHMe | NH | CO |
| 2.073 | $CH_2$ | 0 | | CHMe | NH | CO |
| 2.074 | $CH_2$ | 0 | | CHMe | NMe | CO |
| 2.075 | $CH_2$ | 0 | | CHMe | NCOMe | CO |
| 2.076 | $CH_2$ | 0 | | CHMe | NCOEt | CO |
| 2.077 | $CH_2$ | 0 | | CHMe | NCOnPr | CO |
| 2.078 | $CH_2$ | 0 | | CHMe | $NCOCH_2OMe$ | CO |
| 2.079 | $CH_2$ | 0 | | CHMe | $NCOCHMe_2$ | CO |
| 2.080 | $CH_2$ | 1 | $CH_2$ | CHMe | NH | CO |
| 2.081 | $CH_2$ | 1 | $CH_2$ | CHMe | NH | CO |
| 2.082 | $CH_2$ | 1 | $CH_2$ | CHMe | NMe | CO |
| 2.083 | $CH_2$ | 1 | $CH_2$ | CHMe | NCOMe | CO |
| 2.084 | $CH_2$ | 1 | $CH_2$ | CHMe | NCOEt | CO |
| 2.085 | $CH_2$ | 1 | $CH_2$ | CHMe | NCOnPr | CO |
| 2.086 | $CH_2$ | 1 | $CH_2$ | CHMe | $NCOCH_2OMe$ | CO |
| 2.087 | $CH_2$ | 1 | $CH_2$ | CHMe | $NCOCHMe_2$ | CO |
| 2.088 | $CH_2$ | 0 | | $CHCH_2OMe$ | NH | CO |
| 2.089 | $CH_2$ | 1 | $CH_2$ | $CHCH_2OMe$ | NH | CO |
| 2.090 | $CH_2$ | 0 | | CHtBu | NH | CO |
| 2.091 | $CH_2$ | 1 | $CH_2$ | CHtBu | NH | CO |
| 2.092 | $CH_2$ | 0 | | CHiPr | NH | CO |
| 2.093 | $CH_2$ | 1 | $CH_2$ | CHiPr | NH | CO |
| 2.094 | $CH_2$ | 0 | | CHcPr | NH | CO |
| 2.095 | $CH_2$ | 1 | $CH_2$ | CHcPr | NH | CO |
| 2.096 | $CH_2$ | 0 | | CHEt | NH | CO |
| 2.098 | $CH_2$ | 0 | | CHEt | NMe | CO |

TABLE 2-continued

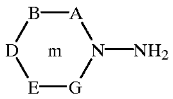

| Comp. | A | m | B | D | E | G |
|---|---|---|---|---|---|---|
| 2.099 | $CH_2$ | 0 | | CHEt | NCOMe | CO |
| 2.100 | $CH_2$ | 0 | | CHEt | NCOEt | CO |
| 2.101 | $CH_2$ | 0 | | CHEt | NCOnPr | CO |
| 2.102 | $CH_2$ | 0 | | CHEt | $NCOCH_2OMe$ | CO |
| 2.103 | $CH_2$ | 0 | | CHEt | $NCOCHMe_2$ | CO |
| 2.104 | $CH_2$ | 1 | $CH_2$ | CHEt | NH | CO |
| 2.106 | $CH_2$ | 1 | $CH_2$ | CHEt | NMe | CO |
| 2.107 | $CH_2$ | 1 | $CH_2$ | CHEt | NCOMe | CO |
| 2.108 | $CH_2$ | 1 | $CH_2$ | CHEt | NCOEt | CO |
| 2.109 | $CH_2$ | 1 | $CH_2$ | CHEt | NCOnPr | CO |
| 2.110 | $CH_2$ | 1 | $CH_2$ | CHEt | $NCOCH_2OMe$ | CO |
| 2.111 | $CH_2$ | 1 | $CH_2$ | CHEt | $NCOCHMe_2$ | CO |
| 2.112 | $CH_2$ | 1 | CMe= | CH= | NH | CO |
| 2.113 | $CH_2$ | 1 | CEt= | CH= | NH | CO |
| 2.114 | $CH_2$ | 1 | CH= | CtBu= | NMe | CO |
| 2.115 | CH= | 0 | | N= | $NCOCH_3$ | CO |
| 2.116 | CH= | 0 | | N= | $NCONMe_2$ | CNH |
| 2.117 | CH= | 0 | | N= | NH | CO |
| 2.118 | CH= | 1 | CH= | NH | NH | CO |
| 2.119 | CH= | 1 | CMe= | $CH_2$ | NH | CO |
| 2.120 | CH= | 1 | CEt= | $CH_2$ | NH | CO |
| 2.121 | CH= | 0 | | CMe= | NMe | CO |
| 2.122 | CH= | 1 | CH= | CHMe | NH | CO |
| 2.123 | CH= | 0 | | CtBu= | NH | CO |
| 2.124 | CHMe | 0 | | $CH_2$ | NH | CO |
| 2.125 | CHMe | 0 | | $CH_2$ | NMe | CO |
| 2.126 | CHMe | 0 | | $CH_2$ | NCOMe | CO |
| 2.127 | CHMe | 0 | | $CH_2$ | NCOEt | CO |
| 2.128 | CHMe | 0 | | $CH_2$ | NCOnPr | CO |
| 2.129 | CHMe | 0 | | $CH_2$ | $NCOCH_2OMe$ | CO |
| 2.130 | CHMe | 0 | | $CH_2$ | $NCOCHMe_2$ | CO |
| 2.131 | CHMe | 1 | $CH_2$ | $CH_2$ | NH | CO |
| 2.132 | CHMe | 1 | $CH_2$ | $CH_2$ | NMe | CO |
| 2.133 | CHMe | 1 | $CH_2$ | $CH_2$ | NCOMe | CO |
| 2.134 | CHMe | 1 | $CH_2$ | $CH_2$ | NCOEt | CO |
| 2.135 | CHMe | 1 | $CH_2$ | $CH_2$ | NCOnPr | CO |
| 2.136 | CHMe | 1 | $CH_2$ | $CH_2$ | $NCOCH_2OMe$ | CO |
| 2.137 | CHMe | 1 | $CH_2$ | $CH_2$ | $NCOCHMe_2$ | CO |
| 2.138 | CMe= | 0 | | C= | $NCH_3$ | CO |
| 2.139 | CHMe | 1 | CH= | CH= | NH | CO |
| 2.140 | CHMe | 0 | | CHMe | NH | CO |
| 2.141 | CHMe | 0 | | CHMe | NMe | CO |
| 2.142 | CHMe | 0 | | CHMe | NCOMe | CO |
| 2.143 | CHMe | 0 | | CHMe | NCOEt | CO |
| 2.144 | CHMe | 0 | | CHMe | NCOnPr | CO |
| 2.145 | CHMe | 0 | | CHMe | $NCOCH_2OMe$ | CO |
| 2.146 | CHMe | 0 | | CHMe | $NCOCHMe_2$ | CO |
| 2.147 | CHMe | 1 | $CH_2$ | CHMe | NH | CO |
| 2.148 | CHMe | 1 | $CH_2$ | CHMe | NMe | CO |
| 2.149 | CHMe | 1 | $CH_2$ | CHMe | NCOMe | CO |
| 2.150 | CHMe | 1 | $CH_2$ | CHMe | NCOEt | CO |
| 2.151 | CHMe | 1 | $CH_2$ | CHMe | NCOnPr | CO |
| 2.152 | CHMe | 1 | $CH_2$ | CHMe | $NCOCH_2OMe$ | CO |
| 2.153 | CHMe | 1 | $CH_2$ | CHMe | $NCOCHMe_2$ | CO |
| 2.154 | CHMe | 0 | | CHEt | NH | CO |
| 2.155 | CHMe | 0 | | CHEt | NMe | CO |
| 2.156 | CHMe | 0 | | CHEt | NCOMe | CO |
| 2.157 | CHMe | 0 | | CHEt | NCOEt | CO |
| 2.158 | CHMe | 0 | | CHEt | NCOnPr | CO |
| 2.159 | CHMe | 0 | | CHEt | $NCOCH_2OMe$ | CO |
| 2.160 | CHMe | 0 | | CHEt | $NCOCHMe_2$ | CO |
| 2.161 | CHMe | 1 | $CH_2$ | CHEt | NH | CO |
| 2.162 | CHMe | 1 | $CH_2$ | CHEt | NMe | CO |
| 2.163 | CHMe | 1 | $CH_2$ | CHEt | NCOMe | CO |
| 2.164 | CHMe | 1 | $CH_2$ | CHEt | NCOEt | CO |
| 2.165 | CHMe | 1 | $CH_2$ | CHEt | NCOnPr | CO |
| 2.166 | CHMe | 1 | $CH_2$ | CHEt | $NCOCH_2OMe$ | CO |
| 2.167 | CHMe | 1 | $CH_2$ | CHEt | $NCOCHMe_2$ | CO |
| 2.168 | $CHCH_2OMe$ | 0 | | $CH_2$ | NH | CO |
| 2.169 | $CHCH_2OMe$ | 1 | $CH_2$ | $CH_2$ | NH | CO |
| 2.170 | CHtBu | 0 | | $CH_2$ | NH | CO |

TABLE 2-continued

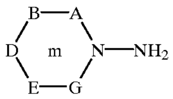

| Comp. | A | m | B | D | E | G |
|---|---|---|---|---|---|---|
| 2.171 | CHtBu | 1 | $CH_2$ | $CH_2$ | NH | CO |
| 2.172 | CHiPr | 0 | | $CH_2$ | NH | CO |
| 2.173 | CHiPr | 1 | $CH_2$ | $CH_2$ | NH | CO |
| 2.174 | CHiPr | 0 | | $CH_2$ | NH | CO |
| 2.175 | CHiPr | 0 | | $CH_2$ | NMe | CO |
| 2.176 | CHiPr | 0 | | $CH_2$ | NCOMe | CO |
| 2.177 | CHiPr | 0 | | $CH_2$ | NCOEt | CO |
| 2.178 | CHiPr | 0 | | $CH_2$ | NCOnPr | CO |
| 2.179 | CHiPr | 0 | | $CH_2$ | $NCOCH_2OMe$ | CO |
| 2.180 | CHiPr | 0 | | $CH_2$ | $NCOCHMe_2$ | CO |
| 2.181 | CHiPr | 1 | $CH_2$ | $CH_2$ | NH | CO |
| 2.182 | CHiPr | 1 | $CH_2$ | $CH_2$ | NMe | CO |
| 2.183 | CHiPr | 1 | $CH_2$ | $CH_2$ | NCOMe | CO |
| 2.184 | CHiPr | 1 | $CH_2$ | $CH_2$ | NCOEt | CO |
| 2.185 | CHiPr | 1 | $CH_2$ | $CH_2$ | NCOnPr | CO |
| 2.186 | CHiPr | 1 | $CH_2$ | $CH_2$ | $NCOCH_2OMe$ | CO |
| 2.187 | CHiPr | 1 | $CH_2$ | $CH_2$ | $NCOCHMe_2$ | CO |
| 2.188 | CHiPr | 0 | | CHMe | NH | CO |
| 2.189 | CHiPr | 0 | | CHMe | NMe | CO |
| 2.190 | CHiPr | 0 | | CHMe | NCOMe | CO |
| 2.191 | CHiPr | 0 | | CHMe | NCOEt | CO |
| 2.192 | CHiPr | 0 | | CHMe | NCOnPr | CO |
| 2.193 | CHiPr | 0 | | CHMe | $NCOCH_2OMe$ | CO |
| 2.194 | CHiPr | 0 | | CHMe | $NCOCHMe_2$ | CO |
| 2.195 | CHiPr | 1 | $CH_2$ | CHMe | NH | CO |
| 2.196 | CHiPr | 1 | $CH_2$ | CHMe | NMe | CO |
| 2.197 | CHiPr | 1 | $CH_2$ | CHMe | NCOMe | CO |
| 2.198 | CHiPr | 1 | $CH_2$ | CHMe | NCOEt | CO |
| 2.199 | CHiPr | 1 | $CH_2$ | CHMe | NCOnPr | CO |
| 2.200 | CHiPr | 1 | $CH_2$ | CHMe | $NCOCH_2OMe$ | CO |
| 2.201 | CHiPr | 1 | $CH_2$ | CHMe | $NCOCHMe_2$ | CO |
| 2.202 | CHiPr | 0 | | CHEt | NH | CO |
| 2.203 | CHiPr | 0 | | CHEt | NMe | CO |
| 2.204 | CHiPr | 0 | | CHEt | NCOMe | CO |
| 2.205 | CHiPr | 0 | | CHEt | NCOEt | CO |
| 2.206 | CHiPr | 0 | | CHEt | NCOnPr | CO |
| 2.207 | CHiPr | 0 | | CHEt | $NCOCH_2OMe$ | CO |
| 2.208 | CHiPr | 0 | | CHEt | $NCOCHMe_2$ | CO |
| 2.209 | CHiPr | 1 | $CH_2$ | CHEt | NH | CO |
| 2.210 | CHiPr | 1 | $CH_2$ | CHEt | NMe | CO |
| 2.211 | CHiPr | 1 | $CH_2$ | CHEt | NCOMe | CO |
| 2.212 | CHiPr | 1 | $CH_2$ | CHEt | NCOEt | CO |
| 2.213 | CHiPr | 1 | $CH_2$ | CHEt | NCOnPr | CO |
| 2.214 | CHiPr | 1 | $CH_2$ | CHEt | $NCOCH_2OMe$ | CO |
| 2.215 | CHiPr | 1 | $CH_2$ | CHEt | $NCOCHMe_2$ | CO |
| 2.216 | CHcPr | 0 | | $CH_2$ | NH | CO |
| 2.217 | CHcPr | 1 | $CH_2$ | $CH_2$ | NH | CO |
| 2.218 | CHEt | 0 | | $CH_2$ | NH | CO |
| 2.219 | CHEt | 1 | $CH_2$ | $CH_2$ | NH | CO |
| 2.220 | CHEt | 0 | | $CH_2$ | NH | CO |
| 2.221 | CHEt | 0 | | $CH_2$ | NMe | CO |
| 2.222 | CHEt | 0 | | $CH_2$ | NCOMe | CO |
| 2.223 | CHEt | 0 | | $CH_2$ | NCOEt | CO |
| 2.224 | CHEt | 0 | | $CH_2$ | NCOnPr | CO |
| 2.225 | CHEt | 0 | | $CH_2$ | $NCOCH_2OMe$ | CO |
| 2.226 | CHEt | 0 | | $CH_2$ | $NCOCHMe_2$ | CO |
| 2.227 | CHEt | 1 | $CH_2$ | $CH_2$ | NH | CO |
| 2.228 | CHEt | 1 | $CH_2$ | $CH_2$ | NMe | CO |
| 2.229 | CHEt | 1 | $CH_2$ | $CH_2$ | NCOMe | CO |
| 2.230 | CHEt | 1 | $CH_2$ | $CH_2$ | NCOEt | CO |
| 2.231 | CHEt | 1 | $CH_2$ | $CH_2$ | NCOnPr | CO |
| 2.232 | CHEt | 1 | $CH_2$ | $CH_2$ | $NCOCH_2OMe$ | CO |
| 2.233 | CHEt | 1 | $CH_2$ | $CH_2$ | $NCOCHMe_2$ | CO |
| 2.234 | CHEt | 0 | | CHMe | NH | CO |
| 2.235 | CHEt | 0 | | CHMe | NMe | CO |
| 2.236 | CHEt | 0 | | CHMe | NCOMe | CO |
| 2.237 | CHEt | 0 | | CHMe | NCOEt | CO |
| 2.238 | CHEt | 0 | | CHMe | NCOnPr | CO |
| 2.239 | CHEt | 0 | | CHMe | $NCOCH_2OMe$ | CO |
| 2.240 | CHEt | 0 | | CHMe | $NCOCHMe_2$ | CO |
| 2.241 | CHEt | 1 | $CH_2$ | CHMe | NH | CO |

TABLE 2-continued

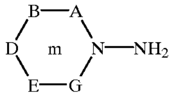

| Comp. | A | m | B | D | E | G |
|---|---|---|---|---|---|---|
| 2.242 | CHEt | 1 | CH$_2$ | CHMe | NMe | CO |
| 2.243 | CHEt | 1 | CH$_2$ | CHMe | NCOMe | CO |
| 2.244 | CHEt | 1 | CH$_2$ | CHMe | NCOEt | CO |
| 2.245 | CHEt | 1 | CH$_2$ | CHMe | NCOnPr | CO |
| 2.246 | CHEt | 1 | CH$_2$ | CHMe | NCOCH$_2$OMe | CO |
| 2.247 | CHEt | 1 | CH$_2$ | CHMe | NCOCHMe$_2$ | CO |
| 2.248 | CHEt | 0 | | CHEt | NH | CO |
| 2.249 | CHEt | 0 | | CHEt | NMe | CO |
| 2.250 | CHEt | 0 | | CHEt | NCOMe | CO |
| 2.251 | CHEt | 0 | | CHEt | NCOEt | CO |
| 2.252 | CHEt | 0 | | CHEt | NCOnPr | CO |
| 2.253 | CHEt | 0 | | CHEt | NCOCH$_2$OMe | CO |
| 2.254 | CHEt | 0 | | CHEt | NCOCHMe$_2$ | CO |
| 2.255 | CHEt | 1 | CH$_2$ | CHEt | NH | CO |
| 2.256 | CHEt | 1 | CH$_2$ | CHEt | NMe | CO |
| 2.257 | CHEt | 1 | CH$_2$ | CHEt | NCOMe | CO |
| 2.258 | CHEt | 1 | CH$_2$ | CHEt | NCOEt | CO |
| 2.259 | CHEt | 1 | CH$_2$ | CHEt | NCOnPr | CO |
| 2.260 | CHEt | 1 | CH$_2$ | CHEt | NCOCH$_2$OMe | CO |
| 2.261 | CHEt | 1 | CH$_2$ | CHEt | NCOCHMe$_2$ | CO |
| 2.262 | CSMe= | 1 | N= | CO | NMe | CO |
| 2.263 | CNHCOOEt= | 0 | | N= | NH | CS |
| 2.264 | CNHCOOMe= | 0 | | N= | NH | CS |
| 2.265 | CNHMe= | 1 | N= | CO | NMe | CO |
| 2.266 | CMe$_2$ | 0 | | CO | NH | CO |
| 2.267 | CMe$_2$ | 1 | CH$_2$ | CO | NH | CO |
| 2.268 | CMe$_2$ | 0 | | CH$_2$ | NH | CO |
| 2.269 | CMe$_2$ | 1 | CH$_2$ | CH$_2$ | NH | CO |
| 2.270 | CMe= | 0 | | CCOOEt= | S | CNH |
| 2.271 | CMe= | 0 | | N= | NH | CS |
| 2.272 | CMe= | 0 | | N= | NH | CO |
| 2.274 | CMe= | 1 | CH= | NH | NH | CO |
| 2.275 | CMe= | 0 | | CH= | S | CNH |
| 2.276 | CHMe | 0 | | CH$_2$ | NH | CO |
| 2.277 | CMe= | 1 | CH= | CH$_2$ | NH | CO |
| 2.278 | CCH$_2$OMe= | 0 | | N= | NH | CS |
| 2.279 | CCH$_2$OEt= | 0 | | N= | NH | CS |
| 2.280 | CCH$_2$iPr= | 0 | | N= | NH | CS |
| 2.281 | CCF$_3$= | 0 | | N= | NH | CS |
| 2.282 | CcHex= | 0 | | N= | NH | CS |
| 2.283 | CiPr= | 0 | | N= | NH | CS |
| 2.284 | CcPr= | 0 | | N= | NH | CS |
| 2.285 | CEt= | 0 | | N= | NH | CS |
| 2.286 | CEt= | 0 | | N= | NH | CO |
| 2.287 | CC$_2$F$_5$= | 0 | | N= | NH | CS |
| 2.288 | CBr= | 0 | | N= | NH | CS |
| 2.289 | C(=NH) | 0 | | CMe$_2$ | NH | CO |
| 2.290 | C(=NH) | 1 | CH= | CMe= | NH | CO |
| 2.291 | CH$_2$ | 1 | CHMe | NH | NH | CO |
| 2.292 | CH$_2$ | 1 | CHEt | NH | NH | CO |
| 2.293 | CH$_2$ | 1 | CHcPr | NH | NH | CO |
| 2.294 | CH$_2$ | 1 | CHtBu | NH | NH | CO |
| 2.295 | CH$_2$ | 1 | CHCH$_2$OMe | NH | NH | CO |
| 2.296 | CHMe | 1 | CHMe | NH | NH | CO |
| 2.297 | CHMe | 1 | CHEt | NH | NH | CO |
| 2.298 | CHMe | 1 | CHcPr | NH | NH | CO |
| 2.299 | CHMe | 1 | CHtBu | NH | NH | CO |
| 2.300 | CHMe | 1 | CHCH$_2$OMe | NH | NH | CO |
| 2.301 | CMe$_2$ | 1 | CHMe | NH | NH | CO |
| 2.302 | CMe$_2$ | 1 | CHEt | NH | NH | CO |
| 2.303 | CMe$_2$ | 1 | CHcPr | NH | NH | CO |
| 2.304 | CMe$_2$ | 1 | CHtBu | NH | NH | CO |
| 2.305 | CMe$_2$ | 1 | CHCH$_2$OMe | NH | NH | CO |
| 2.306 | CH$_2$ | 1 | CHMe | NCOMe | NCOMe | CO |
| 2.307 | CH$_2$ | 1 | CHMe | NCOCH$_2$OMe | NCOCH$_2$OMe | CO |
| 2.308 | CH$_2$ | 1 | CHMe | NCOcPr | NCOcPr | CO |
| 2.309 | CH$_2$ | 1 | CHMe | NCOCH$_2$C1 | NCOCH$_2$Cl | CO |
| 2.310 | CH$_2$ | 1 | CHMe | NCOEt | NCOEt | CO |
| 2.311 | CH$_2$ | 1 | CHMe | NCOCHMe$_2$ | NCOCHMe$_2$ | CO |
| 2.312 | CH$_2$ | 1 | CHMe | NCOOEt | NCOOEt | CO |
| 2.313 | CH$_2$ | 1 | CHMe | NCOMe | NH | CO |

TABLE 2-continued

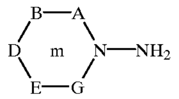

| Comp. | A | m | B | D | E | G |
|---|---|---|---|---|---|---|
| 2.314 | $CH_2$ | 1 | CHMe | $NCOCH_2OMe$ | NH | CO |
| 2.315 | $CH_2$ | 1 | CHMe | NCO-cPr | NH | CO |
| 2.316 | $CH_2$ | 1 | CHMe | $NCOCH_2Cl$ | NH | CO |
| 2.317 | $CH_2$ | 1 | CHMe | NCOEt | NH | CO |
| 2.318 | $CH_2$ | 1 | CHMe | $NCOCHMe_2$ | NH | CO |
| 2.319 | $CH_2$ | 1 | CHMe | NCOOEt | NH | CO |
| 2.320 | CH= | 0 | | C(Me)= | N(—N=CH-3-pyridinyl) | CO |
| 2.321 | $CH_2$ | 0 | | C(Me)(OH) | N(—N=CH-3-pyridinyl) | CO |

TABLE 2a melting points of compounds from Table 2

| Comp. | m.p.(°) |
|---|---|
| 2.001 | 207 |
| 2.003 | solid |
| 2.004 | 137–139 |
| 2.005 | 142–143 |
| 2.006 | 160 |
| 2.008 | 192–193 |
| 2.009 | 154 |
| 2.010 | 212–213 |
| 2.013 | >250 |
| 2.019 | 153–154 |
| 2.020 | 50–51 |
| 2.021 | 123–124 |
| 2.030 | 176 |
| 2.032 | 115–116 |
| 2.040 | 64–68 |
| 2.072 | solid |
| 2.074 | 162–164 |
| 2.080 | solid |
| 2.114 | 81 |
| 2.115 | 164–166 |
| 2.116 | 228 |
| 2.117 | 186–188 |
| 2.121 | 115–119 |
| 2.122 | solid |
| 2.123 | 196–200 |
| 2.138 | solid |
| 2.139 | solid |
| 2.262 | 169 |
| 2.263 | 220–222 |
| 2.265 | 220–221 |
| 2.271 | solid |
| 2.272 | 225–230 |
| 2.275 | 169 |
| 2.276 | solid |
| 2.277 | solid |
| 2.278 | 105 |
| 2.279 | 115 |
| 2.280 | 60 |
| 2.281 | 140 |
| 2.282 | 105 |
| 2.283 | 118 |
| 2.284 | 181 |
| 2.285 | 150 |
| 2.286 | solid |
| 2.287 | 142 |
| 2.288 | 135 |
| 2.289 | >250 |
| 2.290 | 190–193 |

TABLE 3

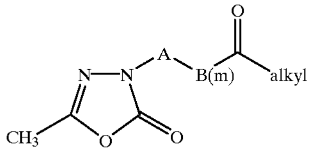

| Comp. | A | m | B | alkyl |
|---|---|---|---|---|
| 3.01 | CO | 1 | $CH_2$ | Me |
| 3.02 | CO | 1 | $CH_2$ | Et |
| 3.03 | CO | 1 | $CMe_2$ | Me |
| 3.04 | CO | 1 | $CMe_2$ | Et |
| 3.05 | CO | 0 | | Me |
| 3.06 | CO | 0 | | Et |
| 3.07 | $CH_2$ | 1 | CHOH | Me |
| 3.08 | $CH_2$ | 1 | O | Me |
| 3.09 | $CH_2$ | 1 | NMe | Me |
| 3.10 | $CH_2$ | 1 | CO | Me |
| 3.11 | $CH_2$ | 1 | $CH_2$ | Et |
| 3.12 | $CH_2$ | 1 | $CH_2$ | Me |
| 3.13 | $CH_2$ | 1 | $CH_2$ | nPr |
| 3.14 | $CH_2$ | 1 | $CH_2$ | Et |
| 3.15 | $CH_2$ | 1 | $CH_2$ | nBu |
| 3.16 | $CH_2$ | 1 | $C(OMe)_2$ | Me |
| 3.17 | $CH_2$ | 1 | $C(OEt)_2$ | Me |
| 3.18 | $CH_2$ | 1 | $CMe_2$ | Me |
| 3.19 | $CH_2$ | 1 | $CMe_2$ | Et |
| 3.20 | $CH_2$ | 1 | $CMe_2$ | nPr |
| 3.21 | $CH_2$ | 1 | CHMe | Me |
| 3.22 | $CH_2$ | 1 | $C(CH_2OH)_2$ | Me |
| 3.23 | $CH_2$ | 1 | CHEt | Me |
| 3.24 | $CH_2$ | 0 | | Me |
| 3.25 | $CH_2$ | 0 | | Et |
| 3.26 | $CH_2$ | 0 | | nPr |
| 3.27 | $CH_2$ | 1 | $CH_2$ | Me |
| 3.28 | $CH_2$ | 1 | $CH_2$ | Et |
| 3.29 | CH= | 1 | CMe= | Me |
| 3.30 | CH= | 1 | CEt= | Me |
| 3.31 | $CH_2$ | 0 | | Me |
| 3.32 | $CH_2$ | 0 | | Et |
| 3.33 | CHMe | 1 | $CH_2$ | Me |
| 3.34 | CHMe | 1 | $CH_2$ | Et |
| 3.35 | CHMe | 0 | | Me |
| 3.36 | CHMe | 0 | | Et |
| 3.37 | $CHCH_2OMe$ | 0 | | Me |
| 3.38 | $CHCH_2OMe$ | 1 | $CH_2$ | Me |
| 3.39 | CHtBu | 0 | | Me |
| 3.40 | CHtBu | 1 | $CH_2$ | Me |
| 3.41 | CHiPr | 1 | $CH_2$ | Me |
| 3.42 | CHiPr | 1 | $CH_2$ | Et |
| 3.43 | CHiPr | 0 | | Me |
| 3.44 | CHiPr | 0 | | Et |

TABLE 3-continued

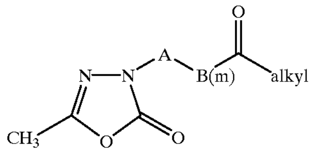

| Comp. | A | m | B | alkyl |
|---|---|---|---|---|
| 3.45 | CHcPr | 0 | | Me |
| 3.46 | CHcPr | 1 | $CH_2$ | Me |
| 3.47 | CHEt | 1 | $CH_2$ | Me |
| 3.48 | CHEt | 1 | $CH_2$ | Et |
| 3.49 | CHEt | 0 | | Me |
| 3.50 | CHEt | 0 | | Et |
| 3.51 | $CMe_2$ | 1 | $CH_2$ | Me |
| 3.52 | $CMe_2$ | 1 | $CH_2$ | Et |
| 3.53 | $CH_2$ | 0 | | nPr |
| 3.54 | $CH_2$ | 0 | | nBu |

TABLE 3a

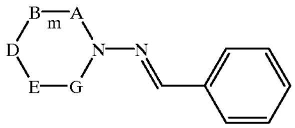

| No. | A | m | B | D | E | G |
|---|---|---|---|---|---|---|
| a.001 | CS | 0 | | NH | NH | CS |
| a.002 | CS | 0 | | NH | NH | CO |
| a.003 | CO | 1 | CMe═ | N═ | NH | CS |
| a.004 | CO | 1 | $C(C_2H_4iPr)$═ | N═ | NH | CS |
| a.005 | CO | 1 | $C(CH_2iPr)$═ | N═ | NH | CS |
| a.006 | CO | 1 | CtBu═ | N═ | NH | CS |
| a.007 | CO | 1 | CtBu═ | N═ | NH | CO |
| a.008 | CO | 1 | CcPr═ | N═ | NH | CS |
| a.009 | CO | 1 | CcHex═ | N═ | NH | CS |
| a.010 | CO | 1 | $NCH_2cHex$ | CO | NH | CO |
| a.011 | CO | 1 | $CH_2$ | CO | NH | CO |
| a.012 | CO | 1 | $CH_2$ | $CH_2$ | NH | CO |
| a.013 | CO | 1 | $CH_2$ | $CMe_2$ | NH | CO |
| a.014 | CO | 1 | CH═ | CMe═ | NH | CO |
| a.015 | CO | 1 | CH═ | N═ | NH | CS |
| a.016 | CO | 1 | CH═ | $CCF_3$═ | NH | CNH |
| a.017 | CO | 1 | $CMe_2$ | CO | NH | CO |
| a.018 | CO | 1 | $CMe_2$ | $CH_2$ | NH | CO |
| a.019 | CO | 1 | CMe═ | N═ | NH | CO |
| a.020 | CO | 1 | CtBu═ | N═ | $NCH_2CH_2F$ | CS |
| a.021 | CO | 1 | CEt═ | N═ | NH | CS |
| a.022 | CO | 0 | | CO | NH | CO |
| a.023 | CO | 0 | | NH | NH | CO |
| a.024 | CO | 0 | | $CH_2$ | S | CS |
| a.025 | CO | 0 | | $CHCH_2COOMe$ | NH | CS |
| a.026 | CO | 0 | | $CHC_2H_4COOMe$ | NH | CS |
| a.027 | CO | 0 | | NH | NH | CO |
| a.028 | CO | 0 | | $CMeCH{=}CMe_2$ | NH | CO |
| a.029 | CO | 0 | | $CMeCH_2CMe_2$ | NH | CO |
| a.030 | CO | 0 | | $CH_2$ | NH | CS |
| a.031 | CO | 0 | | $CMe_2$ | NH | CO |
| a.032 | $CH_2$ | 0 | | CO | NMe | CS |
| a.033 | $CH_2$ | 0 | | CO | NiPr | CS |
| a.034 | $CH_2$ | 0 | | CO | NEt | CS |
| a.035 | $CH_2$ | 0 | | CO | NH | CO |
| a.036 | $CH_2$ | 0 | | CO | NH | CS |
| a.037 | $CH_2$ | 1 | $CMe_2$ | CO | NH | CO |
| a.038 | $CH_2$ | 0 | | CO | NH | CO |
| a.039 | $CH_2$ | 1 | $CH_2$ | CO | NH | CO |
| a.040 | $CH_2$ | 0 | | $CH_2$ | O | CO |
| a.041 | $CH_2$ | 0 | | $CH_2$ | NH | CO |

TABLE 3a-continued

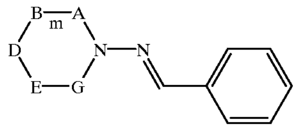

| No. | A | m | B | D | E | G |
|---|---|---|---|---|---|---|
| a.042 | $CH_2$ | 0 | | $CH_2$ | NH | CS |
| a.043 | $CH_2$ | 0 | | $CH_2$ | $CH_2$ | CO |
| a.044 | $CH_2$ | 0 | | $CH_2$ | NH | CO |
| a.045 | $CH_2$ | 0 | | $CH_2$ | NH | CO |
| a.046 | $CH_2$ | 1 | $CH_2$ | $CH_2$ | NH | CO |
| a.047 | $CH_2$ | 1 | $CMe_2$ | $CH_2$ | NH | CO |
| a.048 | $CH_2$ | 1 | $CMe_2$ | $CH_2$ | NH | CO |
| a.049 | $CH_2$ | 1 | $C(OMe)_2$ | $CH_2$ | NH | CO |
| a.050 | $CH_2$ | 1 | $C(OEt)_2$ | $CH_2$ | NH | CO |
| a.051 | $CH_2$ | 1 | $C(CH_2OH)_2$ | $CH_2$ | NH | CO |
| a.052 | $CH_2$ | 1 | CO | $CH_2$ | NH | CO |
| a.053 | $CH_2$ | 1 | CHOH | $CH_2$ | NH | CO |
| a.054 | $CH_2$ | 1 | O | $CH_2$ | NH | CO |
| a.055 | $CH_2$ | 1 | NMe | $CH_2$ | NH | CO |
| a.056 | $CH_2$ | 0 | | $CH_2$ | NH | CO |
| a.057 | $CH_2$ | 0 | | $CH_2$ | NMe | CO |
| a.058 | $CH_2$ | 0 | | $CH_2$ | NCOMe | CO |
| a.059 | $CH_2$ | 0 | | $CH_2$ | NCOEt | CO |
| a.060 | $CH_2$ | 0 | | $CH_2$ | NCOnPr | CO |
| a.061 | $CH_2$ | 0 | | $CH_2$ | $NCOCH_2OMe$ | CO |
| a.062 | $CH_2$ | 0 | | $CH_2$ | $NCOCHMe_2$ | CO |
| a.063 | $CH_2$ | 1 | $CH_2$ | $CH_2$ | NH | CO |
| a.064 | $CH_2$ | 1 | $CH_2$ | $CH_2$ | NH | CO |
| a.065 | $CH_2$ | 1 | $CH_2$ | $CH_2$ | NMe | CO |
| a.066 | $CH_2$ | 1 | $CH_2$ | $CH_2$ | NCOMe | CO |
| a.067 | $CH_2$ | 1 | $CH_2$ | $CH_2$ | NCOEt | CO |
| a.068 | $CH_2$ | 1 | $CH_2$ | $CH_2$ | NCOnPr | CO |
| a.069 | $CH_2$ | 1 | $CH_2$ | $CH_2$ | $NCOCH_2OMe$ | CO |
| a.070 | $CH_2$ | 1 | $CH_2$ | $CH_2$ | $NCOCHMe_2$ | CO |
| a.071 | $CH_2$ | 1 | CH═ | CH═ | NH | CO |
| a.072 | $CH_2$ | 0 | | CHMe | NH | CO |
| a.073 | $CH_2$ | 0 | | CHMe | NH | CO |
| a.074 | $CH_2$ | 0 | | CHMe | NMe | CO |
| a.075 | $CH_2$ | 0 | | CHMe | NCOMe | CO |
| a.076 | $CH_2$ | 0 | | CHMe | NCOEt | CO |
| a.077 | $CH_2$ | 0 | | CHMe | NCOnPr | CO |
| a.078 | $CH_2$ | 0 | | CHMe | $NCOCH_2OMe$ | CO |
| a.079 | $CH_2$ | 0 | | CHMe | $NCOCHMe_2$ | CO |
| a.080 | $CH_2$ | 1 | $CH_2$ | CHMe | NH | CO |
| a.081 | $CH_2$ | 1 | $CH_2$ | CHMe | NH | CO |
| a.082 | $CH_2$ | 1 | $CH_2$ | CHMe | NMe | CO |
| a.083 | $CH_2$ | 1 | $CH_2$ | CHMe | NCOMe | CO |
| a.084 | $CH_2$ | 1 | $CH_2$ | CHMe | NCOEt | CO |
| a.085 | $CH_2$ | 1 | $CH_2$ | CHMe | NCOnPr | CO |
| a.086 | $CH_2$ | 1 | $CH_2$ | CHMe | $NCOCH_2OMe$ | CO |
| a.087 | $CH_2$ | 1 | $CH_2$ | CHMe | $NCOCHMe_2$ | CO |
| a.088 | $CH_2$ | 0 | | $CHCH_2OMe$ | NH | CO |
| a.089 | $CH_2$ | 1 | $CH_2$ | $CHCH_2OMe$ | NH | CO |
| a.090 | $CH_2$ | 0 | | CHtBu | NH | CO |
| a.091 | $CH_2$ | 1 | $CH_2$ | CHtBu | NH | CO |
| a.092 | $CH_2$ | 0 | | CHiPr | NH | CO |
| a.093 | $CH_2$ | 1 | $CH_2$ | CHiPr | NH | CO |
| a.094 | $CH_2$ | 0 | | CHcPr | NH | CO |
| a.095 | $CH_2$ | 1 | $CH_2$ | CHcPr | NH | CO |
| a.096 | $CH_2$ | 0 | | CHEt | NH | CO |
| a.097 | $CH_2$ | 0 | | CHEt | NH | CO |
| a.098 | $CH_2$ | 0 | | CHEt | NMe | CO |
| a.099 | $CH_2$ | 0 | | CHEt | NCOMe | CO |
| a.100 | $CH_2$ | 0 | | CHEt | NCOEt | CO |
| a.101 | $CH_2$ | 0 | | CHEt | NCOnPr | CO |
| a.102 | $CH_2$ | 0 | | CHEt | $NCOCH_2OMe$ | CO |
| a.103 | $CH_2$ | 0 | | CHEt | $NCOCHMe_2$ | CO |
| a.104 | $CH_2$ | 1 | $CH_2$ | CHEt | NH | CO |
| a.105 | $CH_2$ | 1 | $CH_2$ | CHEt | NH | CO |
| a.106 | $CH_2$ | 1 | $CH_2$ | CHEt | NMe | CO |
| a.107 | $CH_2$ | 1 | $CH_2$ | CHEt | NCOMe | CO |
| a.108 | $CH_2$ | 1 | $CH_2$ | CHEt | NCOEt | CO |
| a.109 | $CH_2$ | 1 | $CH_2$ | CHEt | NCOnPr | CO |
| a.110 | $CH_2$ | 1 | $CH_2$ | CHEt | $NCOCH_2OMe$ | CO |

TABLE 3a-continued

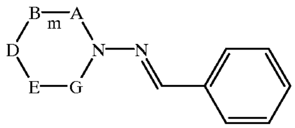

| No. | A | m | B | D | E | G |
|---|---|---|---|---|---|---|
| a.111 | $CH_2$ | 1 | $CH_2$ | CHEt | $NCOCHMe_2$ | CO |
| a.112 | $CH_2$ | 1 | CMe= | CH= | NH | CO |
| a.113 | $CH_2$ | 1 | CEt= | CH= | NH | CO |
| a.114 | $CH_2$ | 1 | CH= | CtBu= | NMe | CO |
| a.115 | CH= | 0 | | N= | $NCOCH_3$ | CO |
| a.116 | CH= | 0 | | N= | $NCONMe_2$ | CNH |
| a.117 | CH= | 0 | | N= | NH | CO |
| a.118 | CH= | 1 | CH= | NH | NH | CO |
| a.119 | CH= | 1 | CMe= | $CH_2$ | NH | CO |
| a.120 | CH= | 1 | CEt= | $CH_2$ | NH | CO |
| a.121 | CH= | 0 | | CMe= | NH | CO |
| a.122 | CH= | 1 | CH= | CHMe | NH | CO |
| a.123 | CH= | 0 | | CtBu= | NH | CO |
| a.124 | CHMe | 0 | | $CH_2$ | NH | CO |
| a.125 | CHMe | 0 | | $CH_2$ | NMe | CO |
| a.126 | CHMe | 0 | | $CH_2$ | NCOMe | CO |
| a.127 | CHMe | 0 | | $CH_2$ | NCOEt | CO |
| a.128 | CHMe | 0 | | $CH_2$ | NCOnPr | CO |
| a.129 | CHMe | 0 | | $CH_2$ | $NCOCH_2OMe$ | CO |
| a.130 | CHMe | 0 | | $CH_2$ | $NCOCHMe_2$ | CO |
| a.131 | CHMe | 1 | $CH_2$ | $CH_2$ | NH | CO |
| a.132 | CHMe | 1 | $CH_2$ | $CH_2$ | NMe | CO |
| a.133 | CHMe | 1 | $CH_2$ | $CH_2$ | NCOMe | CO |
| a.134 | CHMe | 1 | $CH_2$ | $CH_2$ | NCOEt | CO |
| a.135 | CHMe | 1 | $CH_2$ | $CH_2$ | NCOnPr | CO |
| a.136 | CHMe | 1 | $CH_2$ | $CH_2$ | $NCOCH_2OMe$ | CO |
| a.137 | CHMe | 1 | $CH_2$ | $CH_2$ | $NCOCHMe_2$ | CO |
| a.138 | CMe= | 0 | | CH= | $NCH_3$ | CO |
| a.139 | CHMe | 1 | CH= | CH= | NH | CO |
| a.140 | CHMe | 0 | | CHMe | NH | CO |
| a.141 | CHMe | 0 | | CHMe | NMe | CO |
| a.142 | CHMe | 0 | | CHMe | NCOMe | CO |
| a.143 | CHMe | 0 | | CHMe | NCOEt | CO |
| a.144 | CHMe | 0 | | CHMe | NCOnPr | CO |
| a.145 | CHMe | 0 | | CHMe | $NCOCH_2OMe$ | CO |
| a.146 | CHMe | 0 | | CHMe | $NCOCHMe_2$ | CO |
| a.147 | CHMe | 1 | $CH_2$ | CHMe | NH | CO |
| a.148 | CHMe | 1 | $CH_2$ | CHMe | NMe | CO |
| a.149 | CHMe | 1 | $CH_2$ | CHMe | NCOMe | CO |
| a.150 | CHMe | 1 | $CH_2$ | CHMe | NCOEt | CO |
| a.151 | CHMe | 1 | $CH_2$ | CHMe | NCOnPr | CO |
| a.152 | CHMe | 1 | $CH_2$ | CHMe | $NCOCH_2OMe$ | CO |
| a.153 | CHMe | 1 | $CH_2$ | CHMe | $NCOCHMe_2$ | CO |
| a.154 | CHMe | 0 | | CHEt | NH | CO |
| a.155 | CHMe | 0 | | CHEt | NMe | CO |
| a.156 | CHMe | 0 | | CHEt | NCOMe | CO |
| a.157 | CHMe | 0 | | CHEt | NCOEt | CO |
| a.158 | CHMe | 0 | | CHEt | NCOnPr | CO |
| a.159 | CHMe | 0 | | CHEt | $NCOCH_2OMe$ | CO |
| a.160 | CHMe | 0 | | CHEt | $NCOCHMe_2$ | CO |
| a.161 | CHMe | 1 | $CH_2$ | CHEt | NH | CO |
| a.162 | CHMe | 1 | $CH_2$ | CHEt | NMe | CO |
| a.163 | CHMe | 1 | $CH_2$ | CHEt | NCOMe | CO |
| a.164 | CHMe | 1 | $CH_2$ | CHEt | NCOEt | CO |
| a.165 | CHMe | 1 | $CH_2$ | CHEt | NCOnPr | CO |
| a.166 | CHMe | 1 | $CH_2$ | CHEt | $NCOCH_2OMe$ | CO |
| a.167 | CHMe | 1 | $CH_2$ | CHEt | $NCOCHMe_2$ | CO |
| a.168 | $CHCH_2OMe$ | 0 | | $CH_2$ | NH | CO |
| a.169 | $CHCH_2OMe$ | 1 | $CH_2$ | $CH_2$ | NH | CO |
| a.170 | CHtBu | 0 | | $CH_2$ | NH | CO |
| a.171 | CHtBu | 1 | $CH_2$ | $CH_2$ | NH | CO |
| a.172 | CHiPr | 0 | | $CH_2$ | NH | CO |
| a.173 | CHiPr | 1 | $CH_2$ | $CH_2$ | NH | CO |
| a.174 | CHiPr | 0 | | $CH_2$ | NH | CO |
| a.175 | CHiPr | 0 | | $CH_2$ | NMe | CO |
| a.176 | CHiPr | 0 | | $CH_2$ | NCOMe | CO |
| a.177 | CHiPr | 0 | | $CH_2$ | NCOEt | CO |
| a.178 | CHiPr | 0 | | $CH_2$ | NCOnPr | CO |
| a.179 | CHiPr | 0 | | $CH_2$ | $NCOCH_2OMe$ | CO |

TABLE 3a-continued

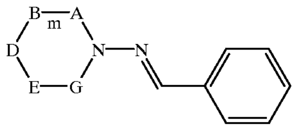

| No. | A | m | B | D | E | G |
|---|---|---|---|---|---|---|
| a.180 | CHiPr | 0 | | $CH_2$ | $NCOCHMe_2$ | CO |
| a.181 | CHiPr | 1 | $CH_2$ | $CH_2$ | NH | CO |
| a.182 | CHiPr | 1 | $CH_2$ | $CH_2$ | NMe | CO |
| a.183 | CHiPr | 1 | $CH_2$ | $CH_2$ | NCOMe | CO |
| a.184 | CHiPr | 1 | $CH_2$ | $CH_2$ | NCOEt | CO |
| a.185 | CHiPr | 1 | $CH_2$ | $CH_2$ | NCOnPr | CO |
| a.186 | CHiPr | 1 | $CH_2$ | $CH_2$ | $NCOCH_2OMe$ | CO |
| a.187 | CHiPr | 1 | $CH_2$ | $CH_2$ | $NCOCHMe_2$ | CO |
| a.188 | CHiPr | 0 | | CHMe | NH | CO |
| a.189 | CHiPr | 0 | | CHMe | NMe | CO |
| a.190 | CHiPr | 0 | | CHMe | NCOMe | CO |
| a.191 | CHiPr | 0 | | CHMe | NCOEt | CO |
| a.192 | CHiPr | 0 | | CHMe | NCOnPr | CO |
| a.193 | CHiPr | 0 | | CHMe | $NCOCH_2OMe$ | CO |
| a.194 | CHiPr | 0 | | CHMe | $NCOCHMe_2$ | CO |
| a.195 | CHiPr | 1 | $CH_2$ | CHMe | NH | CO |
| a.196 | CHiPr | 1 | $CH_2$ | CHMe | NMe | CO |
| a.197 | CHiPr | 1 | $CH_2$ | CHMe | NCOMe | CO |
| a.198 | CHiPr | 1 | $CH_2$ | CHMe | NCOEt | CO |
| a.199 | CHiPr | 1 | $CH_2$ | CHMe | NCOnPr | CO |
| a.200 | CHiPr | 1 | $CH_2$ | CHMe | $NCOCH_2OMe$ | CO |
| a.201 | CHiPr | 1 | $CH_2$ | CHMe | $NCOCHMe_2$ | CO |
| a.202 | CHiPr | 0 | | CHEt | NH | CO |
| a.203 | CHiPr | 0 | | CHEt | NMe | CO |
| a.204 | CHiPr | 0 | | CHEt | NCOMe | CO |
| a.205 | CHiPr | 0 | | CHEt | NCOEt | CO |
| a.206 | CHiPr | 0 | | CHEt | NCOnPr | CO |
| a.207 | CHiPr | 0 | | CHEt | $NCOCH_2OMe$ | CO |
| a.208 | CHiPr | 0 | | CHEt | $NCOCHMe_2$ | CO |
| a.209 | CHiPr | 1 | $CH_2$ | CHEt | NH | CO |
| a.210 | CHiPr | 1 | $CH_2$ | CHEt | NMe | CO |
| a.211 | CHiPr | 1 | $CH_2$ | CHEt | NCOMe | CO |
| a.212 | CHiPr | 1 | $CH_2$ | CHEt | NCOEt | CO |
| a.213 | CHiPr | 1 | $CH_2$ | CHEt | NCOnPr | CO |
| a.214 | CHiPr | 1 | $CH_2$ | CHEt | $NCOCH_2OMe$ | CO |
| a.215 | CHiPr | 1 | $CH_2$ | CHEt | $NCOCHMe_2$ | CO |
| a.216 | CHcPr | 0 | | $CH_2$ | NH | CO |
| a.217 | CHcPr | 1 | $CH_2$ | $CH_2$ | NH | CO |
| a.218 | CHEt | 0 | | $CH_2$ | NH | CO |
| a.219 | CHEt | 1 | $CH_2$ | $CH_2$ | NH | CO |
| a.220 | CHEt | 0 | | $CH_2$ | NH | CO |
| a.221 | CHEt | 0 | | $CH_2$ | NMe | CO |
| a.222 | CHEt | 0 | | $CH_2$ | NCOMe | CO |
| a.223 | CHEt | 0 | | $CH_2$ | NCOEt | CO |
| a.224 | CHEt | 0 | | $CH_2$ | NCOnPr | CO |
| a.225 | CHEt | 0 | | $CH_2$ | $NCOCH_2OMe$ | CO |
| a.226 | CHEt | 0 | | $CH_2$ | $NCOCHMe_2$ | CO |
| a.227 | CHEt | 1 | $CH_2$ | $CH_2$ | NH | CO |
| a.228 | CHEt | 1 | $CH_2$ | $CH_2$ | NMe | CO |
| a.229 | CHEt | 1 | $CH_2$ | $CH_2$ | NCOMe | CO |
| a.230 | CHEt | 1 | $CH_2$ | $CH_2$ | NCOEt | CO |
| a.231 | CHEt | 1 | $CH_2$ | $CH_2$ | NCOnPr | CO |
| a.232 | CHEt | 1 | $CH_2$ | $CH_2$ | $NCOCH_2OMe$ | CO |
| a.233 | CHEt | 1 | $CH_2$ | $CH_2$ | $NCOCHMe_2$ | CO |
| a.234 | CHEt | 0 | | CHMe | NH | CO |
| a.235 | CHEt | 0 | | CHMe | NMe | CO |
| a.236 | CHEt | 0 | | CHMe | NCOMe | CO |
| a.237 | CHEt | 0 | | CHMe | NCOEt | CO |
| a.238 | CHEt | 0 | | CHMe | NCOnPr | CO |
| a.239 | CHEt | 0 | | CHMe | $NCOCH_2OMe$ | CO |
| a.240 | CHEt | 0 | | CHMe | $NCOCHMe_2$ | CO |
| a.241 | CHEt | 1 | $CH_2$ | CHMe | NH | CO |
| a.242 | CHEt | 1 | $CH_2$ | CHMe | NMe | CO |
| a.243 | CHEt | 1 | $CH_2$ | CHMe | NCOMe | CO |
| a.244 | CHEt | 1 | $CH_2$ | CHMe | NCOEt | CO |
| a.245 | CHEt | 1 | $CH_2$ | CHMe | NCOnPr | CO |
| a.246 | CHEt | 1 | $CH_2$ | CHMe | $NCOCH_2OMe$ | CO |
| a.247 | CHEt | 1 | $CH_2$ | CHMe | $NCOCHMe_2$ | CO |
| a.248 | CHEt | 0 | | CHEt | NH | CO |

TABLE 3a-continued

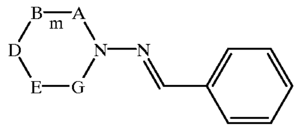

| No. | A | m | B | D | E | G |
|---|---|---|---|---|---|---|
| a.249 | CHEt | 0 | | CHEt | NMe | CO |
| a.250 | CHEt | 0 | | CHEt | NCOMe | CO |
| a.251 | CHEt | 0 | | CHEt | NCOEt | CO |
| a.252 | CHEt | 0 | | CHEt | NCOnPr | CO |
| a.253 | CHEt | 0 | | CHEt | $NCOCH_2OMe$ | CO |
| a.254 | CHEt | 0 | | CHEt | $NCOCHMe_2$ | CO |
| a.255 | CHEt | 1 | $CH_2$ | CHEt | NH | CO |
| a.256 | CHEt | 1 | $CH_2$ | CHEt | NMe | CO |
| a.257 | CHEt | 1 | $CH_2$ | CHEt | NCOMe | CO |
| a.258 | CHEt | 1 | $CH_2$ | CHEt | NCOEt | CO |
| a.259 | CHEt | 1 | $CH_2$ | CHEt | NCOnPr | CO |
| a.260 | CHEt | 1 | $CH_2$ | CHEt | $NCOCH_2OMe$ | CO |
| a.261 | CHEt | 1 | $CH_2$ | CHEt | $NCOCHMe_2$ | CO |
| a.262 | C(SMe)= | 1 | N= | CO | NMe | CO |
| a.263 | C(NHCOOEt)= | 0 | | N= | NH | CS |
| a.264 | C(NHCOOMe)= | 0 | | N= | NH | CS |
| a.265 | C(NHMe)= | 1 | N= | CO | NMe | CO |
| a.266 | $CMe_2$ | 0 | | CO | NH | CO |
| a.267 | $CMe_2$ | 1 | $CH_2$ | CO | NH | CO |
| a.268 | $CMe_2$ | 0 | | $CH_2$ | NH | CO |
| a.269 | $CMe_2$ | 1 | $CH_2$ | $CH_2$ | NH | CO |
| a.270 | CMe= | 0 | | C(COOEt)= | S | CNH |
| a.271 | CMe= | 0 | | N= | NH | CS |
| a.272 | CMe= | 0 | | N= | NH | CO |
| a.273 | CMe= | 0 | | CH= | NH | CO |
| a.274 | CMe= | 1 | CH= | NH | NH | CO |
| a.275 | CMe= | 0 | | CH= | S | CNH |
| a.276 | CHMe | 0 | | $CH_2$ | NH | CO |
| a.277 | CMe= | 1 | CH= | $CH_2$ | NH | CO |
| a.278 | $C(CH_2OMe)$= | 0 | | N= | NH | CS |
| a.279 | $C(CH_2OEt)$= | 0 | | N= | NH | CS |
| a.280 | $C(CH_2iPr)$= | 0 | | N= | NH | CS |
| a.281 | $CCF_3$= | 0 | | N= | NH | CS |
| a.282 | $C(C_5H_{11})$= | 0 | | N= | NH | CS |
| a.283 | CiPr= | 0 | | N= | NH | CS |
| a.284 | CcPr= | 0 | | N= | NH | CS |
| a.285 | CEt= | 0 | | N= | NH | CS |
| a.286 | CEt= | 0 | | N= | NH | CO |
| a.287 | $C(C_2F_5)$= | 0 | | N= | NH | CS |
| a.288 | CBr= | 0 | | N= | NH | CS |
| a.289 | C(=NH) | 0 | | $CMe_2$ | NH | CO |
| a.290 | C(=NH) | 1 | CH= | CMe= | NH | CO |
| a.291 | $CH_2$ | 1 | CHMe | NH | NH | CO |
| a.292 | $CH_2$ | 1 | CHEt | NH | NH | CO |
| a.293 | $CH_2$ | 1 | CHcPr | NH | NH | CO |
| a.294 | $CH_2$ | 1 | CHtBu | NH | NH | CO |
| a.295 | $CH_2$ | 1 | $CHCH_2OMe$ | NH | NH | CO |
| a.296 | CHMe | 1 | CHMe | NH | NH | CO |
| a.297 | CHMe | 1 | CHEt | NH | NH | CO |
| a.298 | CHMe | 1 | CHcPr | NH | NH | CO |
| a.299 | CHMe | 1 | CHtBu | NH | NH | CO |
| a.300 | CHMe | 1 | $CHCH_2OMe$ | NH | NH | CO |
| a.301 | $CMe_2$ | 1 | CHMe | NH | NH | CO |
| a.302 | $CMe_2$ | 1 | CHEt | NH | NH | CO |
| a.303 | $CMe_2$ | 1 | CHCPr | NH | NH | CO |
| a.304 | $CMe_2$ | 1 | CHtBu | NH | NH | CO |
| a.305 | $CMe_2$ | 1 | $CHCH_2OMe$ | NH | NH | CO |
| a.306 | $CH_2$ | 1 | CHMe | NCOMe | NCOMe | CO |
| a.307 | $CH_2$ | 1 | CHMe | $NCOCH_2OMe$ | $NCOCH_2OMe$ | CO |
| a.308 | $CH_2$ | 1 | CHMe | NCOcPr | NCOcPr | CO |
| a.309 | $CH_2$ | 1 | CHMe | $NCOCH_2Cl$ | $NCOCH_2Cl$ | CO |
| a.310 | $CH_2$ | 1 | CHMe | NCOEt | NCOEt | CO |
| a.311 | $CH_2$ | 1 | CHMe | $NCOCHMe_2$ | $NCOCHMe_2$ | CO |
| a.312 | $CH_2$ | 1 | CHMe | NCOOEt | NCOOEt | CO |
| a.313 | $CH_2$ | 1 | CHMe | NCOMe | NH | CO |
| a.314 | $CH_2$ | 1 | CHMe | $NCOCH_2OMe$ | NH | CO |
| a.315 | $CH_2$ | 1 | CHMe | NCOcPr | NH | CO |
| a.316 | $CH_2$ | 1 | CHMe | $NCOCH_2Cl$ | NH | CO |
| a.317 | $CH_2$ | 1 | CHMe | NCOEt | NH | CO |

TABLE 3a-continued

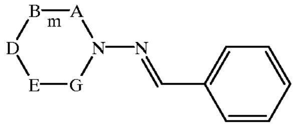

| No. | A | m | B | D | E | G |
|---|---|---|---|---|---|---|
| a.318 | $CH_2$ | 1 | CHMe | $NCOCHMe_2$ | NH | CO |
| a.319 | $CH_2$ | 1 | CHMe | NCOOEt | NH | CO |
| a.320 | CH= | 0 | | CMe= | N(N=CH-3-pyridyl) | CO |
| a.321 | $CH_2$ | 0 | | C(Me)(OH) | N(N=CH-3-pyridyl) | CO |
| a.322 | CH= | 0 | | CMe= | N(N=CH2) | CO |
| a.323 | $CH_2$ | 0 | | C(Me)(OH) | N(N=CH2) | CO |

TABLE 3b

| melting points of compounds from Table 3a | |
|---|---|
| Comp. | m.p.(°) |
| 3a.121 | 182–184 |
| 3a.273 | 189–196 |

Example P18

(4-Methyl-2-oxoimidazolidin-1-yl)acetamide (Compound 4.025 in Table 4)

1.6 g of Rh/C are added to a solution of 7.8 g of (4-methyl-2-oxo-1,3-dihydroimidazol-1-yl)acetamide in 80 ml of methanol and the reaction mixture is treated with hydrogen at 3 bar. After 30 minutes, 1.13 litres of hydrogen have been taken up and the reaction has ceased. The reaction mixture is then filtered over Celite and concentrated by evaporation. The residue is dissolved in methylene chloride, magnesium sulfate is added thereto, followed by filtration over Celite and concentration by evaporation. The residue is stirred with ether. The crystals are filtered off with suction and dried in vacuo at 60°. 7.3 g of the title compound having a melting point of 124–127° are thus obtained.

Example P19

(3,4-Dimethyl-2-oxo-1,3-dihydroimidazol-1-yl)acetamide (Compound 4.047 in Table 4)

68.5 ml of methylamine (40% in water) are added dropwise to a solution of 78 g of 5-methyl-2-oxo-3-(2-oxopropyl)-3H-1,3,4-oxadiazole in 500 ml of acetonitrile. After the slightly endothermic reaction, the orange-coloured solution is heated to 48°. After 30 minutes the reaction mixture is concentrated by evaporation. 100 ml of tetrahydrofuran and 200 ml of ethyl acetate are added to the residue, whereupon crystals precipitate. The crystals are filtered off, then washed with ethyl acetate and dried in vacuo at 60°. A mixture of title compound and (3,4-dimethyl-2-oxo-4-methylamino-1 ,3-dihydroimidazol- 1-yl)acetamide is obtained. A sample of that mixture is separated on silica gel with ethyl acetate/methanol (2:1). The title compound having a melting point of 198–201° and (3,4-dimethyl-2-oxo-4-methylamino-1,3-dihydroimidazol-1-yl)acetamide having a melting point of 150–152° (decomposition) are obtained. A sample of the above-mentioned mixture is maintained at 175° until no further evolution of methylamine gas is observed. The cooled residue is stirred with a small amount of methanol. Filtration of the suspension likewise yields the title compound having a melting point of 199–201°.

Example P20

The other compounds listed in Tables 4 and 4a can also be prepared in a manner analogous to that described in Examples P18 and P19.

TABLE 4

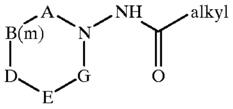

| Comp. | A | m | B | D | E | G | alkyl |
|---|---|---|---|---|---|---|---|
| 4.001. | CO | 1 | $CMe_2$ | CO | NH | CO | Me |
| 4.002. | CO | 1 | $CMe_2$ | $CH_2$ | NH | CO | Me |
| 4.003. | CO | 0 | | $CH_2$ | NH | CO | Me |
| 4.004. | CO | 1 | $CH_2$ | $CH_2$ | NH | CO | Me |
| 4.005. | CO | 0 | | $CMe_2$ | NH | CO | Me |
| 4.006. | CO | 1 | $CH_2$ | $CMe_2$ | NH | CO | Me |
| 4.007. | $CH_2$ | 1 | $CMe_2$ | CO | NH | CO | Me |
| 4.008. | $CH_2$ | 0 | | CO | NH | CO | Me |
| 4.009. | $CH_2$ | 1 | $CH_2$ | CO | NH | CO | Me |
| 4.010. | $CH_2$ | 0 | | $CH_2$ | NH | CO | Me |

TABLE 4-continued

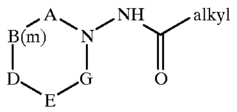

| Comp. | A | m | B | D | E | G | alkyl |
|---|---|---|---|---|---|---|---|
| 4.011. | $CH_2$ | 1 | $CH_2$ | $CH_2$ | NH | CO | Me |
| 4.012. | $CH_2$ | 1 | $CMe_2$ | $CH_2$ | NH | CO | Me |
| 4.013. | $CH_2$ | 1 | $CMe_2$ | $CH_2$ | NH | CO | Me |
| 4.014. | $CH_2$ | 1 | $C(OMe)_2$ | $CH_2$ | NH | CO | Me |
| 4.015. | $CH_2$ | 1 | $C(OEt)_2$ | $CH_2$ | NH | CO | Me |
| 4.016. | $CH_2$ | 1 | $C(CH_2OH)_2$ | $CH_2$ | NH | CO | Me |
| 4.017. | $CH_2$ | 1 | CO | $CH_2$ | NH | CO | Me |
| 4.018. | $CH_2$ | 1 | CHOH | $CH_2$ | NH | CO | Me |
| 4.019. | $CH_2$ | 1 | O | $CH_2$ | NH | CO | Me |
| 4.020. | $CH_2$ | 1 | NMe | $CH_2$ | NH | CO | Me |
| 4.021. | $CH_2$ | 0 | | $CH_2$ | NH | CO | Me |
| 4.022. | $CH_2$ | 1 | $CH_2$ | $CH_2$ | NH | CO | Me |
| 4.023. | $CH_2$ | 1 | $CH_2$ | $CH_2$ | NH | CO | Me |
| 4.024. | $CH_2$ | 1 | CH= | CH= | NH | CO | Me |
| 4.025. | $CH_2$ | 0 | | CHMe | NH | CO | Me |
| 4.026. | $CH_2$ | 0 | | CHMe | NH | CO | Me |
| 4.027. | $CH_2$ | 1 | $CH_2$ | CHMe | NH | CO | Me |
| 4.028. | $CH_2$ | 1 | $CH_2$ | CHMe | NH | CO | Me |
| 4.029. | $CH_2$ | 0 | | $CHCH_2OMe$ | NH | CO | Me |
| 4.030. | $CH_2$ | 1 | $CH_2$ | $CHCH_2OMe$ | NH | CO | Me |
| 4.031. | $CH_2$ | 0 | | CHtBu | NH | CO | Me |
| 4.032. | $CH_2$ | 1 | $CH_2$ | CHtBu | NH | CO | Me |
| 4.033. | $CH_2$ | 0 | | CHiPr | NH | CO | Me |
| 4.034. | $CH_2$ | 1 | $CH_2$ | CHiPr | NH | CO | Me |
| 4.035. | $CH_2$ | 0 | | CHcPr | NH | CO | Me |
| 4.036. | $CH_2$ | 1 | $CH_2$ | CHcPr | NH | CO | Me |
| 4.037. | $CH_2$ | 0 | | CHEt | NH | CO | Me |
| 4.038. | $CH_2$ | 0 | | CHEt | NH | CO | Me |
| 4.039. | $CH_2$ | 1 | $CH_2$ | CHEt | NH | CO | Me |
| 4.040. | $CH_2$ | 1 | $CH_2$ | CHEt | NH | CO | Me |
| 4.041. | $CH_2$ | 1 | CMe= | C= | NH | CO | Me |
| 4.042. | $CH_2$ | 1 | CEt= | C= | NH | CO | Me |
| 4.043. | CH= | 0 | | N= | NH | CO | Me |
| 4.044. | CH= | 1 | $CH_2$ | N= | NH | CO | Me |
| 4.045. | CH= | 1 | CMe= | $CH_2$ | NH | CO | Me |
| 4.046. | CH= | 1 | CEt= | $CH_2$ | NH | CO | Me |
| 4.047. | CH= | 0 | | CMe= | NMe | CO | Me |
| 4.048. | CH= | 1 | CH= | CHMe | NH | CO | Me |
| 4.049. | CMe= | 0 | | CH= | NH | CO | Me |
| 4.050. | CHMe | 1 | CH= | CH= | NH | CO | Me |
| 4.051. | CHMe | 0 | | $CH_2$ | NH | CO | Me |
| 4.052. | CHMe | 1 | $CH_2$ | $CH_2$ | NH | CO | Me |
| 4.053. | CHMe | 0 | | CHMe | NH | CO | Me |
| 4.054. | CHMe | 1 | $CH_2$ | CHMe | NH | CO | Me |
| 4.055. | CHMe | 0 | | CHEt | NH | CO | Me |
| 4.056. | CHMe | 1 | $CH_2$ | CHEt | NH | CO | Me |
| 4.057. | $CHCH_2OMe$ | 0 | | $CH_2$ | NH | CO | Me |
| 4.058. | $CHCH_2OMe$ | 1 | $CH_2$ | $CH_2$ | NH | CO | Me |
| 4.059. | CHtBu | 0 | | $CH_2$ | NH | CO | Me |
| 4.060. | CHtBu | 1 | $CH_2$ | $CH_2$ | NH | CO | Me |
| 4.061. | CHiPr | 0 | | $CH_2$ | NH | CO | Me |
| 4.062. | CHiPr | 1 | $CH_2$ | $CH_2$ | NH | CO | Me |
| 4.063. | CHiPr | 0 | | $CH_2$ | NH | CO | Me |
| 4.064. | CHiPr | 1 | $CH_2$ | $CH_2$ | NH | CO | Me |
| 4.065. | CHiPr | 0 | | CHMe | NH | CO | Me |
| 4.066. | CHiPr | 1 | $CH_2$ | CHMe | NH | CO | Me |
| 4.067. | CHiPr | 0 | | CHEt | NH | CO | Me |
| 4.068. | CHiPr | 1 | $CH_2$ | CHEt | NH | CO | Me |
| 4.069. | CHcPr | 0 | | $CH_2$ | NH | CO | Me |
| 4.070. | CHcPr | 1 | $CH_2$ | $CH_2$ | NH | CO | Me |
| 4.071. | CHEt | 0 | | $CH_2$ | NH | CO | Me |
| 4.072. | CHEt | 1 | $CH_2$ | $CH_2$ | NH | CO | Me |
| 4.073. | CHEt | 0 | | $CH_2$ | NH | CO | Me |
| 4.074. | CHEt | 1 | $CH_2$ | $CH_2$ | NH | CO | Me |
| 4.075. | CHEt | 0 | | CHMe | NH | CO | Me |
| 4.076. | CHEt | 1 | $CH_2$ | CHMe | NH | CO | Me |
| 4.077. | CHEt | 0 | | CHEt | NH | CO | Me |
| 4.078. | CHEt | 1 | $CH_2$ | CHEt | NH | CO | Me |
| 4.079. | $CMe_2$ | 0 | | CO | NH | CO | Me |
| 4.080. | $CMe_2$ | 1 | $CH_2$ | CO | NH | CO | Me |

TABLE 4-continued

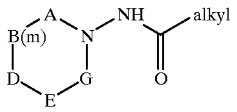

| Comp. | A | m | B | D | E | G | alkyl |
|---|---|---|---|---|---|---|---|
| 4.081. | $CMe_2$ | 0 | | $CH_2$ | NH | CO | Me |
| 4.082. | $CMe_2$ | 1 | $CH_2$ | $CH_2$ | NH | CO | Me |
| 4.083. | CMe= | 0 | | N= | NH | CO | Me |
| 4.084. | CHMe | 1 | $CH_2$ | NH | NH | CO | Me |
| 4.085. | CMe= | 0 | | CH= | NH | CO | Me |
| 4.086. | CHMe | 1 | $CH_2$ | $CH_2$ | NH | CO | Me |
| 4.101. | CO | 1 | $CMe_2$ | CO | NH | CO | $CF_3$ |
| 4.102. | CO | 1 | $CMe_2$ | $CH_2$ | NH | CO | $CF_3$ |
| 4.103. | CO | 0 | | $CH_2$ | NH | CO | $CF_3$ |
| 4.104. | CO | 1 | $CH_2$ | $CH_2$ | NH | CO | $CF_3$ |
| 4.105. | CO | 0 | | $CMe_2$ | NH | CO | $CF_3$ |
| 4.106. | CO | 1 | $CH_2$ | $CMe_2$ | NH | CO | $CF_3$ |
| 4.107. | $CH_2$ | 1 | $CMe_2$ | CO | NH | CO | $CF_3$ |
| 4.108. | $CH_2$ | 0 | | CO | NH | CO | $CF_3$ |
| 4.109. | $CH_2$ | 1 | $CH_2$ | CO | NH | CO | $CF_3$ |
| 4.110. | $CH_2$ | 0 | | $CH_2$ | NH | CO | $CF_3$ |
| 4.111. | $CH_2$ | 1 | $CH_2$ | $CH_2$ | NH | CO | $CF_3$ |
| 4.112. | $CH_2$ | 1 | $CMe_2$ | $CH_2$ | NH | CO | $CF_3$ |
| 4.113. | $CH_2$ | 1 | $CMe_2$ | $CH_2$ | NH | CO | $CF_3$ |
| 4.114. | $CH_2$ | 1 | $C(OMe)_2$ | $CH_2$ | NH | CO | $CF_3$ |
| 4.115. | $CH_2$ | 1 | $C(OEt)_2$ | $CH_2$ | NH | CO | $CF_3$ |
| 4.116. | $CH_2$ | 1 | $C(CH_2OH)_2$ | $CH_2$ | NH | CO | $CF_3$ |
| 4.117. | $CH_2$ | 1 | CO | $CH_2$ | NH | CO | $CF_3$ |
| 4.118. | $CH_2$ | 1 | CHOH | $CH_2$ | NH | CO | $CF_3$ |
| 4.119. | $CH_2$ | 1 | O | $CH_2$ | NH | CO | $CF_3$ |
| 4.120. | $CH_2$ | 1 | NMe | $CH_2$ | NH | CO | $CF_3$ |
| 4.121. | $CH_2$ | 0 | | $CH_2$ | NH | CO | $CF_3$ |
| 4.122. | $CH_2$ | 1 | $CH_2$ | $CH_2$ | NH | CO | $CF_3$ |
| 4.123. | $CH_2$ | 1 | $CH_2$ | $CH_2$ | NH | CO | $CF_3$ |
| 4.124. | $CH_2$ | 1 | CH= | CH= | NH | CO | $CF_3$ |
| 4.125. | $CH_2$ | 0 | | CHMe | NH | CO | $CF_3$ |
| 4.126. | $CH_2$ | 0 | | CHMe | NH | CO | $CF_3$ |
| 4.127. | $CH_2$ | 1 | $CH_2$ | CHMe | NH | CO | $CF_3$ |
| 4.128. | $CH_2$ | 1 | $CH_2$ | CHMe | NH | CO | $CF_3$ |
| 4.129. | $CH_2$ | 0 | | $CHCH_2OMe$ | NH | CO | $CF_3$ |
| 4.130. | $CH_2$ | 1 | $CH_2$ | $CHCH_2OMe$ | NH | CO | $CF_3$ |
| 4.131. | $CH_2$ | 0 | | CHtBu | NH | CO | $CF_3$ |
| 4.132. | $CH_2$ | 1 | $CH_2$ | CHtBu | NH | CO | $CF_3$ |
| 4.133. | $CH_2$ | 0 | | CHiPr | NH | CO | $CF_3$ |
| 4.134. | $CH_2$ | 1 | $CH_2$ | CHiPr | NH | CO | $CF_3$ |
| 4.135. | $CH_2$ | 0 | | CHcPr | NH | CO | $CF_3$ |
| 4.136. | $CH_2$ | 1 | $CH_2$ | CHcPr | NH | CO | $CF_3$ |
| 4.137. | $CH_2$ | 0 | | CHEt | NH | CO | $CF_3$ |
| 4.138. | $CH_2$ | 0 | | CHEt | NH | CO | $CF_3$ |
| 4.139. | $CH_2$ | 1 | $CH_2$ | CHEt | NH | CO | $CF_3$ |
| 4.140. | $CH_2$ | 1 | $CH_2$ | CHEt | NH | CO | $CF_3$ |
| 4.141. | $CH_2$ | 1 | CMe= | CH= | NH | CO | $CF_3$ |
| 4.142. | $CH_2$ | 1 | CEt= | CH= | NH | CO | $CF_3$ |
| 4.143. | CH= | 0 | | N= | NH | CO | $CF_3$ |
| 4.144. | CH= | 1 | $CH_2$ | N= | NH | CO | $CF_3$ |
| 4.145. | CH= | 1 | CMe= | $CH_2$ | NH | CO | $CF_3$ |
| 4.146. | CH= | 1 | CEt= | $CH_2$ | NH | CO | $CF_3$ |
| 4.147. | CH= | 0 | | CMe= | NH | CO | $CF_3$ |
| 4.148. | $CH_2$ | 1 | $CH_2$ | CHMe | NH | CO | $CF_3$ |
| 4.149. | CHMe | 0 | | $CH_2$ | NH | CO | $CF_3$ |
| 4.150. | CHMe | 1 | CH= | CH= | NH | CO | $CF_3$ |
| 4.151. | CHMe | 0 | | $CH_2$ | NH | CO | $CF_3$ |
| 4.152. | CHMe | 1 | $CH_2$ | $CH_2$ | NH | CO | $CF_3$ |
| 4.153. | CHMe | 0 | | CHMe | NH | CO | $CF_3$ |
| 4.154. | CHMe | 1 | $CH_2$ | CHMe | NH | CO | $CF_3$ |
| 4.155. | CHMe | 0 | | CHEt | NH | CO | $CF_3$ |
| 4.156. | CHMe | 1 | $CH_2$ | CHEt | NH | CO | $CF_3$ |
| 4.157. | $CHCH_2OMe$ | 0 | | $CH_2$ | NH | CO | $CF_3$ |
| 4.158. | $CHCH_2OMe$ | 1 | $CH_2$ | $CH_2$ | NH | CO | $CF_3$ |
| 4.159. | CHtBu | 0 | | $CH_2$ | NH | CO | $CF_3$ |
| 4.160. | CHtBu | 1 | $CH_2$ | $CH_2$ | NH | CO | $CF_3$ |
| 4.161. | CHiPr | 0 | | $CH_2$ | NH | CO | $CF_3$ |
| 4.162. | CHiPr | 1 | $CH_2$ | $CH_2$ | NH | CO | $CF_3$ |
| 4.163. | CHiPr | 0 | | $CH_2$ | NH | CO | $CF_3$ |
| 4.164. | CHiPr | 1 | $CH_2$ | $CH_2$ | NH | CO | $CF_3$ |

TABLE 4-continued

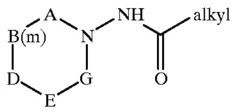

| Comp. | A | m | B | D | E | G | alkyl |
|---|---|---|---|---|---|---|---|
| 4.165. | CHiPr | 0 | | CHMe | NH | CO | $CF_3$ |
| 4.166. | CHiPr | 1 | $CH_2$ | CHMe | NH | CO | $CF_3$ |
| 4.167. | CHiPr | 0 | | CHEt | NH | CO | $CF_3$ |
| 4.168. | CHiPr | 1 | $CH_2$ | CHEt | NH | CO | $CF_3$ |
| 4.169. | CHcPr | 0 | | $CH_2$ | NH | CO | $CF_3$ |
| 4.170. | CHcPr | 1 | $CH_2$ | $CH_2$ | NH | CO | $CF_3$ |
| 4.171. | CHEt | 0 | | $CH_2$ | NH | CO | $CF_3$ |
| 4.172. | CHEt | 1 | $CH_2$ | $CH_2$ | NH | CO | $CF_3$ |
| 4.173. | CHEt | 0 | | $CH_2$ | NH | CO | $CF_3$ |
| 4.174. | CHEt | 1 | $CH_2$ | $CH_2$ | NH | CO | $CF_3$ |
| 4.175. | CHEt | 0 | | CHMe | NH | CO | $CF_3$ |
| 4.176. | CHEt | 1 | $CH_2$ | CHMe | NH | CO | $CF_3$ |
| 4.177. | CHEt | 0 | | CHEt | NH | CO | $CF_3$ |
| 4.178. | CHEt | 1 | $CH_2$ | CHEt | NH | CO | $CF_3$ |
| 4.179. | $CMe_2$ | 0 | | CO | NH | CO | $CF_3$ |
| 4.180. | $CMe_2$ | 1 | $CH_2$ | CO | NH | CO | $CF_3$ |
| 4.181. | $CMe_2$ | 0 | | $CH_2$ | NH | CO | $CF_3$ |
| 4.182. | $CMe_2$ | 1 | $CH_2$ | $CH_2$ | NH | CO | $CF_3$ |
| 4.183. | CMe= | 0 | | N= | NH | CO | $CF_3$ |
| 4.184. | CHMe | 1 | $CH_2$ | NH | NH | CO | $CF_3$ |
| 4.185. | CMe= | 0 | | CH= | NH | CO | $CF_3$ |
| 4.186. | CHMe | 1 | $CH_2$ | $CH_2$ | NH | CO | $CF_3$ |
| 4.201. | CO | 1 | $CMe_2$ | CO | NH | CO | Et |
| 4.202. | CO | 1 | $CMe_2$ | $CH_2$ | NH | CO | Et |
| 4.203. | CO | 0 | | $CH_2$ | NH | CO | Et |
| 4.204. | CO | 1 | $CH_2$ | $CH_2$ | NH | CO | Et |
| 4.205. | CO | 0 | | $CMe_2$ | NH | CO | Et |
| 4.206. | CO | 1 | $CH_2$ | $CMe_2$ | NH | CO | Et |
| 4.207. | $CH_2$ | 1 | $CMe_2$ | CO | NH | CO | Et |
| 4.208. | $CH_2$ | 0 | | CO | NH | CO | Et |
| 4.209. | $CH_2$ | 1 | $CH_2$ | CO | NH | CO | Et |
| 4.210. | $CH_2$ | 0 | | $CH_2$ | NH | CO | Et |
| 4.211. | $CH_2$ | 1 | $CH_2$ | $CH_2$ | NH | CO | Et |
| 4.212. | $CH_2$ | 1 | $CMe_2$ | $CH_2$ | NH | CO | Et |
| 4.213. | $CH_2$ | 1 | $CMe_2$ | $CH_2$ | NH | CO | Et |
| 4.214. | $CH_2$ | 1 | $C(OMe)_2$ | $CH_2$ | NH | CO | Et |
| 4.215. | $CH_2$ | 1 | $C(OEt)_2$ | $CH_2$ | NH | CO | Et |
| 4.216. | $CH_2$ | 1 | $C(CH_2OH)_2$ | $CH_2$ | NH | CO | Et |
| 4.217. | $CH_2$ | 1 | CO | $CH_2$ | NH | CO | Et |
| 4.218. | $CH_2$ | 1 | CHOH | $CH_2$ | NH | CO | Et |
| 4.219. | $CH_2$ | 1 | O | $CH_2$ | NH | CO | Et |
| 4.220. | $CH_2$ | 1 | NMe | $CH_2$ | NH | CO | Et |
| 4.221. | $CH_2$ | 0 | | $CH_2$ | NH | CO | Et |
| 4.222. | $CH_2$ | 1 | $CH_2$ | $CH_2$ | NH | CO | Et |
| 4.223. | $CH_2$ | 1 | $CH_2$ | $CH_2$ | NH | CO | Et |
| 4.224. | $CH_2$ | 1 | CH= | CH= | NH | CO | Et |
| 4.225. | $CH_2$ | 0 | | CHMe | NH | CO | Et |
| 4.226. | $CH_2$ | 0 | | CHMe | NH | CO | Et |
| 4.227. | $CH_2$ | 1 | $CH_2$ | CHMe | NH | CO | Et |
| 4.228. | $CH_2$ | 1 | $CH_2$ | CHMe | NH | CO | Et |
| 4.229. | $CH_2$ | 0 | | $CHCH_2OMe$ | NH | CO | Et |
| 4.230. | $CH_2$ | 1 | $CH_2$ | $CHCH_2OMe$ | NH | CO | Et |
| 4.231. | $CH_2$ | 0 | | CHtBu | NH | CO | Et |
| 4.232. | $CH_2$ | 1 | $CH_2$ | CHtBu | NH | CO | Et |
| 4.233. | $CH_2$ | 0 | | CHiPr | NH | CO | Et |
| 4.234. | $CH_2$ | 1 | $CH_2$ | CHiPr | NH | CO | Et |
| 4.235. | $CH_2$ | 0 | | CHcPr | NH | CO | Et |
| 4.236. | $CH_2$ | 1 | $CH_2$ | CHcPr | NH | CO | Et |
| 4.237. | $CH_2$ | 0 | | CHEt | NH | CO | Et |
| 4.238. | $CH_2$ | 0 | | CHEt | NH | CO | Et |
| 4.239. | $CH_2$ | 1 | $CH_2$ | CHEt | NH | CO | Et |
| 4.240. | $CH_2$ | 1 | $CH_2$ | CHEt | NH | CO | Et |
| 4.241. | $CH_2$ | 1 | CMe= | CH= | NH | CO | Et |
| 4.242. | $CH_2$ | 1 | CEt= | CH= | NH | CO | Et |
| 4.243. | CH= | 0 | | N= | NH | CO | Et |
| 4.244. | CH= | 1 | $CH_2$ | N= | NH | CO | Et |
| 4.245. | CH= | 1 | CMe= | $CH_2$ | NH | CO | Et |
| 4.246. | CH= | 1 | CEt= | $CH_2$ | NH | CO | Et |
| 4.247. | CH= | 0 | | CMe= | NH | CO | Et |
| 4.248. | $CH_2$ | 1 | $CH_2$ | CHMe | NH | CO | Et |

TABLE 4-continued

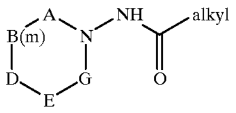

| Comp. | A | m | B | D | E | G | alkyl |
|---|---|---|---|---|---|---|---|
| 4.249. | CHMe | 0 | | $CH_2$ | NH | CO | Et |
| 4.250. | CHMe | 1 | CH= | CH= | NH | CO | Et |
| 4.248. | CH= | 1 | $CH_2$ | CMe= | NH | CO | Et |
| 4.249. | CHMe | 0 | | CH= | NH | CO | Et |
| 4.250. | CHMe | 1 | $CH_2$ | CH= | NH | CO | Et |
| 4.251. | CHMe | 0 | | $CH_2$ | NH | CO | Et |
| 4.252. | CHMe | 1 | $CH_2$ | $CH_2$ | NH | CO | Et |
| 4.253. | CHMe | 0 | | CHMe | NH | CO | Et |
| 4.254. | CHMe | 1 | $CH_2$ | CHMe | NH | CO | Et |
| 4.255. | CHMe | 0 | | CHEt | NH | CO | Et |
| 4.256. | CHMe | 1 | $CH_2$ | CHEt | NH | CO | Et |
| 4.257. | $CHCH_2OMe$ | 0 | | $CH_2$ | NH | CO | Et |
| 4.258. | $CHCH_2OMe$ | 1 | $CH_2$ | $CH_2$ | NH | CO | Et |
| 4.259. | CHtBu | 0 | | $CH_2$ | NH | CO | Et |
| 4.260. | CHtBu | 1 | $CH_2$ | $CH_2$ | NH | CO | Et |
| 4.261. | CHiPr | 0 | | $CH_2$ | NH | CO | Et |
| 4.262. | CHiPr | 1 | $CH_2$ | $CH_2$ | NH | CO | Et |
| 4.263. | CHiPr | 0 | | $CH_2$ | NH | CO | Et |
| 4.264. | CHiPr | 1 | $CH_2$ | $CH_2$ | NH | CO | Et |
| 4.265. | CHiPr | 0 | | CHMe | NH | CO | Et |
| 4.266. | CHiPr | 1 | $CH_2$ | CHMe | NH | CO | Et |
| 4.267. | CHiPr | 0 | | CHEt | NH | CO | Et |
| 4.268. | CHiPr | 1 | $CH_2$ | CHEt | NH | CO | Et |
| 4.269. | CHcPr | 0 | | $CH_2$ | NH | CO | Et |
| 4.270. | CHcPr | 1 | $CH_2$ | $CH_2$ | NH | CO | Et |
| 4.271. | CHEt | 0 | | $CH_2$ | NH | CO | Et |
| 4.272. | CHEt | 1 | $CH_2$ | $CH_2$ | NH | CO | Et |
| 4.273. | CHEt | 0 | | $CH_2$ | NH | CO | Et |
| 4.274. | CHEt | 1 | $CH_2$ | $CH_2$ | NH | CO | Et |
| 4.275. | CHEt | 0 | | CHMe | NH | CO | Et |
| 4.276. | CHEt | 1 | $CH_2$ | CHMe | NH | CO | Et |
| 4.277. | CHEt | 0 | | CHEt | NH | CO | Et |
| 4.278. | CHEt | 1 | $CH_2$ | CHEt | NH | CO | Et |
| 4.279. | $CMe_2$ | 0 | | CO | NH | CO | Et |
| 4.280. | $CMe_2$ | 1 | $CH_2$ | CO | NH | CO | Et |
| 4.281. | $CMe_2$ | 0 | | $CH_2$ | NH | CO | Et |
| 4.282. | $CMe_2$ | 1 | $CH_2$ | $CH_2$ | NH | CO | Et |
| 4.283. | CMe= | 0 | | N= | NH | CO | Et |
| 4.284. | CHMe | 1 | $CH_2$ | NH | NH | CO | Et |
| 4.285. | CMe= | 0 | | CH= | NH | CO | Et |
| 4.286. | CHMe | 1 | $CH_2$ | $CH_2$ | NH | CO | Et |

TABLE 4a melting points of compounds from Table 4

| Comp. | m.p.(°) |
|---|---|
| 4.025 | 124–127 |
| 4.047 | 198–201 |

Example P21

1,3-Bis(pyridin-3-ylmethyleneamino)urea 32.2 g of pyridine-3-carbaldehyde are added in the course of approx. 10 minutes, at room temperature, to a suspension of 13.5 g of carbohydrazide in 200 ml of methanol, the temperature rising to more than 35°. The reaction mixture is further stirred for 1 hour and then cooled to 5°. The crystals that precipitate are filtered off with suction and dried in vacuo at 70°. 40 g of the title compound having a melting point of 202–204° are thus obtained.

Example P22

1,3-Bis(pyridin-3-ylmethyleneamino)-4-hydroxy-4-methylimidazolidin-2-one (Compound 5.100 in Table 5)

27.6 g of potassium carbonate and 13.9 g of chloroacetone are added to a solution of 26.8 g of 1,3-bis(pyridin-3-ylmethyleneamino)urea in 300 ml of dimethylformamide. When the slightly exothermic reaction has subsided, stirring is continued for about 1 hour. 500 ml of ether are added to the resulting suspension. The suspension is then filtered and the crystals are dried. 58 g of a crystal mixture are obtained. 200 ml of methylene chloride and 50 ml of water are added to the crystal mixture, which is then stirred for 30 minutes. The remaining crystals are filtered off with suction, washed with methylene chloride and water (1:1) and dried in vacuo at 70°. 25.3 g of the title compound having a melting point of 175–182° are thus obtained.

Example P23

1,3-Bis(pyridin-3-ylmethyleneamino)-4-methyl-1,3-dihydroimidazol-2-one (Compound 5.096 in Table 5) and 1,3-bis(pyridin-3-ylmethyleneamino)-4-methoxy-4-methylimidazolidin-2-one (Compound 5.110 in Table 5)

Concentrated sulfuric acid is added dropwise to a suspension of 9.8 g of 1,3-bis(pyridin-3-ylmethyleneamino)4- hydroxy4-methylimidazolidin-2-one in 20 ml of methanol. When the reaction mixture, the temperature of which rises quickly, becomes difficult to stir, a further 20 ml of methanol are added and then further sulfuric acid is added dropwise. When the reaction mixture, the temperature of which continues to rise quickly, again becomes difficult to stir, a further 20 ml of methanol are added and then further sulfuric acid is added dropwise (approx. 4 ml in total). The reaction mixture is cooled to 20°, filtered with suction, washed with methanol and dried. 8.8 g of crystals of the disulfate of 1,3-bis(pyridin-3-ylmethyleneamino)-4-methyl-1,3-dihydroimidazol-2-one having a melting point of 202–205° are obtained. The mother liquor is chromatographed on silica gel with ether/tetrahydrofuran, there being obtained inter alia 0.55 g of crystals of 1,3-bis(pyridin-3-ylmethyleneamino)-4-methoxy-4-methylimidazolidin-2-one having a melting point of 202–207°.

7.7 g of the disulfate of 1,3-bis(pyridin-3-ylmethyleneamino)-4-methyl-1,3-dihydroimidazol-2-one are dissolved in 200 ml of water. The pH is brought to 7 with 2N sodium hydroxide solution, whereupon crystals precipitate. The crystals are extracted four times with 100 ml of methylene chloride each time. The organic phase is dried with magnesium sulfate and concentrated by evaporation. The residue is stirred with ether, filtered with suction and dried. 4.1 g of crystals of 1,3-bis(pyridin-3-ylmethyleneamino)-4-methyl-1,3-dihydroimidazol-2-one having a melting point of 172–174° are thus obtained.

Example P24

1,3-Bis(pyridin-3-ylmethyleneamino)-4-methyl-1,3-dihydroimidazol-2-one (Compound 5.096 in Table 5)

11.2 g of acetic anhydride are added to a suspension of 32.4 g of 1,3-bis(pyridin-3-yl-methyleneamino)-4-hydroxy-4-methylimidazolidin-2-one in 75 ml of acetic acid. The reaction mixture is then heated to 50°. After 3 hours the reaction mixture is cooled to 20°, then poured onto 800 ml of ice-water and neutralised with 30% sodium hydroxide solution. The aqueous phase is then extracted three times with 200 ml of methylene chloride each time. The organic phase is dried with magnesium sulfate, filtered and concentrated by evaporation. The residue is stirred with ether. The crystals are filtered off with suction and dried. 28.2 g of the title compound having a melting point of 176–178° are thus obtained.

Example P25

The other compounds listed in Tables 5, 5a and 6 can also be prepared in a manner analogous to that described in Examples P21 to P24.

TABLE 5

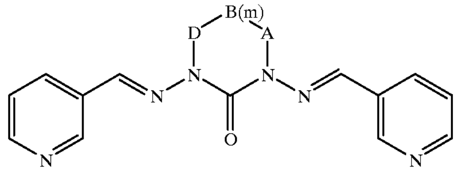

| No. | A | m | B | D | G |
|---|---|---|---|---|---|
| 5.001 | CO | 1 | $NCH_2cHex$ | CO | CO |
| 5.002 | CO | 1 | $CH_2$ | CO | CO |
| 5.003 | CO | 1 | $CMe_2$ | CO | CO |
| 5.004 | CO | 0 | | CO | CO |
| 5.005 | CO | 1 | $CH_2$ | $CH_2$ | CO |

TABLE 5-continued

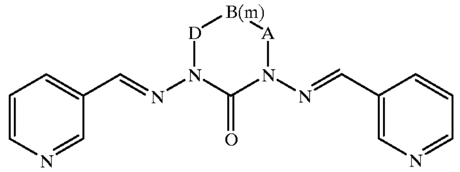

| No. | A | m | B | D | G |
|---|---|---|---|---|---|
| 5.006 | CO | 1 | $CMe_2$ | $CH_2$ | CO |
| 5.007 | CO | 0 | | $CH_2$ | CO |
| 5.008 | CO | 0 | | $CHCH_2COOMe$ | CS |
| 5.009 | CO | 0 | | $CHC_2H_4COOMe$ | CS |
| 5.010 | CO | 1 | $CH_2$ | $CMe_2$ | CO |
| 5.011 | CO | 0 | | $CMe_2$ | CO |
| 5.012 | CO | 1 | CH= | CMe= | CO |
| 5.013 | CO | 0 | | $CMeCH_2CMe_2$ | CO |
| 5.014 | CO | 0 | | $CMeCH{=}CMe_2$ | CO |
| 5.015 | CO | 1 | CH= | $CCF_3{=}$ | CNH |
| 5.016 | $CH_2$ | 0 | | CO | CO |
| 5.017 | $CH_2$ | 0 | | CO | CS |
| 5.018 | $CH_2$ | 1 | $CMe_2$ | CO | CO |
| 5.019 | $CH_2$ | 0 | | CO | CO |
| 5.020 | $CH_2$ | 1 | $CH_2$ | CO | CO |
| 5.021 | $CH_2$ | 0 | | $CH_2$ | CO |
| 5.022 | $CH_2$ | 0 | | $CH_2$ | CS |
| 5.023 | $CH_2$ | 0 | | $CH_2$ | CO |
| 5.024 | $CH_2$ | 0 | | $CH_2$ | CO |
| 5.025 | $CH_2$ | 1 | $CH_2$ | $CH_2$ | CO |
| 5.026 | $CH_2$ | 1 | $CMe_2$ | $CH_2$ | CO |
| 5.027 | $CH_2$ | 1 | $CMe_2$ | $CH_2$ | CO |
| 5.028 | $CH_2$ | 1 | $C(OMe)_2$ | $CH_2$ | CO |
| 5.029 | $CH_2$ | 1 | $C(OEt)_2$ | $CH_2$ | CO |
| 5.030 | $CH_2$ | 1 | $C(CH_2OH)_2$ | $CH_2$ | CO |
| 5.031 | $CH_2$ | 1 | CO | $CH_2$ | CO |
| 5.032 | $CH_2$ | 1 | CHOH | $CH_2$ | CO |
| 5.033 | $CH_2$ | 1 | O | $CH_2$ | CO |
| 5.034 | $CH_2$ | 1 | NMe | $CH_2$ | CO |
| 5.035 | $CH_2$ | 0 | | $CH_2$ | CO |
| 5.036 | $CH_2$ | 1 | $CH_2$ | $CH_2$ | CO |
| 5.037 | $CH_2$ | 1 | $CH_2$ | $CH_2$ | CO |
| 5.038 | $CH_2$ | 1 | CH= | CH= | CO |
| 5.039 | $CH_2$ | 0 | | CHMe | CO |
| 5.040 | $CH_2$ | 0 | | CHMe | CO |
| 5.041 | $CH_2$ | 1 | $CH_2$ | CHMe | CO |
| 5.042 | $CH_2$ | 1 | $CH_2$ | CHMe | CO |
| 5.043 | $CH_2$ | 0 | | $CHCH_2OMe$ | CO |
| 5.044 | $CH_2$ | 1 | $CH_2$ | $CHCH_2OMe$ | CO |
| 5.045 | $CH_2$ | 0 | | CHtBu | CO |
| 5.046 | $CH_2$ | 1 | $CH_2$ | CHtBu | CO |
| 5.047 | $CH_2$ | 0 | | CHiPr | CO |
| 5.048 | $CH_2$ | 1 | $CH_2$ | CHiPr | CO |
| 5.049 | $CH_2$ | 0 | | CHcPr | CO |
| 5.050 | $CH_2$ | 1 | $CH_2$ | CHcPr | CO |
| 5.051 | $CH_2$ | 0 | | CHEt | CO |
| 5.052 | $CH_2$ | 0 | | CHEt | CO |
| 5.053 | $CH_2$ | 1 | $CH_2$ | CHEt | CO |
| 5.054 | $CH_2$ | 1 | $CH_2$ | CHEt | CO |
| 5.055 | $CH_2$ | 1 | CMe= | CH= | CO |
| 5.056 | $CH_2$ | 1 | CEt= | CH= | CO |
| 5.057 | CH= | 1 | CMe= | $CH_2$ | CO |
| 5.058 | CH= | 1 | CEt= | $CH_2$ | CO |
| 5.059 | CH= | 0 | | CMe= | CO |
| 5.060 | CH= | 1 | $CH_2$ | CMe= | CO |
| 5.061 | CH= | 0 | | CtBu= | CO |
| 5.062 | CHMe | 0 | | CHnPr | CO |
| 5.063 | CHMe | 1 | $CH_2$ | CHnPr | CO |
| 5.064 | CHMe | 0 | | $CH_2$ | CO |
| 5.065 | CHMe | 1 | $CH_2$ | $CH_2$ | CO |
| 5.066 | CHMe | 0 | | CHMe | CO |
| 5.067 | CHMe | 1 | $CH_2$ | CHMe | CO |
| 5.068 | CHMe | 0 | | CHEt | CO |
| 5.069 | CHMe | 1 | $CH_2$ | CHEt | CO |
| 5.070 | $CHCH_2OMe$ | 0 | | $CH_2$ | CO |
| 5.071 | $CHCH_2OMe$ | 1 | $CH_2$ | $CH_2$ | CO |
| 5.072 | CHtBu | 0 | | $CH_2$ | CO |

TABLE 5-continued

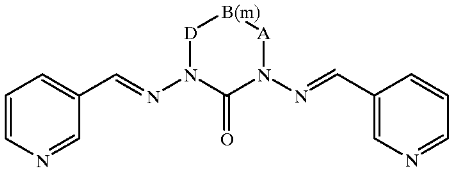

| No. | A | m | B | D | G |
|---|---|---|---|---|---|
| 5.073 | CHtBu | 1 | $CH_2$ | $CH_2$ | CO |
| 5.074 | CHiPr | 0 | | $CH_2$ | CO |
| 5.075 | CHiPr | 1 | $CH_2$ | $CH_2$ | CO |
| 5.076 | CHiPr | 0 | | $CH_2$ | CO |
| 5.077 | CHiPr | 1 | $CH_2$ | $CH_2$ | CO |
| 5.078 | CHiPr | 0 | | CHMe | CO |
| 5.079 | CHiPr | 1 | $CH_2$ | CHMe | CO |
| 5.080 | CHiPr | 0 | | CHEt | CO |
| 5.081 | CHiPr | 1 | $CH_2$ | CHEt | CO |
| 5.082 | CHcPr | 0 | | $CH_2$ | CO |
| 5.083 | CHcPr | 1 | $CH_2$ | $CH_2$ | CO |
| S.084 | CHEt | 0 | | $CH_2$ | CO |
| 5.085 | CHEt | 1 | $CH_2$ | $CH_2$ | CO |
| 5.086 | CHEt | 0 | | $CH_2$ | CO |
| 5.087 | CHEt | 1 | $CH_2$ | $CH_2$ | CO |
| 5.088 | CHEt | 0 | | CHMe | CO |
| 5.089 | CHEt | 1 | $CH_2$ | CHMe | CO |
| 5.090 | CHEt | 0 | | CHEt | CO |
| 5.091 | CHEt | 1 | $CH_2$ | CHEt | CO |
| 5.092 | $CMe_2$ | 0 | | CO | CO |
| 5.093 | $CMe_2$ | 1 | $CH_2$ | CO | CO |
| 5.094 | $CMe_2$ | 0 | | $CH_2$ | CO |
| 5.095 | $CMe_2$ | 1 | $CH_2$ | $CH_2$ | CO |
| 5.096 | CMe= | 0 | | CH= | CO |
| 5.097 | CMe= | 1 | $CH_2$ | CH= | CO |
| 5.098 | C(=NH) | 0 | | $CMe_2$ | CO |
| 5.099 | C(=NH) | 1 | CH= | CMe= | CO |
| 5.100 | C(OH)Me | 0 | | $CH_2$ | CO |
| 5.101 | C(OH)Et | 0 | | $CH_2$ | CO |
| 5.102 | C(OH)iPr | 0 | | $CH_2$ | CO |
| 5.103 | C(OH)cPr | 0 | | $CH_2$ | CO |

TABLE 5-continued

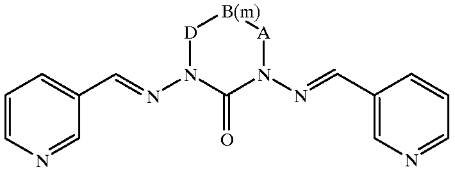

| No. | A | m | B | D | G |
|---|---|---|---|---|---|
| 5.104 | C(OH)Et | 1 | $CH_2$ | $CH_2$ | CO |
| 5.105 | C(OH)iPr | 1 | $CH_2$ | $CH_2$ | CO |
| 5.106 | C(OH)cPr | 1 | $CH_2$ | $CH_2$ | CO |
| 5.107 | C(OH)Me | 1 | CHMe | $CH_2$ | CO |
| 5.108 | CHOH | 1 | CHMe | $CH_2$ | CO |
| 5.109 | C(OEt)Me | 0 | | $CH_2$ | CO |
| 5.110 | C(OMe)Me | 0 | | $CH_2$ | CO |
| 5.111 | C(OH)Me | 0 | | CHMe | CO |
| 5.112 | $CH_2$ | 1 | CH(COOMe) | $CH_2$ | CO |
| 5.113 | C(Me)= | 0 | | C(Me)= | CO |

TABLE 5a melting points of compounds from Table 4

| Comp. | m.p.(°) |
|---|---|
| 5.023 | >240 |
| 5.025 | 218–219 |
| 5.036 | 218–219 |
| 5.059 | 176–178 |
| 5.096 | 176–178 |
| 5.100 | 175–182 |
| 5.110 | 202–207 |
| 5.111 | 152–154 |
| 5.112 | 208–209 |
| 5.113 | 203 |

TABLE 6

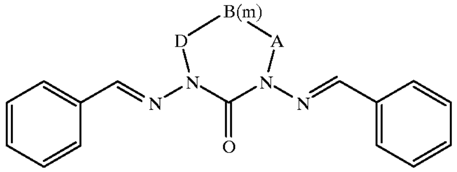

| No. | A | m | B | D | G | m.p. |
|---|---|---|---|---|---|---|
| 6.001. | CO | 1 | $N(CH_2cHex)$ | CO | CO | |
| 6.002. | CO | 1 | $CH_2$ | CO | CO | |
| 6.003. | CO | 1 | $CMe_2$ | CO | CO | |
| 6.004. | CO | 0 | | CO | CO | |
| 6.005. | CO | 1 | $CH_2$ | $CH_2$ | CO | |
| 6.006. | CO | 1 | $CMe_2$ | $CH_2$ | CO | |
| 6.007. | CO | 0 | | $CH_2$ | CO | |
| 6.008. | CO | 0 | | $CHCH_2COOMe$ | CS | |
| 6.009. | CO | 0 | | $CHC_2H_4COOMe$ | CS | |
| 6.010. | CO | 1 | $CH_2$ | $CMe_2$ | CO | |
| 6.011. | CO | 0 | | $CMe_2$ | CO | |
| 6.012. | CO | 1 | CH= | CMe= | CO | |
| 6.013. | CO | 0 | | $CMeCH_2CMe_2$ | CO | |
| 6.014. | CO | 0 | | $CMeCH{=}CMe_2$ | CO | |
| 6.015. | CO | 1 | CH= | $CCF_3$= | CNH | |
| 6.016. | $CH_2$ | 0 | | CO | CO | |
| 6.017. | $CH_2$ | 0 | | CO | CS | |
| 6.018. | $CH_2$ | 1 | $CMe_2$ | CO | CO | |
| 6.019. | $CH_2$ | 0 | | CO | CO | |

TABLE 6-continued

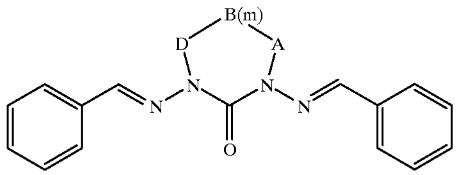

| No. | A | m | B | D | G | m.p. |
|---|---|---|---|---|---|---|
| 6.020. | $CH_2$ | 1 | $CH_2$ | CO | CO | |
| 6.021. | $CH_2$ | 0 | | $CH_2$ | CO | |
| 6.022. | $CH_2$ | 0 | | $CH_2$ | CS | |
| 6.023. | $CH_2$ | 0 | | $CH_2$ | CO | |
| 6.024. | $CH_2$ | 0 | | $CH_2$ | CO | |
| 6.025. | $CH_2$ | 1 | $CH_2$ | $CH_2$ | CO | |
| 6.026. | $CH_2$ | 1 | $CMe_2$ | $CH_2$ | CO | |
| 6.027. | $CH_2$ | 1 | $CMe_2$ | $CH_2$ | CO | |
| 6.028. | $CH_2$ | 1 | $C(OMe)_2$ | $CH_2$ | CO | |
| 6.029. | $CH_2$ | 1 | $C(OEt)_2$ | $CH_2$ | CO | |
| 6.030. | $CH_2$ | 1 | $C(CH_2OH)_2$ | $CH_2$ | CO | |
| 6.031. | $CH_2$ | 1 | CO | $CH_2$ | CO | |
| 6.032. | $CH_2$ | 1 | CHOH | $CH_2$ | CO | |
| 6.033. | $CH_2$ | 1 | O | $CH_2$ | CO | |
| 6.034. | $CH_2$ | 1 | NMe | $CH_2$ | CO | |
| 6.035. | $CH_2$ | 0 | | $CH_2$ | CO | |
| 6.036. | $CH_2$ | 1 | $CH_2$ | $CH_2$ | CO | |
| 6.037. | $CH_2$ | 1 | $CH_2$ | $CH_2$ | CO | |
| 6.038. | $CH_2$ | 1 | CH═ | CH═ | CO | |
| 6.039. | $CH_2$ | 0 | | CHMe | CO | |
| 6.040. | $CH_2$ | 0 | | CHMe | CO | |
| 6.041. | $CH_2$ | 1 | $CH_2$ | CHMe | CO | |
| 6.042. | $CH_2$ | 1 | $CH_2$ | CHMe | CO | |
| 6.043. | $CH_2$ | 0 | | $CHCH_2OMe$ | CO | |
| 6.044. | $CH_2$ | 1 | $CH_2$ | $CHCH_2OMe$ | CO | |
| 6.045. | $CH_2$ | 0 | | CHtBu | CO | |
| 6.046. | $CH_2$ | 1 | $CH_2$ | CHtBu | CO | |
| 6.047. | $CH_2$ | 0 | | CHiPr | CO | |
| 6.048. | $CH_2$ | 1 | $CH_2$ | CHiPr | CO | |
| 6.049. | $CH_2$ | 0 | | CHcPr | CO | |
| 6.050. | $CH_2$ | 1 | $CH_2$ | CHcPr | CO | |
| 6.051. | $CH_2$ | 0 | | CHEt | CO | |
| 6.052. | $CH_2$ | 0 | | CHEt | CO | |
| 6.053. | $CH_2$ | 1 | $CH_2$ | CHEt | CO | |
| 6.054. | $CH_2$ | 1 | $CH_2$ | CHEt | CO | |
| 6.055. | $CH_2$ | 1 | CMe═ | CH═ | CO | |
| 6.056. | $CH_2$ | 1 | CEt═ | CH═ | CO | |
| 6.057. | CH═ | 1 | CMe═ | $CH_2$ | CO | |
| 6.058. | CH═ | 1 | CEt═ | $CH_2$ | CO | |
| 6.059. | CH═ | 0 | | CMe═ | CO | |
| 6.060. | CH═ | 1 | $CH_2$ | CMe═ | CO | |
| 6.061. | CH═ | 0 | | CtBu═ | CO | |
| 6.061. | CH═ | 0 | | CHtBu | CO | |
| 6.062. | CHMe | 0 | | CHnPr | CO | |
| 6.063. | CHMe | 1 | $CH_2$ | CHnPr | CO | |
| 6.064. | CHMe | 0 | | $CH_2$ | CO | |
| 6.065. | CHMe | 1 | $CH_2$ | $CH_2$ | CO | |
| 6.066. | CHMe | 0 | | CHMe | CO | |
| 6.067. | CHMe | 1 | $CH_2$ | CHMe | CO | |
| 6.068. | CHMe | 0 | | CHEt | CO | |
| 6.069. | CHMe | 1 | $CH_2$ | CHEt | CO | |
| 6.070. | $CHCH_2OMe$ | 0 | | $CH_2$ | CO | |
| 6.071. | $CHCH_2OMe$ | 1 | $CH_2$ | $CH_2$ | CO | |
| 6.072. | CHtBu | 0 | | $CH_2$ | CO | |
| 6.073. | CHtBu | 1 | $CH_2$ | $CH_2$ | CO | |
| 6.074. | CHiPr | 0 | | $CH_2$ | CO | |
| 6.075. | CHiPr | 1 | $CH_2$ | $CH_2$ | CO | |
| 6.076. | CHiPr | 0 | | $CH_2$ | CO | |
| 6.077. | CHiPr | 1 | $CH_2$ | $CH_2$ | CO | |
| 6.078. | CHiPr | 0 | | CHMe | CO | |
| 6.079. | CHiPr | 1 | $CH_2$ | CHMe | CO | |
| 6.080. | CHiPr | 0 | | CHEt | CO | |
| 6.081. | CHiPr | 1 | $CH_2$ | CHEt | CO | |
| 6.082. | CHcPr | 0 | | $CH_2$ | CO | |
| 6.083. | CHcPr | 1 | $CH_2$ | $CH_2$ | CO | |
| 6.084. | CHEt | 0 | | $CH_2$ | CO | |
| 6.085. | CHEt | 1 | $CH_2$ | $CH_2$ | CO | |

TABLE 6-continued

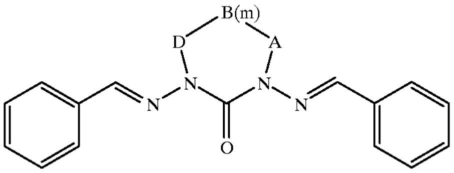

| No. | A | m | B | D | G | m.p. |
|---|---|---|---|---|---|---|
| 6.086. | CHEt | 0 | | $CH_2$ | CO | |
| 6.087. | CHEt | 1 | $CH_2$ | $CH_2$ | CO | |
| 6.088. | CHEt | 0 | | CHMe | CO | |
| 6.089. | CHEt | 1 | $CH_2$ | CHMe | CO | |
| 6.090. | CHEt | 0 | | CHEt | CO | |
| 6.091. | CHEt | 1 | $CH_2$ | CHEt | CO | |
| 6.092. | $CMe_2$ | 0 | | CO | CO | |
| 6.093. | $CMe_2$ | 1 | $CH_2$ | CO | CO | |
| 6.094. | $CMe_2$ | 0 | | $CH_2$ | CO | |
| 6.095. | $CMe_2$ | 1 | $CH_2$ | $CH_2$ | CO | |
| 6.096. | CMe= | 0 | | CH= | CO | 148–150° |
| 6.097. | CMe= | 1 | $CH_2$ | CH= | CO | |
| 6.098. | C(=NH) | 0 | | $CMe_2$ | CO | |
| 6.099. | C(=NH) | 1 | CH= | CMe= | CO | |
| 6.099. | C(=NH) | 1 | CH= | CMe= | CO | |
| 6.100. | C(OH)Me | 0 | | $CH_2$ | CO | 175–176° |
| 6.101. | C(OH)Et | 0 | | $CH_2$ | CO | |
| 6.102. | C(OH)iPr | 0 | | $CH_2$ | CO | |
| 6.103. | C(OH)cPr | 0 | | $CH_2$ | CO | |
| 6.104. | C(OH)Et | 1 | $CH_2$ | $CH_2$ | CO | |
| 6.105. | C(OH)iPr | 1 | $CH_2$ | $CH_2$ | CO | |
| 6.106. | C(OH)cPr | 1 | $CH_2$ | $CH_2$ | CO | |
| 6.107. | C(OH)Me | 1 | CHMe | $CH_2$ | CO | |
| 6.108. | CHOH | 1 | CHMe | $CH_2$ | CO | |
| 6.109. | C(OEt)Me | 0 | | $CH_2$ | CO | |
| 6.110. | C(OMe)Me | 0 | | $CH_2$ | CO | |

Example P26

3-(2-Cyclopropyl-2-oxo-ethyl)-5-methoxy-3H-[1,3,4] thiadiazol-2-one (Compound 7.055 in Table 7)

55 g of potassium carbonate are added to a solution of 26.4 g of 5-methoxy-3H-[1,3,4]-thiadiazol-2-one in 700 ml of dioxane and the reaction mixture is heated to 60°. Then 35 g of bromomethyl cyclopropyl ketone are added dropwise within a short period of time and the reaction mixture is stirred at 70° for 20 hours and then, at 20°, is filtered over Celite. The filtrate is concentrated by evaporation. The residue is stirred with diisopropyl ether and filtered with suction. 41 g of crystals of the title compound having a melting point of 98–100° are thus obtained.

Example P27

5-Methoxy-3-(2-oxopropyl)-3H-[1,3,4]thiadiazol-2-one (Compound 7.001 in Table 7)

69 g of potassium carbonate are added to a solution of 33 g of 5-methoxy-3H-[1,3,4]thiadiazol-2-one in 400 ml of dioxane and the reaction mixture is heated to 60°. Then 21 g of chloroacetone are added dropwise within a short period of time and the reaction mixture is stirred at 70° for 20 hours and then, at 20°, is filtered over Celite. The filtrate is concentrated by evaporation. The residue is stirred with diisopropyl ether and filtered with suction. 45 g of crystals of the title compound having a melting point of 66–67° are thus obtained.

Example P28

5-Methoxy-3-(1-ethoxy-2-oxopropyl)-3H-[1,3,4]thiadiazol-2-one (Compound 7.073 in Table 7)

69 g of potassium carbonate are added to a solution of 33 g of 5-methoxy-3H-[1,3,4]thiadiazol-2-one in 400 ml of dioxane and the reaction mixture is heated to 60°. Then 31 g of 1-chloro-3-ethoxypropan-2-one are added dropwise within a short period of time and the reaction mixture is stirred at 70° for 20 hours and then, at 20°, is filtered over Celite. The filtrate is concentrated by evaporation. 45 g of the title compound are thus obtained in the form of a light yellow oil.

Example P29

The other compounds listed in Table 7 can also be prepared in a manner analogous to that described in Examples P26 and P28.

TABLE 7

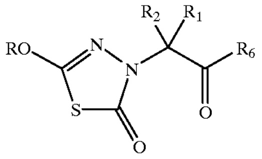

| No. | R | $R_1$ | $R_2$ | $R_6$ | m.p. |
|---|---|---|---|---|---|
| 7.001 | Me | H | H | Me | 64–65° |
| 7.002 | Et | H | H | Me | |
| 7.003 | nPr | H | H | Me | |
| 7.004 | Me | Me | H | Me | oil |
| 7.005 | Et | Me | H | Me | |
| 7.006 | nPr | Me | H | Me | |
| 7.007 | Me | Me | Me | Me | |
| 7.008 | Et | Me | Me | Me | |

TABLE 7-continued

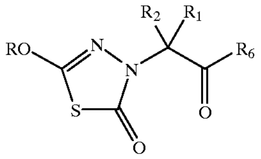

| No. | R | $R_1$ | $R_2$ | $R_6$ | m.p. |
|---|---|---|---|---|---|
| 7.009 | nPr | Me | Me | Me | |
| 7.010 | Me | H | H | Et | |
| 7.011 | Et | H | H | Et | |
| 7.012 | nPr | H | H | Et | |
| 7.013 | Me | Me | H | Et | |
| 7.014 | Et | Me | H | Et | |
| 7.015 | nPr | Me | H | Et | |
| 7.016 | Me | Me | Me | Et | |
| 7.017 | Et | Me | Me | Et | |
| 7.018 | nPr | Me | Me | Et | |
| 7.019 | Me | H | H | nPr | |
| 7.020 | Et | H | H | nPr | |
| 7.021 | nPr | H | H | nPr | |
| 7.022 | Me | Me | H | nPr | |
| 7.023 | Et | Me | H | nPr | |
| 7.024 | nPr | Me | H | nPr | |
| 7.025 | Me | Me | Me | nPr | |
| 7.026 | Et | Me | Me | nPr | |
| 7.027 | nPr | Me | Me | nPr | |
| 7.028 | Me | H | H | nBu | oil |
| 7.029 | Et | H | H | nBu | |
| 7.030 | nPr | H | H | nBu | |
| 7.031 | Me | Me | H | nBu | |
| 7.032 | Et | Me | H | nBu | |
| 7.033 | nPr | Me | H | nBu | |
| 7.034 | Me | Me | Me | nBu | |
| 7.035 | Et | Me | Me | nBu | |
| 7.036 | nPr | Me | Me | nBu | |
| 7.037 | Me | H | H | iPr | |
| 7.038 | Et | H | H | iPr | |
| 7.039 | nPr | H | H | iPr | |
| 7.040 | Me | Me | H | iPr | |
| 7.041 | Et | Me | H | iPr | |
| 7.042 | nPr | Me | H | iPr | |
| 7.043 | Me | Me | Me | iPr | |
| 7.044 | Et | Me | Me | iPr | |
| 7.045 | nPr | Me | Me | iPr | |
| 7.046 | Me | H | H | tBu | oil |
| 7.047 | Et | H | H | tBu | |
| 7.048 | nPr | H | H | tBu | |
| 7.049 | Me | Me | H | tBu | |
| 7.050 | Et | Me | H | tBu | |
| 7.051 | nPr | Me | H | tBu | |
| 7.052 | Me | Me | Me | tBu | |
| 7.053 | Et | Me | Me | tBu | |
| 7.054 | nPr | Me | Me | tBu | |
| 7.055 | Me | H | H | cPr | 98–100° |
| 7.056 | Et | H | H | cPr | |
| 7.057 | nPr | H | H | cPr | |
| 7.058 | Me | Me | H | cPr | |
| 7.059 | Et | Me | H | cPr | |
| 7.060 | nPr | Me | H | cPr | |
| 7.061 | Me | Me | Me | cPr | |
| 7.062 | Et | Me | Me | cPr | |
| 7.063 | nPr | Me | Me | cPr | |
| 7.064 | Me | H | H | $CH_2OMe$ | oil |
| 7.065 | Et | H | H | $CH_2OMe$ | |
| 7.066 | nPr | H | H | $CH_2OMe$ | |
| 7.067 | Me | Me | H | $CH_2OMe$ | |
| 7.068 | Et | Me | H | $CH_2OMe$ | |
| 7.069 | nPr | Me | H | $CH_2OMe$ | |
| 7.070 | Me | Me | Me | $CH_2OMe$ | |
| 7.071 | Et | Me | Me | $CH_2OMe$ | |
| 7.072 | nPr | Me | Me | $CH_2OMe$ | |
| 7.073 | Me | H | H | $CH_2OEt$ | oil |
| 7.074 | Et | H | H | $CH_2OEt$ | |
| 7.075 | nPr | H | H | $CH_2OEt$ | |
| 7.076 | Me | Me | H | $CH_2OEt$ | |

TABLE 7-continued

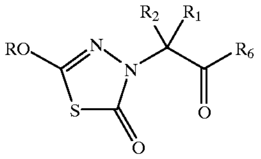

| No. | R | $R_1$ | $R_2$ | $R_6$ | m.p. |
|---|---|---|---|---|---|
| 7.077 | Et | Me | H | $CH_2OEt$ | |
| 7.078 | nPr | Me | H | $CH_2OEt$ | |
| 7.079 | Me | Me | Me | $CH_2OEt$ | |
| 7.080 | Et | Me | Me | $CH_2OEt$ | |
| 7.081 | nPr | Me | Me | $CH_2OEt$ | |
| 7.082 | Me | H | H | $CH_2OnPr$ | |
| 7.083 | Et | H | H | $CH_2OnPr$ | |
| 7.084 | nPr | H | H | $CH_2OnPr$ | |
| 7.085 | Me | Me | H | $CH_2OnPr$ | |
| 7.086 | Et | Me | H | $CH_2OnPr$ | |
| 7.087 | nPr | Me | H | $CH_2OnPr$ | |
| 7.088 | Me | Me | Me | $CH_2OnPr$ | |
| 7.089 | Et | Me | Me | $CH_2OnPr$ | |
| 7.090 | nPr | Me | Me | $CH_2OnPr$ | |
| 7.091 | Me | H | H | $CH_2SMe$ | |
| 7.092 | Et | H | H | $CH_2SMe$ | |
| 7.093 | nPr | H | H | $CH_2SMe$ | |
| 7.094 | Me | Me | H | $CH_2SMe$ | |
| 7.095 | Et | Me | H | $CH_2SMe$ | |
| 7.096 | nPr | Me | H | $CH_2SMe$ | |
| 7.097 | Me | Me | Me | $CH_2SMe$ | |
| 7.098 | Et | Me | Me | $CH_2SMe$ | |
| 7.099 | nPr | Me | Me | $CH_2SMe$ | |
| 7.100 | Me | H | H | $CH_2SEt$ | |
| 7.101 | Et | H | H | $CH_2SEt$ | |
| 7.102 | nPr | H | H | $CH_2SEt$ | |
| 7.103 | Me | Me | H | $CH_2SEt$ | |
| 7.104 | Et | Me | H | $CH_2SEt$ | |
| 7.105 | nPr | Me | H | $CH_2SEt$ | |
| 7.106 | Me | Me | Me | $CH_2SEt$ | |
| 7.107 | Et | Me | Me | $CH_2SEt$ | |
| 7.108 | nPr | Me | Me | $CH_2SEt$ | |
| 7.109 | Me | H | H | $CH_2SnPr$ | |
| 7.110 | Et | H | H | $CH_2SnPr$ | |
| 7.111 | nPr | H | H | $CH_2SnPr$ | |
| 7.112 | Me | Me | H | $CH_2SnPr$ | |
| 7.113 | Et | Me | H | $CH_2SnPr$ | |
| 7.114 | nPr | Me | H | $CH_2SnPr$ | |
| 7.115 | Me | Me | Me | $CH_2SnPr$ | |
| 7.116 | Et | Me | Me | $CH_2SnPr$ | |
| 7.117 | nPr | Me | Me | $CH_2SnPr$ | |
| 7.118 | Me | H | H | $CH_2OCOMe$ | 147–148° |

Example P30

Acetic acid [1-cyclopropyl-2-(5-methoxy-2-oxo-[1,3,4]thiadiazol-3-yl)-ethylidene]-hydrazide (Compound 8.055a in Table 8a)

16 g of acetyl hydrazide are added to a solution of 39.5 g of 3-(2-cyclopropyl-2-oxo-ethyl)-5-methoxy-3H-[1,3,4]thiadiazol-2-one (Comp. 7.055) in 350 ml of methanol and the mixture is then stirred at 55° for 16 hours. The reaction mixture is concentrated by evaporation, and the residue is stirred with ether/diisopropyl ether and filtered with suction to yield 40.5 g of crystals of the title compound having a melting point of 100–102°.

Example P31

Acetic acid [2-(5-methoxy-2-oxo-[1,3,4]thiadiazol-3-yl)-1-methylethylidene]-hydrazide (Compound 8.001a in Table 8a)

7.4 g of acetyl hydrazide are added to a solution of 18.8 g of 5-methoxy-3-(2-oxo-propyl)-3H-[1,3,4]thiadiazol-2-one (Comp. 7.001) in 150 ml of methanol and the mixture is then stirred at 55° for 2 hours. The reaction mixture is concentrated by evaporation and the residue is stirred with isopropanol and filtered with suction to yield 21.5 g of crystals of the title compound having a melting point of 151–153°.

Example P32

Acetic acid [1-ethoxymethyl-2-(5-methoxy-2-oxo-[1,3,4] thiadiazol-3-yl)-ethylidene]-hydrazide (Compound 8.073a in Table 8a)

12.6 g of acetyl hydrazide and 1 ml of acetic acid are added to a solution of 35.5 g of 3-(3-ethoxy-2-oxo-propyl)-5-methoxy-3H-[1,3,4]thiadiazol-2-one (Comp. 7.073) in 400 ml of methanol and 200 ml of tetrahydrofuran and the mixture is then stirred at 60° for 2 hours. The reaction mixture is concentrated by evaporation and the residue is stirred with isopropanol and filtered with suction to yield 31.5 g of crystals of the title compound having a melting point of 97–98°.

Example P33

The other compounds listed in Table 8a can also be prepared in a manner analogous to that described in Examples P30 to P32.

TABLE 8a

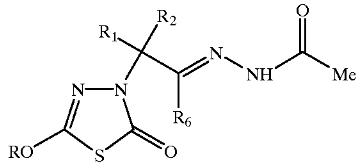

| Comp. | R | $R_1$ | $R_2$ | $R_6$ | m.p. |
|---|---|---|---|---|---|
| 8.001.a | Me | H | H | Me | 151–153° |
| 8.002.a | Et | H | H | Me | |
| 8.003.a | nPr | H | H | Me | |
| 8.004.a | Me | Me | H | Me | |
| 8.005.a | Et | Me | H | Me | 115–117° |
| 8.006.a | nPr | Me | H | Me | |
| 8.007.a | Me | Me | Me | Me | |
| 8.008.a | Et | Me | Me | Me | |
| 8.009.a | nPr | Me | Me | Me | |
| 8.010.a | Me | H | H | Et | |
| 8.011.a | Et | H | H | Et | |
| 8.012.a | nPr | H | H | Et | |
| 8.013.a | Me | Me | H | Et | |
| 8.014.a | Et | Me | H | Et | |
| 8.015.a | nPr | Me | H | Et | |
| 8.016.a | Me | Me | Me | Et | |
| 8.017.a | Et | Me | Me | Et | |
| 8.018.a | nPr | Me | Me | Et | |
| 8.019.a | Me | H | H | nPr | |
| 8.020.a | Et | H | H | nPr | |
| 8.021.a | nPr | H | H | nPr | |
| 8.022.a | Me | Me | H | nPr | |
| 8.023.a | Et | Me | H | nPr | |
| 8.024.a | nPr | Me | H | nPr | |
| 8.025.a | Me | Me | Me | nPr | |
| 8.026.a | Et | Me | Me | nPr | |
| 8.027.a | nPr | Me | Me | nPr | |
| 8.028.a | Me | H | H | nBu | 98–99° |
| 8.029.a | Et | H | H | nBu | |
| 8.030.a | nPr | H | H | nBu | |
| 8.031.a | Me | Me | H | nBu | |
| 8.032.a | Et | Me | H | nBu | |
| 8.033.a | nPr | Me | H | nBu | |
| 8.034.a | Me | Me | Me | nBu | |
| 8.035.a | Et | Me | Me | nBu | |
| 8.036.a | nPr | Me | Me | nBu | |
| 8.037.a | Me | H | H | iPr | |
| 8.038.a | Et | H | H | iPr | |

TABLE 8a-continued

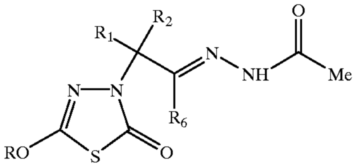

| Comp. | R | $R_1$ | $R_2$ | $R_6$ | m.p. |
|---|---|---|---|---|---|
| 8.039.a | nPr | H | H | iPr | |
| 8.040.a | Me | Me | H | iPr | |
| 8.041.a | Et | Me | H | iPr | |
| 8.042.a | nPr | Me | H | iPr | |
| 8.043.a | Me | Me | Me | iPr | |
| 8.044.a | Et | Me | Me | iPr | |
| 8.045.a | nPr | Me | Me | iPr | |
| 8.046.a | Me | H | H | tBu | 119–120° |
| 8.047.a | Et | H | H | tBu | |
| 8.048.a | nPr | H | H | tBu | |
| 8.049.a | Me | Me | H | tBu | |
| 8.050.a | Et | Me | H | tBu | |
| 8.051.a | nPr | Me | H | tBu | |
| 8.052.a | Me | Me | Me | tBu | |
| 8.053.a | Et | Me | Me | tBu | |
| 8.054.a | nPr | Me | Me | tBu | |
| 8.055.a | Me | H | H | cPr | 100–102° |
| 8.056.a | Et | H | H | cPr | |
| 8.057.a | nPr | H | H | cPr | |
| 8.058.a | Me | Me | H | cPr | |
| 8.059.a | Et | Me | H | cPr | |
| 8.060.a | nPr | Me | H | cPr | |
| 8.061.a | Me | Me | Me | cPr | |
| 8.062.a | Et | Me | Me | cPr | |
| 8.063.a | nPr | Me | Me | cPr | |
| 8.064.a | Me | H | H | $CH_2OMe$ | 102–104° |
| 8.065.a | Et | H | H | $CH_2OMe$ | |
| 8.066.a | nPr | H | H | $CH_2OMe$ | |
| 8.067.a | Me | Me | H | $CH_2OMe$ | |
| 8.068.a | Et | Me | H | $CH_2OMe$ | |
| 8.069.a | nPr | Me | H | $CH_2OMe$ | |
| 8.070.a | Me | Me | Me | $CH_2OMe$ | |
| 8.071.a | Et | Me | Me | $CH_2OMe$ | |
| 8.072.a | nPr | Me | Me | $CH_2OMe$ | |
| 8.073.a | Me | H | H | $CH_2OEt$ | 97–98° |
| 8.074.a | Et | H | H | $CH_2OEt$ | |
| 8.075.a | nPr | H | H | $CH_2OEt$ | |
| 8.076.a | Me | Me | H | $CH_2OEt$ | |
| 8.077.a | Et | Me | H | $CH_2OEt$ | |
| 8.078.a | nPr | Me | H | $CH_2OEt$ | |
| 8.079.a | Me | Me | Me | $CH_2OEt$ | |
| 8.080.a | Et | Me | Me | $CH_2OEt$ | |
| 8.081.a | nPr | Me | Me | $CH_2OEt$ | |
| 8.082.a | Me | H | H | $CH_2OnPr$ | |
| 8.083.a | Et | H | H | $CH_2OnPr$ | |
| 8.084.a | nPr | H | H | $CH_2OnPr$ | |
| 8.085.a | Me | Me | H | $CH_2OnPr$ | |
| 8.086.a | Et | Me | H | $CH_2OnPr$ | |
| 8.087.a | nPr | Me | H | $CH_2OnPr$ | |
| 8.988.a | Me | Me | Me | $CH_2OnPr$ | |
| 8.089.a | Et | Me | Me | $CH_2OnPr$ | |
| 8.090.a | nPr | Me | Me | $CH_2OnPr$ | |
| 8.091.a | Me | H | H | $CH_2SMe$ | |
| 8.092.a | Et | H | H | $CH_2SMe$ | |
| 8.093.a | nPr | H | H | $CH_2SMe$ | |
| 8.094.a | Me | Me | H | $CH_2SMe$ | |
| 8.095.a | Et | Me | H | $CH_2SMe$ | |
| 8.096.a | nPr | Me | H | $CH_2SMe$ | |
| 8.097.a | Me | Me | Me | $CH_2SMe$ | |
| 8.098.a | Et | Me | Me | $CH_2SMe$ | |
| 8.099.a | nPr | Me | Me | $CH_2SMe$ | |
| 8.100.a | Me | H | H | $CH_2SEt$ | |
| 8.101.a | Et | H | H | $CH_2SEt$ | |
| 8.102.a | nPr | H | H | $CH_2SEt$ | |
| 8.103.a | Me | Me | H | $CH_2SEt$ | |
| 8.104.a | Et | Me | H | $CH_2SEt$ | |
| 8.105.a | nPr | Me | H | $CH_2SEt$ | |

TABLE 8a-continued

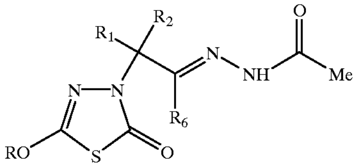

| Comp. | R | $R_1$ | $R_2$ | $R_6$ | m.p. |
|---|---|---|---|---|---|
| 8.106.a | Me | Me | Me | $CH_2SEt$ | |
| 8.107.a | Et | Me | Me | $CH_2SEt$ | |
| 8.108.a | nPr | Me | Me | $CH_2SEt$ | |
| 8.109.a | Me | H | H | $CH_2SnPr$ | |
| 8.110.a | Et | H | H | $CH_2SnPr$ | |
| 8.111.a | nPr | H | H | $CH_2SnPr$ | |
| 8.112.a | Me | Me | H | $CH_2SnPr$ | |
| 8.113.a | Et | Me | H | $CH_2SnPr$ | |
| 8.114.a | nPr | Me | H | $CH_2SnPr$ | |
| 8.115.a | Me | Me | Me | $CH_2SnPr$ | |
| 8.116.a | Et | Me | Me | $CH_2SnPr$ | |
| 8.117.a | nPr | Me | Me | $CH_2SnPr$ | |

Example P34

N'-[2-(5-Methoxy-2-oxo-[1,3,4]thiadiazol-3-yl)-1-methyl-ethylidene]-hydrazinecarboxylic acid methyl ester (Compound 8.001b in Table 8b)

9.1 g of methyl carbazate are added to a solution of 18.8 g of 5-methoxy-3-(2-oxo-propyl)-3H-[1,3,4]thiadiazol-2-one (Comp. 7.001) in 150 ml of methanol and the mixture is then stirred at room temperature for 36 hours. The reaction mixture is concentrated by evaporation and the residue is stirred with isopropanol and filtered with suction to yield 20.5 g of crystals of the title compound having a melting point of 142–143°.

Example P35

The other compounds listed in Table 8b can also be prepared in a manner analogous to that described in Example P34.

TABLE 8b

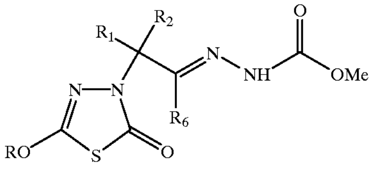

| Comp. | R | $R_1$ | $R_2$ | $R_6$ | m.p. |
|---|---|---|---|---|---|
| 8.001.b | Me | H | H | Me | 142–143° |
| 8.002.b | Et | H | H | Me | |
| 8.003.b | nPr | H | H | Me | |
| 8.004.b | Me | Me | H | Me | |
| 8.005.b | Et | Me | H | Me | |
| 8.006.b | nPr | Me | H | Me | |
| 8.007.b | Me | Me | Me | Me | |
| 8.008.b | Et | Me | Me | Me | |
| 8.009.b | nPr | Me | Me | Me | |
| 8.010.b | Me | H | H | Et | |
| 8.011.b | Et | H | H | Et | |
| 8.012.b | nPr | H | H | Et | |
| 8.013.b | Me | Me | H | Et | |
| 8.014.b | Et | Me | H | Et | |
| 8.015.b | nPr | Me | H | Et | |
| 8.016.b | Me | Me | Me | Et | |
| 8.017.b | Et | Me | Me | Et | |
| 8.018.b | nPr | Me | Me | Et | |

TABLE 8b-continued

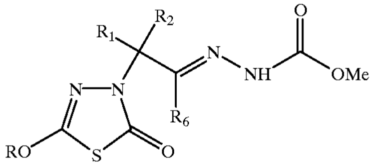

| Comp. | R | $R_1$ | $R_2$ | $R_6$ | m.p. |
|---|---|---|---|---|---|
| 8.019.b | Me | H | H | nPr | |
| 8.020.b | Et | H | H | nPr | |
| 8.021.b | nPr | H | H | nPr | |
| 8.022.b | Me | Me | H | nPr | |
| 8.023.b | Et | Me | H | nPr | |
| 8.024.b | nPr | Me | H | nPr | |
| 8.025.b | Me | Me | Me | nPr | |
| 8.026.b | Et | Me | Me | nPr | |
| 8.027.b | nPr | Me | Me | nPr | |
| 8.028.b | Me | H | H | nBu | |
| 8.029.b | Et | H | H | nBu | |
| 8.030.b | nPr | H | H | nBu | |
| 8.031.b | Me | Me | H | nBu | |
| 8.032.b | Et | Me | H | nBu | |
| 8.033.b | nPr | Me | H | nBu | |
| 8.034.b | Me | Me | Me | nBu | |
| 8.035.b | Et | Me | Me | nBu | |
| 8.036.b | nPr | Me | Me | nBu | |
| 8.037.b | Me | H | H | iPr | |
| 8.038.b | Et | H | H | iPr | |
| 8.039.b | nPr | H | H | iPr | |
| 8.040.b | Me | Me | H | iPr | |
| 8.041.b | Et | Me | H | iPr | |
| 8.042.b | nPr | Me | H | iPr | |
| 8.043.b | Me | Me | Me | iPr | |
| 8.044.b | Et | Me | Me | iPr | |
| 8.045.b | nPr | Me | Me | iPr | |
| 8.046.b | Me | H | H | tBu | |
| 8.047.b | Et | H | H | tBu | |
| 8.048.b | nPr | H | H | tBu | |
| 8.049.b | Me | Me | H | tBu | |
| 8.050.b | Et | Me | H | tBu | |
| 8.051.b | nPr | Me | H | tBu | |
| 8.052.b | Me | Me | Me | tBu | |
| 8.053.b | Et | Me | Me | tBu | |
| 8.054.b | nPr | Me | Me | tBu | |
| 8.055.b | Me | H | H | cPr | |
| 8.056.b | Et | H | H | cPr | |
| 8.057.b | nPr | H | H | cPr | |
| 8.058.b | Me | Me | H | cPr | |
| 8.059.b | Et | Me | H | cPr | |
| 8.060.b | nPr | Me | H | cPr | |
| 8.061.b | Me | Me | Me | cPr | |
| 8.062.b | Et | Me | Me | cPr | |
| 8.063.b | nPr | Me | Me | cPr | |
| 8.064.b | Me | H | H | $CH_2OMe$ | |
| 8.065.b | Et | H | H | $CH_2OMe$ | |
| 8.066.b | nPr | H | H | $CH_2OMe$ | |
| 8.067.b | Me | Me | H | $CH_2OMe$ | |
| 8.068.b | Et | Me | H | $CH_2OMe$ | |
| 8.069.b | nPr | Me | H | $CH_2OMe$ | |
| 8.070.b | Me | Me | Me | $CH_2OMe$ | |
| 8.071.b | Et | Me | Me | $CH_2OMe$ | |
| 8.072.b | nPr | Me | Me | $CH_2OMe$ | |
| 8.073.b | Me | H | H | $CH_2OEt$ | |
| 8.074.b | Et | H | H | $CH_2OEt$ | |
| 8.075.b | nPr | H | H | $CH_2OEt$ | |
| 8.076.b | Me | Me | H | $CH_2OEt$ | |
| 8.077.b | Et | Me | H | $CH_2OEt$ | |
| 8.078.b | nPr | Me | H | $CH_2OEt$ | |
| 8.079.b | Me | Me | Me | $CH_2OEt$ | |
| 8.080.b | Et | Me | Me | $CH_2OEt$ | |
| 8.081.b | nPr | Me | Me | $CH_2OEt$ | |
| 8.082.b | Me | H | H | $CH_2OnPr$ | |
| 8.083.b | Et | H | H | $CH_2OnPr$ | |
| 8.084.b | nPr | H | H | $CH_2OnPr$ | |
| 8.085.b | Me | Me | H | $CH_2OnPr$ | |

TABLE 8b-continued

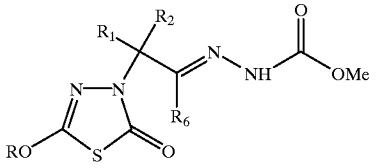

| Comp. | R | $R_1$ | $R_2$ | $R_6$ | m.p. |
|---|---|---|---|---|---|
| 8.086.b | Et | Me | H | $CH_2OnPr$ | |
| 8.087.b | nPr | Me | H | $CH_2OnPr$ | |
| 8.088.b | Me | Me | Me | $CH_2OnPr$ | |
| 8.089.b | Et | Me | Me | $CH_2OnPr$ | |
| 8.090.b | nPr | Me | Me | $CH_2OnPr$ | |
| 8.091.b | Me | H | H | $CH_2SMe$ | |
| 8.092.b | Et | H | H | $CH_2SMe$ | |
| 8.093.b | nPr | H | H | $CH_2SMe$ | |
| 8.094.b | Me | Me | H | $CH_2SMe$ | |
| 8.095.b | Et | Me | H | $CH_2SMe$ | |
| 8.096.b | nPr | Me | H | $CH_2SMe$ | |
| 8.097.b | Me | Me | Me | $CH_2SMe$ | |
| 8.098.b | Et | Me | Me | $CH_2SMe$ | |
| 8.099.b | nPr | Me | Me | $CH_2SMe$ | |
| 8.100.b | Me | H | H | $CH_2SEt$ | |
| 8.101.b | Et | H | H | $CH_2SEt$ | |
| 8.102.b | nPr | H | H | $CH_2SEt$ | |
| 8.103.b | Me | Me | H | $CH_2SEt$ | |
| 8.104.b | Et | Me | H | $CH_2SEt$ | |
| 8.105.b | nPr | Me | H | $CH_2SEt$ | |
| 8.106.b | Me | Me | Me | $CH_2SEt$ | |
| 8.107.b | Et | Me | Me | $CH_2SEt$ | |
| 8.108.b | nPr | Me | Me | $CH_2SEt$ | |
| 8.109.b | Me | H | H | $CH_2SnPr$ | |
| 8.110.b | Et | H | H | $CH_2SnPr$ | |
| 8.111.b | nPr | H | H | $CH_2SnPr$ | |
| 8.112.b | Me | Me | H | $CH_2SnPr$ | |
| 8.113.b | Et | Me | H | $CH_2SnPr$ | |
| 8.114.b | nPr | Me | H | $CH_2SnPr$ | |
| 8.115.b | Me | Me | Me | $CH_2SnPr$ | |
| 8.116.b | Et | Me | Me | $CH_2SnPr$ | |
| 8.117.b | nPr | Me | Me | $CH_2SnPr$ | |

Example P36

(6-Methyl-3-oxo-2,5-dihydro-3H-[1,3,4]triazin-4-yl)-thiocarbamic acid O-methyl ester (Compound 9.001 in Table 9)

14.5 ml of a 30% solution of sodium methoxide are added dropwise to a suspension of 18.7 g of acetic acid [2-(5-methoxy-2-oxo-[1,3,4]thiadiazol-3-yl)-1-methylethylidene]-hydrazide (Comp. 8.001a) in 200 ml of methanol and the mixture is then stirred at room temperature for 3 hours. The mixture is then concentrated by evaporation, 250 ml of water are added, the mixture is rendered slightly acidic by the addition of hydrochloric acid and then extracted three times with 100 ml of ethyl acetate. The organic phase is dried using magnesium sulfate and concentrated by evaporation to yield 9 g of crystals of the title compound having a melting point of 185–187°.

Example P37

(6-Ethoxymethyl-3-oxo-2,5-dihydro-3H-[1,3,4]triazin-4-yl)-thiocarbamic acid O-methyl ester (Compound 9.073 in Table 9)

25 ml of a 30% solution of sodium methoxide are added dropwise to a suspension of 29.9 g of acetic acid [1-ethoxymethyl-2-(5-methoxy-2-oxo-[1,3,4]thiadiazol-3-yl)-ethylidene]-hydrazide (Comp. 8.073a) in 250 ml of methanol and the mixture is then stirred at 60° for 2 hours. The mixture is then concentrated by evaporation, 250 ml of water are added, the mixture is adjusted to pH 4.5 using hydrochloric acid and then extracted three times with 100 ml of ethyl acetate. The organic phase is dried using magnesium sulfate and concentrated by evaporation to yield 20.6 g of crystals of the title compound having a melting point of 132–134°.

Example P38

(6-Cyclopropyl-3-oxo-2,5-dihydro-3H-[1,3,4]triazin-4-yl)-thiocarbamic acid O-methyl ester (Compound 9.055 in Table 9)

33 ml of a 30% solution of sodium methoxide are added dropwise at 50° to a solution of 39.5 g of acetic acid [1-cyclopropyl-2-(5-methoxy-2-oxo-[1,3,4]thiadiazol-3-yl)-ethylidene]-hydrazide (Comp. 8.055a) in 500 ml of methanol and the mixture is then stirred at 60° for 4 hours. The mixture is then concentrated by evaporation, 400 ml of water are added and the mixture is adjusted to pH 2 using hydrochloric acid, whereupon the product precipitates in the form of crystals. The mixture is dried overnight at 60° in vacuo, to yield 24.6 g of crystals of the title compound having a melting point of 163–166°.

Example P39

The compounds listed in Table 8b can also be prepared in a manner analogous to that described in Examples P36 to P38.

TABLE 9

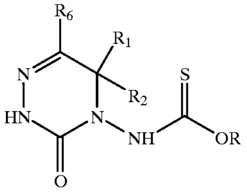

| Comp. | R | $R_1$ | $R_2$ | $R_6$ | m.p. |
|---|---|---|---|---|---|
| 9.001 | Me | H | H | Me | 185–187° |
| 9.002 | Et | H | H | Me | |
| 9.003 | nPr | H | H | Me | |
| 9.004 | Me | Me | H | Me | 202–203° |
| 9.005 | Et | Me | H | Me | |
| 9.006 | nPr | Me | H | Me | |
| 9.007 | Me | Me | Me | Me | |
| 9.008 | Et | Me | Me | Me | |
| 9.009 | nPr | Me | Me | Me | |
| 9.010 | Me | H | H | Et | |
| 9.011 | Et | H | H | Et | |
| 9.012 | nPr | H | H | Et | |
| 9.013 | Me | Me | H | Et | |
| 9.014 | Et | Me | H | Et | |
| 9.015 | nPr | Me | H | Et | |
| 9.016 | Me | Me | Me | Et | |
| 9.017 | Et | Me | Me | Et | |
| 9.018 | nPr | Me | Me | Et | |
| 9.019 | Me | H | H | nPr | |
| 9.020 | Et | H | H | nPr | |
| 9.021 | nPr | H | H | nPr | |
| 9.022 | Me | Me | H | nPr | |
| 9.023 | Et | Me | H | nPr | |
| 9.024 | nPr | Me | H | nPr | |
| 9.025 | Me | Me | Me | nPr | |
| 9.026 | Et | Me | Me | nPr | |
| 9.027 | nPr | Me | Me | nPr | |
| 9.028 | Me | H | H | nBu | |
| 9.029 | Et | H | H | nBu | |
| 9.030 | nPr | H | H | nBu | |
| 9.031 | Me | Me | H | nBu | |
| 9.032 | Et | Me | H | nBu | |
| 9.033 | nPr | Me | H | nBu | |
| 9.034 | Me | Me | Me | nBu | |
| 9.035 | Et | Me | Me | nBu | |

TABLE 9-continued

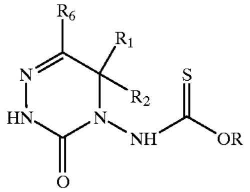

| Comp. | R | $R_1$ | $R_2$ | $R_6$ | m.p. |
|---|---|---|---|---|---|
| 9.036 | nPr | Me | Me | nBu | |
| 9.037 | Me | H | H | iPr | |
| 9.038 | Et | H | H | iPr | |
| 9.039 | nPr | H | H | iPr | |
| 9.040 | Me | Me | H | iPr | |
| 9.041 | Et | Me | H | iPr | |
| 9.042 | nPr | Me | H | iPr | |
| 9.043 | Me | Me | Me | iPr | |
| 9.044 | Et | Me | Me | iPr | |
| 9.045 | nPr | Me | Me | iPr | |
| 9.046 | Me | H | H | tBu | 203–205° |
| 9.047 | Et | H | H | tBu | |
| 9.048 | nPr | H | H | tBu | |
| 9.049 | Me | Me | H | tBu | |
| 9.050 | Et | Me | H | tBu | |
| 9.051 | nPr | Me | H | tBu | |
| 9.052 | Me | Me | Me | tBu | |
| 9.053 | Et | Me | Me | tBu | |
| 9.054 | nPr | Me | Me | tBu | |
| 9.055 | Me | H | H | cPr | 163–166° |
| 9.056 | Et | H | H | cPr | |
| 9.057 | nPr | H | H | cPr | |
| 9.058 | Me | Me | H | cPr | |
| 9.059 | Et | Me | H | cPr | |
| 9.060 | nPr | Me | H | cPr | |
| 9.061 | Me | Me | Me | cPr | |
| 9.062 | Et | Me | Me | cPr | |
| 9.063 | nPr | Me | Me | cPr | |
| 9.064 | Me | H | H | $CH_2OMe$ | 165–167° |
| 9.065 | Et | H | H | $CH_2OMe$ | |
| 9.066 | nPr | H | H | $CH_2OMe$ | |
| 9.067 | Me | Me | H | $CH_2OMe$ | |
| 9.068 | Et | Me | H | $CH_2OMe$ | |
| 9.069 | nPr | Me | H | $CH_2OMe$ | |
| 9.070 | Me | Me | Me | $CH_2OMe$ | |
| 9.071 | Et | Me | Me | $CH_2OMe$ | |
| 9.072 | nPr | Me | Me | $CH_2OMe$ | |
| 9.073 | Me | H | H | $CH_2OEt$ | 132–134° |
| 9.074 | Et | H | H | $CH_2OEt$ | |
| 9.075 | nPr | H | H | $CH_2OEt$ | |
| 9.076 | Me | Me | H | $CH_2OEt$ | |
| 9.077 | Et | Me | H | $CH_2OEt$ | |
| 9.078 | nPr | Me | H | $CH_2OEt$ | |
| 9.079 | Me | Me | Me | $CH_2OEt$ | |
| 9.080 | Et | Me | Me | $CH_2OEt$ | |
| 9.081 | nPr | Me | Me | $CH_2OEt$ | |
| 9.082 | Me | H | H | $CH_2OnPr$ | |
| 9.083 | Et | H | H | $CH_2OnPr$ | |
| 9.084 | nPr | H | H | $CH_2OnPr$ | |
| 9.085 | Me | Me | H | $CH_2OnPr$ | |
| 9.086 | Et | Me | H | $CH_2OnPr$ | |
| 9.087 | nPr | Me | H | $CH_2OnPr$ | |
| 9.088 | Me | Me | Me | $CH_2OnPr$ | |
| 9.089 | Et | Me | Me | $CH_2OnPr$ | |
| 9.090 | nPr | Me | Me | $CH_2OnPr$ | |
| 9.091 | Me | H | H | $CH_2SMe$ | |
| 9.092 | Et | H | H | $CH_2SMe$ | |
| 9.093 | nPr | H | H | $CH_2SMe$ | |
| 9.094 | Me | Me | H | $CH_2SMe$ | |
| 9.095 | Et | Me | H | $CH_2SMe$ | |
| 9.096 | nPr | Me | H | $CH_2SMe$ | |
| 9.097 | Me | Me | Me | $CH_2SMe$ | |
| 9.098 | Et | Me | Me | $CH_2SMe$ | |
| 9.099 | nPr | Me | Me | $CH_2SMe$ | |
| 9.100 | Me | H | H | $CH_2SEt$ | |
| 9.101 | Et | H | H | $CH_2SEt$ | |

TABLE 9-continued

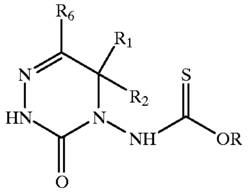

| Comp. | R | $R_1$ | $R_2$ | $R_6$ | m.p. |
|---|---|---|---|---|---|
| 9.102 | nPr | H | H | $CH_2SEt$ | |
| 9.103 | Me | Me | H | $CH_2SEt$ | |
| 9.104 | Et | Me | H | $CH_2SEt$ | |
| 9.105 | nPr | Me | H | $CH_2SEt$ | |
| 9.106 | Me | Me | Me | $CH_2SEt$ | |
| 9.107 | Et | Me | Me | $CH_2SEt$ | |
| 9.108 | nPr | Me | Me | $CH_2SEt$ | |
| 9.109 | Me | H | H | $CH_2SnPr$ | |
| 9.110 | Et | H | H | $CH_2SnPr$ | |
| 9.111 | nPr | H | H | $CH_2SnPr$ | |
| 9.112 | Me | Me | H | $CH_2SnPr$ | |
| 9.113 | Et | Me | H | $CH_2SnPr$ | |
| 9.114 | nPr | Me | H | $CH_2SnPr$ | |
| 9.115 | Me | Me | Me | $CH_2SnPr$ | |
| 9.116 | Et | Me | Me | $CH_2SnPr$ | |
| 9.117 | nPr | Me | Me | $CH_2SnPr$ | |
| 9.118 | Me | H | H | $CH_2OH$ | 165–170° |

Formulation Examples (throughout, percentages are by weight)

| Example F1: Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

The finely ground active ingredient is mixed with the adjuvants, giving an emulsifiable concentrate from which emulsions of any desired concentration can be prepared by dilution with water.

| Example F2: Solutions | a) | b) | c) | d) |
|---|---|---|---|---|
| active ingredient | 80% | 10% | 5% | 95% |
| ethylene glycol monomethyl ether | 20% | — | — | — |
| polyethylene glycol (mol. wt. 400) | — | 70% | — | — |
| N-methylpyrrolid-2-one | — | 20% | — | — |
| epoxidised coconut oil | — | — | 1% | 5% |
| petroleum fraction (boiling range 160–190° C.) | — | — | 94% | — |

The finely ground active ingredient is mixed with the adjuvants, giving a solution that is suitable for applcation in the form of microdrops.

| Example F3: Granules | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier mixture, and the solvent is evaporated off in vacuo.

| Example F4: Dusts | a) | b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by mixing the active ingredient with the carriers.

| Example F5: Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is ground in a suitable mill, affording wettable powders which can be diluted with water to give suspensions of any desired concentration.

| Example F6: Emulsifiable concentrate | |
|---|---|
| active ingredient | 10% |
| octylphenol polyethylene glycol ether (4–5 mol of ethylene oxide) | 3% |
| calcium dodecylbenzenesulfonate | 3% |
| castor oil polyethylene glycol ether (36 mol of ethylene oxide) | 4% |
| cyclohexanone | 30% |
| xylene mixture | 50% |

The finely ground active ingredient is mixed with the adjuvants, giving an emulsifiable concentrate from which emulsions of any desired concentration can be prepared by dilution with water.

| Example F7: Dusts | a) | b) |
|---|---|---|
| active ingredient | 5% | 8% |
| talcum | 95% | — |
| kaolin | — | 92% |

Ready-for-use dusts are obtained by mixing the active ingredient with the carrier and grinding the mixture in a suitable mill.

| Example F8: Extruder granules | |
|---|---|
| active ingredient | 10% |
| sodium lignosulfonate | 2% |
| carboxymethylcellulose | 1% |
| kaolin | 87% |

The active ingredient is mixed with the adjuvants, and the mixture is ground, moistened with water, extruded and granulated, and the granules are then dried in a stream of air.

| Example F9: Coated granules | |
|---|---|
| active ingredient | 3% |
| polyethylene glycol (mol. wt. 200) | 3% |
| kaolin | 94% |

The finely ground active ingredient is uniformly applied, in a mixer, to the kaolin moistened with polyethylene glycol, affording non-dusty coated granules.

| Example F10: Suspension concentrate | |
|---|---|
| active ingredient | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

The finely ground active ingredient is mixed with the adjuvants, giving a suspension concentrate from which suspensions of any desired concentration can be obtained by dilution with water.

BIOLOGICAL EXAMPLES

Example B1: Action Against *Aphis craccivora*

Pea seedlings are infested with *Aphis craccivora* and then sprayed with a spray mixture comprising 400 ppm of test compound, and incubated at 20° C. Evaluation is made 3 and 6 days later. The percentage reduction in the population (% activity) is determined by comparing the number of dead aphids on the treated plants with that on untreated plants.

Compounds of Tables 1 and 1b exhibit good activity in this test. In particular, Compound No. 1.072 is more than 80% effective.

Example B2: Action Against *Nilaparvata lugens*

Rice plants are sprayed with an aqueous emulsion comprising 400 ppm of test compound. After the spray coating has dried, the rice plants are populated with plant hopper larvae in the 2nd and 3rd stages. Evaluation is made 21 days later. The percentage reduction in the population (% activity) is determined by comparing the number of surviving plant hoppers on the treated plants with that on untreated plants.

Compounds of Tables 1 and 1b exhibit good activity in this test. In particular, Compound No. 1.072 is more than 80% effective.

Example B3: Action Against *Nilaparvata lugens* (systemic)

Pots containing rice plants are stood in an aqueous emulsion comprising 10 ppm of test compound. The plants are then populated with larvae in the 2nd and 3rd stages. Evaluation is made 6 days later. The percentage reduction in the population (% activity) is determined by comparing the number of plant hoppers on the treated plants with that on untreated plants.

Compounds of Tables 1 and 1b exhibit good activity in this test. In particular, Compound No. 1.072 is more than 80% effective.

What is claimed is:

1. A compound of the formula

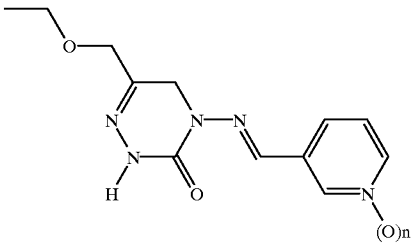

wherein n is 0 or 1, or, a tautomer or salt thereof.

2. A compound according to claim 1, wherein n is 0.

3. A compound according to claim 1, wherein n is 1.

4. A pesticidal composition which comprises as active ingredient at least one compound according to claim 1 or, where appropriate, a tautomer thereof, in each case in free form or in agrochemically acceptable salt form, and at least one adjuvant.

5. A method of controlling pests, which comprises applying to the pests or to the habitat thereof a compound according to claim 1 or, where appropriate, a tautomer thereof, in each case in free form or in agrochemically acceptable salt form.

6. A method according to claim 5 of protecting plant propagation material, which comprises treating the propagation material or the planting site of the propagation material.

7. Plant propagation material treated in accordance with the method described in claim 6.

* * * * *